US011555204B2

(12) United States Patent
Masuda et al.

(10) Patent No.: US 11,555,204 B2
(45) Date of Patent: Jan. 17, 2023

(54) PROMOTER OF HSPA5 GENE

(71) Applicant: Daiichi Sankyo Company, Limited, Tokyo (JP)

(72) Inventors: Kenji Masuda, Chuo-ku (JP); Koichi Nonaka, Chuo-ku (JP); Hiroki Tanemura, Chuo-ku (JP)

(73) Assignee: Daiichi Sankyo Company, Limited, Chuo-ku (JP)

( * ) Notice: Subject to any disclaimer, the term of this patent is extended or adjusted under 35 U.S.C. 154(b) by 749 days.

(21) Appl. No.: 16/338,941

(22) PCT Filed: Oct. 2, 2017

(86) PCT No.: PCT/JP2017/035773
§ 371 (c)(1),
(2) Date: Apr. 2, 2019

(87) PCT Pub. No.: WO2018/066492
PCT Pub. Date: Apr. 12, 2018

(65) Prior Publication Data
US 2019/0241907 A1 Aug. 8, 2019

(30) Foreign Application Priority Data
Oct. 3, 2016 (JP) .............................. JP2016-195564

(51) Int. Cl.
| C12N 15/85 | (2006.01) |
| C12P 21/02 | (2006.01) |
| C12N 15/113 | (2010.01) |
| C12N 15/09 | (2006.01) |
| C12N 5/10 | (2006.01) |

(52) U.S. Cl.
CPC ............... *C12N 15/85* (2013.01); *C12N 5/10* (2013.01); *C12N 15/09* (2013.01); *C12N 15/113* (2013.01); *C12P 21/02* (2013.01); *C12N 2015/8518* (2013.01); *C12N 2830/85* (2013.01)

(58) Field of Classification Search
CPC .......... C12N 15/85; C12N 15/09; C12N 5/10; C12N 2830/85; C07K 14/47
See application file for complete search history.

(56) References Cited

U.S. PATENT DOCUMENTS

| 5,196,523 | A | 3/1993 | Lee |
| 5,225,348 | A | 7/1993 | Nagata et al. |
| 9,322,034 | B2 | 4/2016 | Carlock et al. |
| 9,862,969 | B2 | 1/2018 | Murakami |
| 2003/0083257 | A1 | 5/2003 | Negrier et al. |
| 2011/0065100 | A1 | 3/2011 | Aldred et al. |
| 2011/0268701 | A1 | 11/2011 | Amy |
| 2013/0171694 | A1 | 7/2013 | Nishimiya et al. |
| 2015/0361451 | A1 | 12/2015 | Le Fourn et al. |

FOREIGN PATENT DOCUMENTS

| CN | 1454900 A | 11/2003 |
| CN | 101861391 A | 10/2010 |
| CN | 103080321 A | 5/2013 |
| CN | 104066839 A | 9/2014 |
| CN | 105073995 A | 9/2016 |
| CN | 105950621 A | 9/2016 |
| EP | 0533862 B1 | 10/1999 |
| JP | 3051411 B2 | 3/2000 |
| JP | 2013-531967 A | 8/2013 |
| JP | 2013531967 A | 8/2013 |
| JP | 2016-504922 A | 2/2016 |
| JP | 2016504922 A | 2/2016 |
| KR | 10-2015-0123803 B1 | 11/2015 |
| WO | 2008/073303 A2 | 6/2008 |
| WO | 2012005378 A2 | 1/2012 |
| WO | 2013/080934 A1 | 6/2013 |
| WO | 2014118619 A2 | 8/2014 |
| WO | WO-2014118619 A2 * | 8/2014 ............. C07K 16/00 |

OTHER PUBLICATIONS

GenBank CP068269.2. GenBank. 2021. p. 1-2 (Year: 2021).*
Partial Supplementary European Search Report dated Mar. 11, 2020, issued in European Application No. 17858330.8, filed Oct. 2, 2017, 17 pages.
Livingston, R.J., et al., "*Homo sapiens* heat shock 70kDa protein 5 (glucose-regulated protein, 78kDa) (HSPA5) gene, complete cds," submitted Jan. 31, 2006 to GenBank: DQ385847.1, NIEHS-SNPs, Environmental Genome Project, NIEHS ES15478, Department of Genome Sciences, Seattle, Wash., 6 pages.
Boshart, M., et al., "A Very Strong Enhancer is Located Upstream of an Immediate Early Gene of Human Cytomegalovirus," Cell 41:521-530, Jun. 1985.
Durocher, Y., and M. Butler, "Expression Systems for Therapeutic Glycoprotein Production," Current Opinion in Biotechnology 20(6):700-707, Dec. 2009.
Farid, S.S., "Process Economics of Industrial Monoclonal Antibody Manufacture," Journal of Chromatography B 848(1):8-18, Mar. 2007.
Foecking, M.K., and H. Hofstetter, "Powerful and Versatile Enhancer-Promoter Unit for Mammalian Expression Vectors," Gene45(1):101-105, 1986.
Hoeksema, F., et al., "Placing the RPL32 Promoter Upstream of a Second Promoter Results in a Strongly Increased Number of Stably Transfected Mammalian Cell Lines That Display High Protein Expression Levels," Biotechnology Research International 11:492875, Nov. 2010, 11 pages.

(Continued)

*Primary Examiner* — Paul J Holland
(74) *Attorney, Agent, or Firm* — Christenser O'Connor Johnson Kindness PLLC

(57) ABSTRACT

The present invention provides an approach to enhancing the production of a foreign protein serving as a protein-based pharmaceutical product in host cells such as cultured cells derived from a mammal. The present invention provides transformed cells having a novel Hspa5 gene promoter, and a method for secreting and producing a foreign protein at high levels using the transformed host cells.

20 Claims, 30 Drawing Sheets

Specification includes a Sequence Listing.

(56) References Cited

OTHER PUBLICATIONS

Langmead, B., et al., "Ultrafast and Memory-Efficient Alignment of Short DNA Sequences to the Human Genome," Genome Biology 10(3):R25, 2009, 10 pages.
Luo, X., et al., "FOXM1 Promotes Invasion and Migration of Colorectal Cancer Cells Partially Dependent on HSPA5 Transactivation," Oncotarget 7(18):26480-26495, Mar. 2016.
Mortazavi, A., et al., "Mapping and Quantifying Mammalian Transcriptomes by RNA-Seq," Nature Methods 5(7):621-628, Jul. 2008.
Okumura, T., et al., "Efficient Enrichment of High-Producing Recombinant Chinese Hamster Ovary Cells for Monoclonal Antibody by Flow Cytometry," Journal of Bioscience and Bioengineering 120(3):340-346, 2015.
Running Deer, J., and D.S. Allison, "High-Level Expression of Proteins in Mammalian Cells Using Transcription Regulatory Sequences from the Chinese Hamster EF-1α Gene," Biotechnology Progress 20(3):1880-889, May-Jun. 2004.
Werner, R.G., "Economic Aspects of Commercial Manufacture of Biopharmaceutics," Journal of Biotechnology 113(1-3)1171-182, Sep. 2004.
Wurm, F.M., "Production of Reconbinant Protein Therapeutics in Cultivated Mammalian Cells," Nature Biotechnology 22(11):1393-1398, Nov. 2004.
International Preliminary Report on Patentability dated Apr. 9, 2019, issued in corresponding International Application No. PCT/JP2017/035773, filed Oct. 2, 2017, 16 pages.
International Search Report and Written Opinion dated Dec. 19, 2017, issued in corresponding International Application No. PCT/JP2017/035773, filed Oct. 2, 2017, 21 pages.
Extended European Search Report dated May 28, 2020, issued in European Application No. 17858330.8, 19 pages.
Kim, K.S., et al., "Expression of the Glucose-Regulated Proteins (GRP94 and GRP78) in Differentiated and Undifferentiated Mouse Embryonic Cells and the Use of the GRP78 Promoter as an Expression System in Embryonic Cells," Differentiation: Research in Biological Diversity 42(3):153-159, Feb. 1990.
"Mouse DNA Sequence From Clone RP23-446N16 on Chromosome 2," Database EMBL [Online], retrieved from EBI Accession No. EMBL:AL929106, Database Accession No. AL929106, Sep. 26, 2002, 15 pages.
Rattus norvegicus Clone CH230-43016, sequencing in progress; 7 unordered pieces, Database EMBL [Online], retrieved from EBI Accession No. EMBL:AC131419, Database Accession No. AC131419, Aug. 24, 2002, 15 pages.
Office Action issued in counterpart Chinese Application No. 201780060815.0 dated Dec. 31, 2021 (16 pages).
*Homo sapiens* heat shock 70kDa protein 5 (glucose-regulated protein, 78kDa) (HSPA5) gene, complete cds; NIEHS-SNPs; Environmental Genome Project; NIEHS ES15478; Department of Genome Sciences; Jan. 31, 2006; 7 pages.
FOXM1 promotes invasion and migration of colorectal cancer cells partially dependent on HSPA5 transactivation Oncotarget, Vo. 7, No. 18; Mar. 28, 2016; pp. 26480-26495.
Rat 78-Kdal glucose-related protein (GRP78), promoter region; NCBI GenBank Sequence ID: J03377.1; Apr. 27, 1993; 1 page.
Mus musculus 78 kDa glucose-regulated protein (grp78) gene, promoter region and partial cds; NCBI GenBank Sequence ID: U16277.1; May 25, 1995; 2 pages.
*H.spiens* BiP/GRP78 promoter; NCBI GenBank Sequence ID: X59969.1; May 30, 1996; 2 pages.

\* cited by examiner

SEQ ID NO: 1: Nucleotide sequence of polynucleotide which is Chinese hamster-derived Hspa5 promoter

```
TATAGCCCAGGCACACATGAACTTGTAATCCTCCTGCTTCAGCCTCTTCAGTAGCTGGGG
TTACAGGCCTACCACTAGGTGTGGCTCAGGTATCACTTTTTAAATGTTACAAAAATTGG
TGCAAGTACTTCATTAATCAAAAAACAGGCTGAAATTGAGTTTTGTATTTTAGTGGAAAT
AGACTGTGATACAGATGTGCTTGAAATGACATGAAGCTGTGATGTGGTCAAATAGTGATT
TTTTTCTTTCATTTCTTCTTCTTGTTCTTACTCTTTTTTCATATAGGGTTTCAATATGCA
GCTCTGGAACTATTTAGACCAGGATGGCCTTGAATTCAAGAGATCCCTCTGCTTCTGCCT
CCCTTGTGCTGAGATTAAAGTCATGAGCCACCATATCCGGCTGTAGTCTCCTTTAAAATT
CAAGCCAAAAGTATCTGCAAAGATGGTCGGTGGTTAAGAGCACTGGCTGCTCTTCATGG
GACCAGGGATTAAAGGCATGCAGCAGTAAACTGGGCTTAGTGACTTCTGTCTTCATACTG
GACTGGTACAGTCCCAAGGAAGATCAATGTTATGACAGTATTACAAGCCTTACTGAAAGT
GGTGTATGATGCAACATCTGTAGAAAGATGGTGTTGACTGAGTCACCAACATAACCTTT
GAGGAACAAGAAAGGAGAAATTCCTGAACAGTGACTCACAAGCTCACATTTTAGTGAACT
GTGTGTAATGTTCCAGTAGTATTCAGACAGTCTACTTATGAAGCTCAAGATACATTTAAT
GGGAATACTGGAGTCATTTCCTGCCCGTGACAACATCCTAAGCATCTCCTATAAGCATGT
ATATAAGTAAGCACATGGGAGGCAGAGACAGTAGATCTGAGAGCTCCATCCCAGGGGATG
GATATCAGTCAGTTGCCTAGCATGCACAGAATCTTGGGTCAAGTCCCAACTGGACACAGT
AATGTATGCCTATTAGTCCCAACACTTGGAAGGTATTGGCAGAAGGTTCAGGAGTTCAAA
GTCATCTGCTACAAAGTGTTGAGGCTAGCCTGGGTTACATGAGTCTCCATCTTTAAAAAA
AGAAAAAGTGGGGCTGGAAAGATGGCTCAGTGGTTAAGAGCACCGCCTGCTCTTCCAAA
GGTCCTGAGTTCAATTCCCAGCAACCACATGGTGGCTCAAAACCATCTGTAGTGAAATCT
GGTGCCCTCTGTGTACAAGATAAATGAATGAATCTTAAAAAAAAAAGTCAGTGGGTGGTG
GTGGCGCACACCTTTAGTCCCAGCACTCGGGAGAGGCAGGTGTGAGTTCGAGACCAGCCT
GGTCTACAAGAGCTACTTCCAGGACAAAGCCTCCAAAGCCACAGAGAAACCCTGTCTCGA
AAAACCAAACCAAACCAAAAAGTCAATAGCATAAGCTACAGATCAACCAGGTTA
TCAATTCTACCTGTACCACTCACCAGTGACTATTCTATTTAGCCACCCCCCCCCAATGA
TCTCTTCTGGAAAATGGGAAACATCTACCAAGAATTAATCAAAGGACTAAATGACACATG
CAAAAAAAAAAAACCTTAGAACAGTGTTTTAAGCAGGATAAGTAGTTCAAGACCAGTTT
GGACCATGTCTCAAAACTAAAGGAACAACGAAGTACATTTAGTATTTTTTGCAACATGTT
ATTATTACATAGCATCAGGAAGACAATTTTTTCTTTGTCTGCTAAATGCCTTTGTCATAT
CAGACCTATTTCAAGAGTCAGGATAGAATGGTGTCAAGAAGGGATGAGGAAGGACTTGTA
AATTATAACCAAGCCACAAATGAAAATGATAGACAAGGATCGGGAACATTATGGGCGAC
AAGCTAGAGAAAAAAAATGATATATTCCAGGGTGGAAAGTGCTCGCTTGACTATTCATAG
```

FIG. 12A

AACAGAATAGCCACAGCATAGCGGGGGGCTCAGTACTAGGTTGCAAATGGCCAGGCCAAT
TCTGGGACTTAACCCCAAGAAAAGAAAAATTGGCAAGGCCAGGATAGACAAATGCAGCTG
GCCTAGGGGTGAAGGGAAAACAGTTGGCTGAGAAGAGCCACGATTCGCAGAGAGGCAGAA
CACAGACTAGGACCCAGCTCGAGACGTGCAGGCCGGGTGGGTAACATAGAGCCCGGGCGC
TCGGCTACCCGAGAACGTGAGGGAGGCTTGGAAGGGCAGAGATGCGTTCCCAGGCGACCA
CAGCATCTATGCTGAGGCTGAGCAGCTCGGGACCCGAGGGGACTTAGGAGGAGAAAAGGC
CGCATACTGCTTCGGGGTAAGGGACAGACCGGGGAAGGACCCAAGTCCCACCGCCCAGAG
GGAACTGACACGCAGACCCGCAGCAGTCCCCGGGGGCCGGGTGACGGGAGGACCTGGAC
GGTTACCGGCGGAAACGGTCTCGGGTTGAGAGGTCACCTGAGGGACAGGCAGCTGCTGAA
CCAATAGGACCGGCGCACAGGGCGGATGCTGCCTCTCATTGGCGGCCGTTGAGAGTAACC
AGTAGCCAATGAGTCAGCCCGGGGGGCGTAGCGGTGACGTAAGTTGCGGAGGAGGCCGCT
TCGAATCGGCAGCGGCCAGCTTGGTGGCATGGACCAATCAGCGTCCTCCAACGAGAAGCG
CCTTCACCAATCGGAGGCCTCCACGACGGGGCTGGGGGGAGGGTATATAAGCCAAGTCGG
CGGCGGCGCGCTCCACACTGGCCAAGACAACAGTGACCGGAGGACCTGCCTTTGCGGCTC
CGAGAGGTAAGCGCCGCGGCCTGCTCTTGCCAGACCTCCTTTGAGCCTGTCTCGTGGCTC
CTCCTGACCCGGGGGGCTTCTGTCGCCCTCAGATCGGAACGCCGCCGCGCTCCGGGACTA
CAGCCTGTTGCTGGACTTCGAGACTGCAGACGGACCGACCGCTGAGCACTGGCCCACAGC
GCCGGCAAG

FIG. 12B

ACAGTAGGGAGGGGACTCAGAGCTGGAGGCAATTCCTTTGGCCGGGCTTGTCCTGCGACTTACC
GTGGGGCAGCGCAATGTGGAGAGGCCTGGTAAAATGGCTGGGCAAGGGTGCGGAGGGGACATAA
CTGGCAGGAAGGAGTCATGATTCGTGGTCGAACAGAGTCCAGACCAGCTCGACCTGTGAGCAAC
GAACGGCCCTGAGACTCGCATACCCCAATACCGGTAGTGGCCGTGAAGGGCAAAGAAATGTGTT
CTGAGGCGATCCCAGCATCTAAGCTGCGACTGGTCTACTCAGAGACTGGATGGAAGCTGGGAAG
AGAAAGCTGCTTCCCGCTTCGGGGTGAGGGATGGAGGAAGGGAGAACAAGCAGTAGAGAAGGAA
AAGTTTCAGATCCCACAGCCCCGGGGGGTCACTCCTGCTGGATCTACTCCGACCCCCTAGGGCC
GGGAGTGAAGGCGGGACTTGTGCGGTTACCAGCGGAAATGCCTCGGGGTCAGAAGTCGCAGGAG
AGATAGACAGCTGCTGAACCAATGGGACCAGCGGATGGGGCGGATGTTATCTACCATTGGTGAA
CGTTAGAAACGAATAGCAGCCAATGAATCAGCTGGGGGGGCGGAGCAGTGACGTTTATTGCGGA
GGGGGCCGCTTCGAATCGGCGGCGGCCAGCTTGGTGGCCTGGGCCAATGAACGGCCTCCAACGA
GCAGGGCCTTCACCAATCGGCGGCCTCCACGACGGGCTGGGGAGGGTATATAAGCCGAGTAG
GCGACGGTGAGGTCGACGCCGGCCAAGACAGCACAGACAGATTGACCTATTGGGGTGTTTCGCG
AGTGTGAGAGGGAAGCGCCGCGGCCTGTATTTCTAGACCTGCCCTTCGCCTGGTTCGTGGCGCC
TTGTGACCCCGGGCCCTGCCGCCTGCAAGTCGGAAATTGCGCTGTGCTCCTGCTACGGCCT
GTGGCTGGACTGCCTGCTGCTGCCCAACTGGCTGGCAAG

FIG. 13

SEQ ID NO: 3: Nucleotide sequence of polynucleotide which is mouse-derived Hspa5 promoter
ATGGTGGAAAGTGCTCGTTTGACCATAGTACTGAATCTCCGCGGCGGAGAAAGGGAATAGGTTA
CAATTGGCCAGGCCAATCCTGGGACTTAACCCTGGCAAAGGGAAGATTCGAAAGGCCTGGAAAG
ACACATACGGCTAGCCTTGGGGTGAAGGAGAAACACGGTTAGCTGAGAAGCACCAGGATTCTCA
GCGAGGCAGAATCCAGATCAGGCCCCAGCTCGAGACGTGCAGGCCGGGCGAGTAACAGGGCCTG
GACTCTGGGACATCCGAGAACGTGTGGAGGCTGGGGAGGGCGATCACAGCTGAGGCCGGGCAGC
TCAGGACGCGGGGAATCGAGGAGGAGAAAGGCCGCGTACTTCTTCAGAGTGAGAGACAGAAAAG
GAGACCCCGAGGGAACTGACACGCAGACCCCACTCCAGTCCCCGGGGGCCTGGCGTGAGGGGAG
GACCTGAACGGTTACCGGCGGAAACGGTCTCGGGGTGAGAGGTCACCCGAAGGACAGGCAGCTG
CTGAACCAATAGGACCAGCGCTCAGGGCGGATGCTGCCTCTCATTGGTGGCCGTTAAGAATGAC
CAGTAGCCAATGAGTCAGCCCGGGGGGCGTAGCAATGACGTGAGTTGCGGAGGAGGCCGCTTCG
AATCGGCAGCAGCCAGCTTGGTGGCATGGACCAATCAGCGGCCTCCAACGAGTAGCGACTTCAC
CAATCGGAGGCCTCCACGACGGGGCTGTGGGGAGGGTATATAAGGCGAGTCGGCGACGGCGCGC
TCGATACTGGCCGAGACAACACTGACCTGGACACTTGGGCTTCTGCGTGTGTGTGAGGTAAGCG
CCGCGGCCTGCTGCTAGGCCTGCTCCGAGTCTGCTTCGTGTCTCCTCCTGACCCCGAGGCCCCT
GTCGCCCTCAGACCAGAACCGTCGTCGCGTTTCGGGGCCACAGCCTGTTGCTGGACTCCTAAGA
CTCCTGCCTGACTGCTGAGCGACTGGTCCTCAGCGCCGGC

FIG. 14

SEQ ID NO: 4: Nucleotide sequence of polynucleotide which is rat-derived Hspa5 promoter CTCAACGGAGAAGGGCTCCGGACTAGGTTACAATTGGCCAGGCCAATCCTGGGACTTATCCCCG
GGAAAGGGAAAATCAGAAAGGCCCAGAAACATACATACAACTAGACTTGGGGTGAACGAGGAGC
ATGATTAGCTGAGAAGAGCCAGGATTCTCAGCGAGGCAGAACCCATACCAGGCCCCAGCCCGGG
ACATGCAGGCCCGTTGAGTAACAGGGCCTGGACGCTGGAACACCCGAGAAAAGTGCCGAGGCTG
GGAAGGGTGATCACAGCATCACAGCTGAGGCCGGGCAGCTGAAGACATGAGTGAATCTAGGAGA
AGAAAGGCAGCGTACTTCTTCCGAGTGAGAGACAGAAAGAGAGGACCCGAGTCTCACAGCCCTG
AGGGAACTGACACGCAGACCCCACTCCAGTCCCCGGGGGCCCAACGTGAGGGGAGGACCTGGAC
GGTTACCGGCGGAAACGGTTTCCAGGTGAGAGGTCACCCGAGGGACAGGCAGCTGCTCAACCAA
TAGGACCAGCTCTCAGGGCGGATGCTGCCTCTCATTGGCGGCCGTTAAGAATGACCAGTAGCCA
ATGAGTCGGCCTGGGGGGCGTACCAGTGACGTGAGTTGCGGAGGAGGCCGCTTCGAATCGGCAG
CGGCCAGCTTGGTGGCATGAACCAACCAGCGGCCTCCAACGAGTAGCGAGTTCACCAATCGGAG
GCCTCCACGACGGGGCTGCGGGGAGGATATATAAGCCGAGTCGGCGACCGGCGCGCTCGATACT
GGCTGTGACTACACTGACTTGGACACTTGGCCTTTTGCGGGTTTGAGAGGTAAGCGTCGCGGCC
TGCTTCCAGGCCTACCCTGATTTTGGTTCGTGGCTCCTCCTGACCCTGAGACCTCTGTCGCCCT
CAGATCAGAACCGTCGTCGCGTTTCGGGGCTACAGCCTGTTGCTGGACTCTGTGAGACACCTGA
CCGACCGCTGAGCGACTGACTGGTCCACAGCGCCGGCAAG

FIG. 15

PROMOTER OF HSPA5 GENE

TECHNICAL FIELD

The present invention relates to a method for producing a foreign protein using mammalian cells constructed by transfecting mammalian host cells with a foreign gene expression vector having a Hspa5 gene promoter.

BACKGROUND ART

The development of gene recombination techniques has rapidly expanded the market of protein-based pharmaceutical products such as therapeutic proteins and antibody drugs. Among them, antibody drugs do not cause adverse immune responses when administered to the human body and are under active development because of their high specificity.

Examples of hosts to produce the protein-based pharmaceutical products typified by antibody drugs can include microorganisms, yeasts, insects, animal and plant cells, and transgenic animals and plants. Posttranslational modification such as folding or sugar chain modification is essential for the physiological activity or antigenicity of the protein-based pharmaceutical products. Therefore, microorganisms which cannot perform complicated posttranslational modification, or plants which differ significantly in sugar chain structure from humans are not suitable as hosts. Cultured mammalian cells, such as CHO (Chinese hamster ovary) cells, are currently mainstream due to their having a sugar chain structure similar to that of humans and permitting posttranslational modification, and further in consideration of safety.

Use of cultured mammalian cells as a host presents problems such as low growth rates, low productivity and high cost as compared with microorganisms or the like (Non Patent Literature 1). Furthermore, clinical utilization of protein-based pharmaceutical products requires administering the pharmaceutical products at large doses. Therefore, a lack of sufficient production capacity thereof has been a global issue. In the case of producing a protein-based pharmaceutical product in a cultured mammalian cell expression system, reduction in production cost has been attempted by making improvements to each production step, because the production cost is higher than that of synthetic low-molecular weight pharmaceutical products. However, increasing the amount of protein produced in the cultured mammalian cell expression system is also a promising method for reduction in production cost (Non Patent Literature 2 and 3). Accordingly, in order to increase the productivity of foreign genes in cultured mammalian cells, many approaches such as promoters, enhancers, drug selection markers, gene amplification and culture engineering approaches have been practiced so far through trial and error. In the case of using CHO cells as host cells, a human cytomegalovirus major immediate early promoter (hereinafter, referred to as a CMV promoter) derived from a virus is generally used for the expression of foreign genes, i.e., the production of protein-based pharmaceutical products (Non Patent Literature 4, 5 and 6). It is also known that a polynucleotide upstream of the transcription start site of the gene (promoter region) of elongation factor-1 alpha (EF-1α) (Patent Literature 1 and Non Patent Literature 7) or a human ribosomal protein RPL32 or RPS11 can be used alone or in combination with an additional heterologous promoter in protein expression in CHO cells (Non Patent Literature 8 and Patent Literature 2). However, these promoters regulate the expression of their downstream foreign genes in response to the intracellular physiological conditions of the cultured mammalian cells serving as a host, and often exhibit the maximum activity in the logarithmic growth phase in which the cultured mammalian cells actively proliferate. Thus, the activity of such a promoter is often attenuated in the stationary phase after the cell density reaches its maximum level. Hence, there is a demand for the development of a promoter that permits strong expression of a foreign gene throughout the culture period of cultured mammalian cells.

CITATION LIST

Patent Literature

Patent Literature 1: Japanese Patent No. 3051411
Patent Literature 2: WO2013/080934

Non Patent Literature

Non Patent Literature 1: Florian M. Wurm., Nat. Biotechnol. 22 (11): 1393-1398, 2004
Non Patent Literature 2: Farid S S., J Chromatogr B Analyt Technol Biomed Life Sci. 848 (1): 8-18, 2007
Non Patent Literature 3: Werner R G. Economic aspects of commercial manufacture of biopharmaceuticals. J Biotechnol. 113 (1-3): 171-182, 2004
Non Patent Literature 4: Durocher Y et al., Curr Opin Biotechnol. 20 (6): 700-707, 2009
Non Patent Literature 5: Boshart M et al., Cell. 41 (2): 521-530, 1985
Non Patent Literature 6: Foecking M K et al., Gene. 45 (1): 101-105, 1986
Non Patent Literature 7: Deer J R. and Allison D S., Biotechnol. Prog. 20: 880-889, 2004
Non Patent Literature 8: Hoeksema F. et al., Biotechnology Research International, Volume 2011, Article ID 492875, 11 pages
Non Patent Literature 9: Okumura T et al., J Biosci Bioeng., 120 (3): 340-346, 2015
Non Patent Literature 10: Langmead B et al., Genome Biology. 10: 1186, 2009
Non Patent Literature 11: Mortazavi A et al., Nature Methods. 5: 621-628, 2008

SUMMARY OF INVENTION

Technical Problem

An object of the present invention is to provide an approach to enhancing the amount of a foreign protein, which serves as a protein-based pharmaceutical product, produced using a promoter having high foreign gene expression-enhancing activity in host cells such as cultured mammalian cells. If a promoter is found which has promoter activity comparable to or higher than that of a human EF-1α promoter in CHO cells or the like and maintains its high promoter activity for a long period from the logarithmic growth phase to the stationary phase of cultured mammalian cells, an approach to achieving the stable and high expression of a foreign gene in mammalian cells can be provided. Accordingly, an approach can be provided which contributes to increasing the amount of a protein-based pharmaceutical product produced in a cultured mammalian cell expression system, i.e., reduction in production cost.

Solution to Problem

The present inventors have conducted intensive studies directed towards achieving the aforementioned object. As a result, the inventors have found that a polynucleotide approximately 3 kbp upstream of the start codon of a heat-shock protein A5 (Hspa5/GRP78) gene has excellent promoter activity and is capable of markedly improving the productivity of a foreign protein to be expressed in cultured mammalian cells, thereby completing the present invention. Specifically, the present invention includes the following aspects of the invention.

(1) A polynucleotide consisting of the nucleotide sequence shown in SEQ ID NO: 1 or a partial sequence of the nucleotide sequence, the polynucleotide being a Chinese hamster derived Hspa5 gene promoter and comprising a polynucleotide consisting of the nucleotide sequence shown in SEQ ID NO: 9.

(2) The polynucleotide according to the above (1), which consists of the nucleotide sequence shown in SEQ ID NO: 1.

(3) The polynucleotide according to the above (1), which consists of the nucleotide sequence shown in SEQ ID NO: 5.

(4) The polynucleotide according to the above (1), which consists of the nucleotide sequence shown in SEQ ID NO: 6.

(5) The polynucleotide according to the above (1), which consists of the nucleotide sequence shown in SEQ ID NO: 7.

(6) The polynucleotide according to the above (1), which consists of the nucleotide sequence shown in SEQ ID NO: 8.

(7) The polynucleotide according to the above (1), which consists of the nucleotide sequence shown in SEQ ID NO: 9.

(8) A polynucleotide consisting of the nucleotide sequence shown in SEQ ID NO: 2 in the sequence listing, the polynucleotide being a human-derived Hspa5 gene promoter.

(9) A polynucleotide consisting of the nucleotide sequence shown in SEQ ID NO: 3 in the sequence listing, the polynucleotide being a mouse-derived Hspa5 gene promoter.

(10) A polynucleotide consisting of the nucleotide sequence shown in SEQ ID NO: 4 in the sequence listing, the polynucleotide being a rat-derived] Hspa5 gene promoter.

(11) A polynucleotide consisting of a nucleotide sequence having 95% or higher identity to the nucleotide sequence according to any one of the above (1) to (10), the polynucleotide having promoter activity.

(12) A polynucleotide consisting of a nucleotide sequence having 99% or higher identity to the nucleotide sequence according to any one of the above (1) to (10), the polynucleotide having promoter activity.

(13) A polynucleotide that hybridizes under stringent conditions to a polynucleotide consisting of a nucleotide sequence complementary to the nucleotide sequence according to any one of the above (1) to (12), the polynucleotide having promoter activity.

(14) A foreign gene expression unit comprising the polynucleotide according to any one of the above (1) to (13).

(15) The foreign gene expression unit according to the above (14), wherein the foreign gene is a gene encoding a multimeric protein.

(16) The foreign gene expression unit according to the above (14), wherein the foreign gene is a gene encoding a heteromultimeric protein.

(17) The foreign gene expression unit according to the above (14), wherein the foreign gene is a gene encoding an antibody or an antigen-binding fragment thereof.

(18) A foreign gene expression vector comprising the foreign gene expression unit according to any one of the above (14) to (17).

(19) A foreign gene expression vector comprising the foreign gene expression unit according to any one of the above (14) to (17) and any one or more polynucleotides selected from polynucleotides (a) to (e) of the following group A:

group A (a) a polynucleotide consisting of the nucleotide sequence shown in SEQ ID NO: 35 in the sequence listing, (b) a polynucleotide consisting of the nucleotide sequence shown in SEQ ID NO: 36 in the sequence listing, (c) a polynucleotide consisting of the nucleotide sequence shown in SEQ ID NO: 37 in the sequence listing, (d) a polynucleotide consisting of a nucleotide sequence having 95% or higher identity to the nucleotide sequence of any one of the polynucleotides (a) to (c), the polynucleotide having foreign gene expression-enhancing activity, and (e) a polynucleotide consisting of a nucleotide sequence having 99% or higher identity to the nucleotide sequence of any one of the polynucleotides (a) to (c), the polynucleotide having foreign gene expression-enhancing activity.

(20) A transformed cell into which the foreign gene expression vector according to the above (18) or (19) has been introduced.

(21) A transformed cell according to the above (20), wherein the cell is a cultured cell derived from a mammal.

(22) The transformed cell according to the above (21), wherein the cultured cell derived from a mammal is a COS-1 cell, a 293 cell, or a CHO cell.

(23) A method for producing a foreign gene-derived protein, comprising culturing the transformed cell according to any one of the above (20) to (22), and obtaining the foreign gene-derived protein from the culture.

(24) Use of the polynucleotide according to any one of the above (1) to (13) for the purpose of expressing a foreign gene in a transformed cell.

(25) Use of the foreign gene expression vector according to the above (18) or (19) for the purpose of expressing a foreign gene in a transformed cell.

Advantageous Effects of Invention

The method for producing a foreign protein according to the present invention is capable of markedly enhancing the expression of a foreign gene such as one encoding a therapeutic protein or an antibody. Furthermore, the combination of the promoter of the present invention with a DNA element can further enhance the expression of a foreign gene encoding a therapeutic protein, an antibody, or the like.

BRIEF DESCRIPTION OF DRAWINGS

FIG. 1A shows time-dependent change in the number of viable cells.

FIG. 1B shows time-dependent change in the amount of antibody produced.

FIG. 2A shows results for Jar #1. The top 20 genes having the highest expression level in the cells on the 4th day in Jar #1 were plotted.

FIG. 2B shows results for Jar #2. The top 20 genes having the highest expression level in the cells on the 4th day in Jar #1 were plotted.

FIG. 2C shows results for Jar #3. The top 20 genes having the highest expression level in the cells on the 4th day in Jar #1 were plotted.

FIG. 5A shows the number of viable cells on each day of sampling.

FIG. 5B shows the amount of the antibody produced on each day of sampling.

FIG. 5C shows the amount of antibody produced per cell and per day on each day of sampling.

FIG. 7A shows the number of viable cells on each day of sampling.

FIG. 7B shows the amount of luminescence of the *Renilla* luciferase per $10^3$ cells on each day of sampling.

FIG. 8A shows the number of viable cells on each day of sampling.

FIG. 8B shows the amount of antibody produced on each day of sampling.

FIG. 8C shows the amount of antibody produced per cell and per day on each day of sampling.

FIG. 9A shows the number of viable cells on each day of sampling.

FIG. 9B shows the amount of antibody produced on each day of sampling.

FIG. 9C shows the amount of antibody produced per cell and per day on each day of sampling.

FIG. 10A shows the number of viable cells on each day of sampling. ch 1.1 kb and ch 0.6 kb depict results from the fed-batch culture of the stable pool obtained using 1.1 kbp and 0.6 kbp partial sequences, respectively, of a Chinese hamster Hspa5 gene promoter as a promoter for antibody expression.

FIG. 10B shows the amount of antibody produced on each day of sampling. ch 1.1 kb and ch 0.6 kb depict results from the fed-batch culture of the stable pool obtained using 1.1 kbp and 0.6 kbp partial sequences, respectively, of a Chinese hamster Hspa5 gene promoter as a promoter for antibody expression.

FIG. 10C shows the amount of antibody produced per cell and per day on each day of sampling. ch 1.1 kb and ch 0.6 kb depict results from the fed-batch culture of the stable pool obtained using 1.1 kbp and 0.6 kbp partial sequences, respectively, of a Chinese hamster Hspa5 gene promoter as a promoter for antibody expression.

FIG. 11A shows the number of viable cells on each day of sampling.

FIG. 11B shows the amount of antibody produced on each day of sampling.

FIG. 11C shows the amount of antibody produced per cell and per day on each day of sampling.

FIG. 12A shows the nucleotide sequence of a polynucleotide which is a Chinese hamster derived Hspa5 gene promoter (continued in FIG. 12B).

FIG. 12B shows the nucleotide sequence of the polynucleotide which is a Chinese hamster Hspa5 gene promoter.

FIG. 13 shows the nucleotide sequence of a polynucleotide which is a human derived Hspa5 gene promoter.

FIG. 14 shows the nucleotide sequence of a polynucleotide which is a mouse derived Hspa5 gene promoter.

FIG. 15 shows the nucleotide sequence of a polynucleotide which is a rat derived Hspa5 gene promoter.

DESCRIPTION OF EMBODIMENTS

Figure 1A:
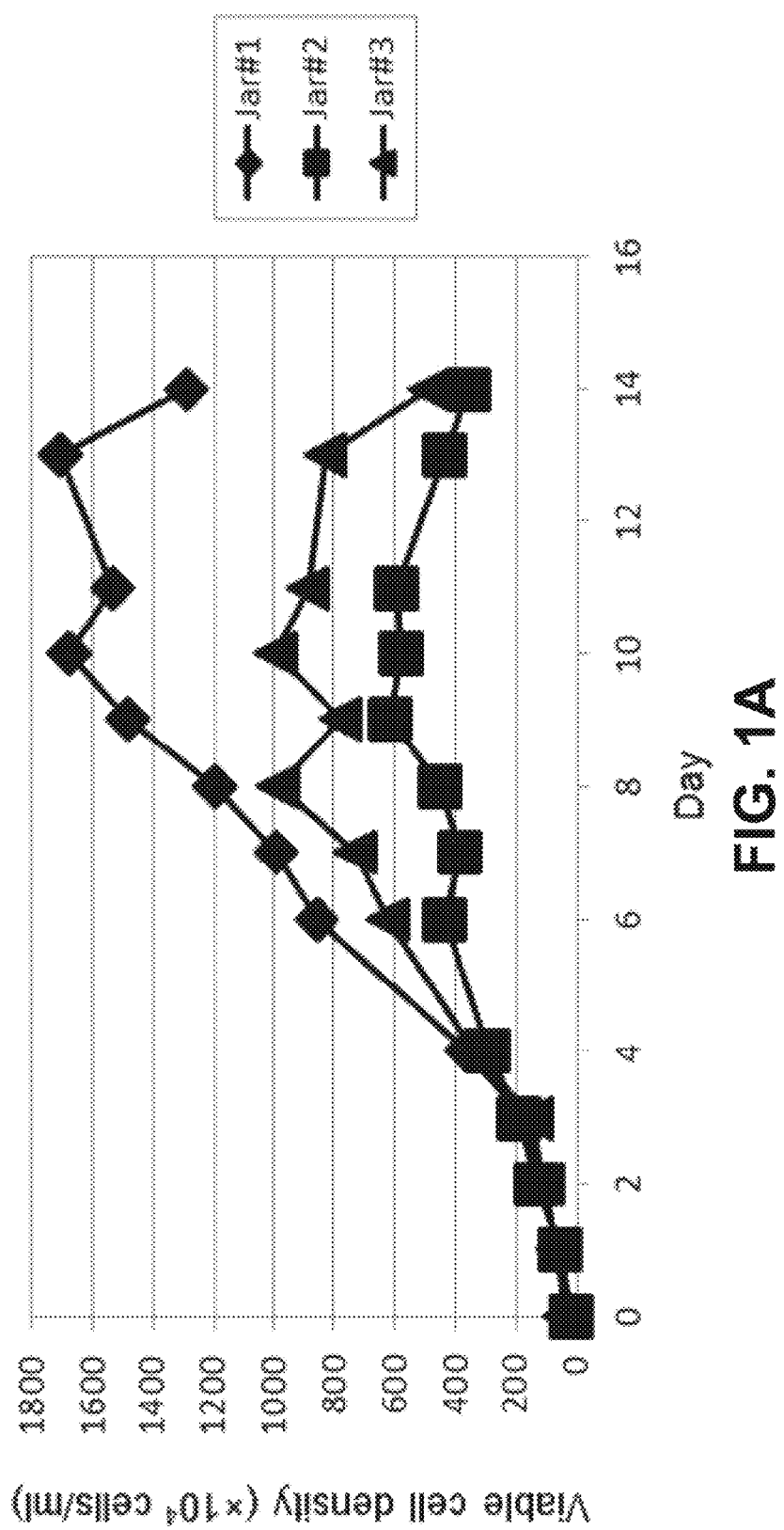
FIG. 1A Results of fed-batch culture of humanized antibody X-expressing cell lines X #1 and X #2 using a 1 L jar are shown.

Hereinafter, the present invention will be specifically described.

In the present description, the term "gene" means a moiety that is transcribed into mRNA and translated into a protein, and is used to include, not only DNA but also its mRNA and cDNA, and the RNA thereof.

In the present description, the term "polynucleotide" is used to have the same meaning as that of a nucleic acid, and includes DNA, RNA, a probe, an oligonucleotide, and a primer.

In the present description, the term "polypeptide" is used without being distinguished from the term "protein".

In the present description, the term "gene expression" means a phenomenon in which a gene is transcribed into mRNA, and/or a phenomenon in which the mRNA is translated into a protein.

In the present description, the term "foreign gene" means a gene that is artificially introduced into host cells.

In the present description, the term "foreign protein" means a protein encoded by the foreign gene.

In the present description, the term "gene expression unit" means a polynucleotide having at least a promoter region, a foreign gene, and a transcriptional terminator region (polyA addition signal) in the reading frame direction of transcription.

In the present description, the term "promoter" means a region to which a transcription factor involved in the start of transcription of DNA into RNA binds. In the present description, the term "promoter region" is also used. Examples of the promoter can include a polynucleotide from a nucleotide approximately 3 kbp upstream of a start codon to a nucleotide immediately upstream of a nucleotide sequence corresponding to the start codon. The promoter may contain 5'UTR and an intron.

In the present description, the term "promoter activity" refers to activity by which transcription starts through the binding of a transcription factor to the promoter to perform the production of a protein encoded by the gene. Promoter activity can be examined by using, as an indicator, the activity of a protein encoded by a reporter gene, such as firefly luciferase.

In the present description, the phrase "to have promoter activity" means that an antibody expression level equivalent to or higher than that of a human EF-1α gene promoter is exhibited under conditions similar to those for the evaluation of promoter activity with antibody expression level as an indicator in fed-batch culture described in (Example 5) mentioned later.

In the present description, the term "DNA element" means a polynucleotide having foreign gene expression-enhancing activity when located in proximity to a gene expression unit or in a foreign gene expression vector comprising the gene expression unit.

In the present description, the term "antigen-binding fragment of the antibody" means a partial fragment of the antibody having binding activity to the antigen. Examples thereof include Fab and F(ab')$_2$, though the antigen-binding fragment is not limited to these molecules as long as it has antigen-binding ability.

In the present description, the term "identity" refers to the relationship between sequences as to two or more nucleotide sequences or amino acid sequences and is determined by the comparison of the sequences, as known in the art. The term "identity" in the art also means, in some cases, the degree of sequence relevance between nucleic acid molecules or between polypeptides when determined depending on the agreement between two or more nucleotide sequences or between two or more amino acid sequences in a row. The term "identity" can be evaluated by calculating percent identity between a smaller sequence of two or more sequences and gap alignment (if present) addressed by a particular mathematical model or computer program (i.e., "algorithm"). Specifically, the identity can be evaluated using software such as ClustalW2 provided by European Molecular Biology Laboratory-European Bioinformatics Institute (EMBL-EBI), though the evaluation method is not limited thereto as long as the method is used by a person skilled in the art.

In the present description, the phrase "to hybridize under stringent conditions" refers to hybridization under conditions in which a so-called specific hybrid is formed whereas a non-specific hybrid is not formed. Examples thereof can include conditions under which a complementary strand of a nucleic acid consisting of a nucleotide sequence having 80% or higher, preferably 90% or higher, more preferably 95% or higher, most preferably 99% or higher identity to a nucleic acid hybridizes whereas a complementary strand of a nucleic acid consisting of a nucleotide sequence having lower identity does not hybridize. More specifically, the phrase is used to mean that hybridization is carried out in the commercially available hybridization solution ExpressHyb Hybridization Solution (manufactured by Clontech) at 68° C., or that hybridization is carried out under conditions in which hybridization is carried out using a DNA-immobilized filter in the presence of 0.7 to 1.0 M NaCl at 68° C., and the resultant is then washed at 68° C. with a 0.1× to 2×SSC solution (wherein 1×SSC consists of 150 mM NaCl and 15 mM sodium citrate), or conditions equivalent thereto.

1. Promoter for Use in Enhancement of Foreign Gene Expression

The foreign promoter for use in the method for producing a foreign gene-derived protein according to the present invention is a promoter of a heat-shock protein A5 gene (hereinafter, referred to as "Hspa5"). The promoter is not particularly limited as long as the promoter is a polynucleotide having activity as a Hspa5 promoter. The Hspa5 promoter is preferably a polynucleotide from a nucleotide approximately 3 kbp upstream of a start codon to a nucleotide immediately upstream of a nucleotide sequence corresponding to the start codon.

The origin of the Hspa5 promoter is not particularly limited and may be of mammalian origin. Examples thereof can include Chinese hamster, human, mouse, and rat derived Hspa5 promoters.

The promoter for use in the method for producing a foreign gene-derived protein according to the present invention is preferably a Chinese hamster Hspa5 promoter, more preferably the polynucleotide shown in SEQ ID NO: 1 in the sequence listing and FIG. 12. The nucleotide sequence of SEQ ID NO: 1 is a sequence from a nucleotide approximately 3 kbp upstream of the start codon of Chinese hamster-derived Hspa5 to the nucleotide immediately upstream of the nucleotide sequence corresponding to the start codon. The nucleotide sequences of SEQ ID NOs: 2, 3, and 4 are sequences from a nucleotide approximately 1 kbp upstream of the start codon of human-derived Hspa5, mouse-derived Hspa5, and rat-derived Hspa5, respectively, to the nucleotide immediately upstream of the nucleotide sequence corresponding to the start codon. The nucleotide sequences of SEQ ID NOs: 2, 3, and 4 are also shown in FIGS. 13, 14, and 15, respectively.

The Chinese hamster-derived Hspa5 promoter may have a nucleotide sequence consisting of a partial sequence of the sequence shown in SEQ ID NO: 1. Examples thereof include polynucleotides comprising the sequences shown in SEQ ID NOs: 5, 6, 7, 8 and 9, which are sequences from a nucleotide approximately 2.5, 2.0, 1.5, 1.1 and 0.6 kbp, respectively, upstream of the start codon of Hspa5 to the nucleotide immediately upstream of the nucleotide sequence corresponding to the start codon. The polynucleotides shown in SEQ ID NOs: 7, 8 and 9 are preferred, and the polynucleotides shown in SEQ ID NOs: 8 and 9 are more preferred.

The promoter for use in the method for producing a foreign gene-derived protein according to the present invention may be a polynucleotide consisting of a nucleotide sequence having 80% or higher, preferably 90% or higher, more preferably 95% or higher, most preferably 99% or higher identity to the nucleotide sequence shown in any one of SEQ ID NOs: 1 to 9, and having promoter activity.

The promoter for use in the method for producing a foreign gene-derived protein according to the present invention may be a polynucleotide that hybridizes under stringent conditions to a polynucleotide consisting of a nucleotide sequence complementary to a polynucleotide consisting of any one nucleotide sequence selected from the group consisting of the nucleotide sequences shown in SEQ ID NOs: 1 to 9, and having promoter activity.

The promoter for use in the method for producing a foreign gene-derived protein according to the present invention may be a mutant polynucleotide consisting of a nucleotide sequence comprising a deletion, substitution, and/or addition of one or more, preferably 1 to 300, more preferably 1 to 30 nucleotides in any one nucleotide sequence selected from the group consisting of the nucleotide sequences shown in SEQ ID NOs: 1 to 9, and having promoter activity.

The introduction of a mutation (deletion, substitution, and/or addition) into the nucleotide sequence can be performed by an approach known in the art such as the Kunkel method or the gapped duplex method, or a method equivalent thereto. For example, a kit for mutation introduction which exploits site-directed mutagenesis (e.g., Mutant-K (manufactured by Takara Bio Inc.) or Mutant-G (manufactured by Takara Bio Inc.)), or LA PCR in vitro Mutagenesis series kit from Takara Bio Inc. can be utilized. Such a mutant polynucleotide can also be used as the promoter of the present invention.

The foreign gene expression-enhancing activity possessed by the promoter of the present invention can be examined by using, as an indicator, the activity of a protein encoded by a reporter gene, such as firefly luciferase, or the amount of an antibody produced in fed-batch culture. When the amount of the antibody produced in fed-batch culture is equivalent or higher, preferably 1.2 or more times, more preferably 1.5 or more times higher by use of the promoter of the present invention compared with use of a human EF-1α promoter, it can be determined that this promoter has foreign gene expression-enhancing activity. Even in cases where the amount of an antibody produced in Fed-batch culture is increased by approximately 1.2-fold or more, a reduction of cell culture scale, culture time and the number of purification steps is expected. As a result, an improvement in yield and a reduction in culture cost are attained. The improved yield permits stable supply of a foreign protein as a medicament. Also, the reduced culture cost leads to a reduction in the prime cost of a foreign protein as a medicament.

2. Foreign Gene Expression Unit

The foreign gene expression unit for use in the method for producing a foreign gene-derived protein according to the present invention (hereinafter, also referred to as the "gene expression unit of the present invention") has at least the promoter of the present invention described in the preceding section 1., a foreign gene, and a transcriptional terminator region (polyA addition signal) in the reading frame direction of transcription.

The polyA addition sequence can be any sequence having the activity of terminating transcription from the promoter, and may be derived from a gene which is the same as or different from the gene of the promoter.

3. DNA Element for Use in Enhancing Foreign Gene Expression

Combined use of the gene expression unit of the present invention described in the preceding section 2. with a DNA element can further enhance the expression of a foreign gene. The DNA element for combined use can be obtained by interaction with acetylated histone H3 as an indicator. In general, the acetylation of histone (H3, H4) is reportedly involved in the activation of transcription on the basis of two main hypotheses: that conformational change of the nucleosome is involved such that histone tail acetylation neutralizes the charge thereof to loosen the binding between the DNA and the histone (Mellor J. (2006) Dynamic nucleosomes and gene transcription. Trends Genet. 22 (6): 320-329); and that the acetylation is involved in the recruitment of various transcription factors (Nakatani Y. (2001) Histone acetylases—versatile players. Genes Cells. 6 (2): 79-86). Both of the hypotheses strongly suggest that the acetylation of histone is involved in transcriptional activation. Thus, chromatin immunoprecipitation (ChIP) using an anti-acetylated histone H3 antibody is capable of enriching a sample for a DNA element that interacts with acetylated histone H3.

Examples of the DNA element for use in the enhancing of foreign gene expression in combination with the promoter of the present invention can include A2, A7, and A18.

A2 is positioned at a site from 80966429 to 80974878 of human chromosome 15 and is an 8450 bp polynucleotide having an AT content of 62.2%. The nucleotide sequence of A2 is shown in SEQ ID NO: 35 in the sequence listing.

A7 is positioned at a site from 88992123 to 89000542 of human chromosome 11 and is an 8420 bp polynucleotide having an AT content of 64.52%. The nucleotide sequence of A7 is shown in SEQ ID NO: 36 in the sequence listing.

A18 is positioned at a site from 111275976 to 111284450 of human chromosome 4 and is an 8475 bp polynucleotide having an AT content of 62.54%. The nucleotide sequence of A18 is shown in SEQ ID NO: 37 in the sequence listing.

The foreign gene expression-enhancing activity possessed by the DNA element for combined use with the promoter of the present invention can be examined by using, as an indicator, the activity of a protein encoded by a reporter gene, such as SEAP.

For combined use with the promoter of the present invention, any one of the DNA elements described above may be used alone, or two or more copies of one DNA element may be used. Alternatively, two or more DNA elements may be used in combination.

The DNA element used in the present invention may consist of a nucleotide sequence having 80% or higher, preferably 90% or higher, more preferably 95% or higher, most preferably 99% or higher identity to the nucleotide sequence shown in any of SEQ ID NOs: 35 to 37, and having foreign gene expression-enhancing activity. A homology search of the nucleotide sequence can be performed using, for example, a program such as FASTA or BLAST and the DNA Databank of JAPAN as the subject of the search.

A person skilled in the art can readily obtain such a homolog gene of the DNA element of the present invention with reference to Molecular Cloning (Sambrook, J. et al., Molecular Cloning: a Laboratory Manual 2nd ed., Cold Spring Harbor Laboratory Press, 10 Skyline Drive Plainview, N.Y. (1989)), etc. Likewise, the identity of the nucleotide sequence described above can be determined by FASTA search or BLAST search.

The introduction of a mutation (deletion, substitution, and/or addition) into the polynucleotide can be performed by an approach known in the art such as the Kunkel method or the gapped duplex method, or a method equivalent thereto. For example, a kit for mutation introduction (e.g., Mutant-K (manufactured by Takara Bio Inc.) or Mutant-G (manufactured by Takara Bio Inc.), or LA PCR in vitro Mutagenesis series kit from Takara Bio Inc. can be utilized which exploits site-directed mutagenesis. Such a mutant polynucleotide can also be used as the DNA element of the present invention.

4. Obtaining the Polynucleotide

In the present invention, a polynucleotide comprising a foreign gene encoding a foreign protein whose production is to be enhanced as mentioned later can be obtained by a general method given below. The polynucleotide can be isolated, for example, by screening a cDNA library derived from cells or tissues expressing the foreign gene, using a DNA probe synthesized on the basis of the gene fragment. mRNA can be prepared by an approach usually used in the art. For example, the cells or the tissues are treated with a guanidine reagent, a phenol reagent, or the like to obtain total RNA. Then, poly(A)+RNA (mRNA) is obtained therefrom by the affinity column method using an oligo(dT) cellulose column, polyU-Sepharose with Sepharose 2B as a carrier, or the like, or by the batch method. The poly(A)+ RNA may be further fractionated by the sucrose density gradient centrifugation method or the like. Subsequently, single-stranded cDNA is synthesized with the obtained mRNA as a template using an oligo dT primer and reverse transcriptase. Double-stranded cDNA is synthesized from the single-stranded cDNA using DNA synthetase I, DNA ligase and RNase H, etc. The synthesized double-stranded cDNA is blunt-ended with T4 DNA synthetase, then subjected to the linkage of an adaptor (e.g., an EcoRI adaptor), phosphorylation, etc., and incorporated into a λ phage such as λgt11 for in vivo packaging to prepare a cDNA library. Alternatively, the cDNA library may be prepared using a plasmid vector instead of the λ phage. Then, a clone having the DNA of interest (positive clone) can be selected from the cDNA library.

In the case of isolating a polynucleotide comprising the promoter and a terminator region, the DNA element, or a polynucleotide comprising a foreign gene for use in protein production from genomic DNA, the genomic DNA is extracted from a cell line of an organism serving as a source, followed by polynucleotide selection, according to a general approach (Molecular Cloning (1989) and Methods in Enzymology 194 (1991)). The extraction of the genomic DNA can be performed according to, for example, the method of Cryer et al. (Methods in Cell Biology, 12, 39-44 (1975)) and the method of P. Philippsen et al. (Methods Enzymol., 194, 169-182 (1991)).

The obtaining of the polynucleotide of interest comprising the promoter, the DNA element, or a foreign gene can also be performed by, for example, PCR (PCR Technology. Henry A. Erlich, Atockton press (1989)). The amplification of the polynucleotide by PCR employs 20 to 30 mer synthetic single-stranded DNA as a primer and genomic DNA as a template. The amplified gene is used after its polynucleotide sequence is confirmed. A genomic DNA library such as a bacterial artificial chromosome (BAC) library may be used as a template for PCR.

On the other hand, a polynucleotide comprising a foreign gene having an unknown sequence can be obtained by (a) preparing a gene library according to a common method, (b) selecting the desired polynucleotide from the prepared gene library, and amplifying the polynucleotide. The gene library can be prepared by partially digesting chromosomal DNA obtained by a common method from a cell line of an organism serving as a source, with an appropriate restriction enzyme to prepare fragments, ligating the obtained fragments to an appropriate vector, and introducing the vector into an appropriate host. Alternatively, the gene library may be prepared by extracting mRNA from the cells, synthesizing cDNA therefrom, then ligating the cDNA to an appropriate vector, and introducing the vector into an appropriate host. In this respect, a plasmid known as a well known vector for gene library preparation can be used as the vector, and a phage vector or a cosmid, etc. can also be widely used. The host to be transformed or transduced can be used according to the type of vector. The polynucleotide comprising a foreign gene is selected from the gene library by colony hybridization, plaque hybridization, or the like using a labeled probe comprising a sequence unique to the foreign gene.

The polynucleotide comprising a foreign gene can also be synthesized entirely chemically. The gene can be synthesized by, for example, a method of preparing one pair of complementary oligonucleotides and annealing these, a method of ligating several annealed DNAs using DNA ligase, or a method of preparing several partially complementary oligonucleotides and filling gaps therein by PCR.

The polynucleotide sequence can be determined by a usual method, for example, the dideoxy method (Sanger et al., Proc. Natl. Acad. Sci., USA, 74, 5463-5467 (1977)). Alternatively, the polynucleotide sequence may be readily determined using a commercially available sequencing kit or the like.

5. Foreign Gene Expression Vector

A vector comprising the foreign gene expression unit described in the preceding section 2. comprising the promoter described in the preceding section 1. is provided as a foreign gene expression vector for use in the method for producing a foreign gene-derived protein according to the present invention. The foreign gene expression vector for use in the method for producing a foreign gene-derived protein according to the present invention may comprise one of the DNA elements described in the preceding section 3., two or more copies of one DNA element, or a combination of two or more DNA elements. When a foreign gene is expressed in host cells using the foreign gene expression vector, the DNA element may be located immediately preceding or immediately following the gene expression unit, or may be located at a position distant from the gene expression unit. Alternatively, one foreign gene expression vector comprising a plurality of DNA elements may be used. The orientation of the DNA element may be either the forward direction or the reverse direction with respect to the gene expression unit.

Examples of the foreign gene can include, but are not particularly limited to: reporter genes such as secreted alkaline phosphatase (SEAP) gene, green fluorescence protein (GFP) gene, and luciferase gene; various enzyme genes such as α-amylase gene and α-galactosidase gene; genes of various interferons such as interferon α and interferon γ, which are pharmaceutically useful physiologically active proteins; genes of various interleukins such as IL1 and IL2; various cytokine genes such as erythropoietin (EPO) gene and granulocyte colony-stimulating factor (G-CSF) gene; growth factor genes; and a gene encoding a multimeric protein, for example, a gene encoding a heteromultimer which is an antibody or an antigen-binding fragment thereof. These genes may be obtained by any approach.

The term "antigen-binding fragment of the antibody" means a partial fragment of the antibody having binding activity to the antigen. Examples thereof include Fab, $F(ab')_2$, Fv, scFv, diabody, linear antibodies, and multispecific antibodies formed from antibody fragments. Also, Fab', which is a monovalent fragment of antibody variable regions obtained by the treatment of $F(ab')_2$ under reductive conditions is included in the antigen-binding fragment of the antibody. However, the antigen-binding fragment is not limited to these molecules as long as it has antigen-binding ability. Furthermore, these antigen-binding fragments also include, not only a fragment obtained by the treatment of the full-length molecule of an antibody protein with an appropriate enzyme but also a protein produced in appropriate host cells using a genetically engineered antibody gene.

The foreign gene expression vector for use in the method for producing a foreign gene-derived protein according to the present invention can comprise a selection marker for selecting a transformant. The transformant can be selected using, for example, a drug resistance marker which confers resistance to a drug such as cerulenin, aureobasidin, zeocin, canavanine, cycloheximide, hygromycin, puromycin, blasticidin, tetracycline, kanamycin, ampicillin, or neomycin. Alternatively, the transformant may be selected by using, as a marker, a gene that confers, for example, solvent resistance to ethanol or the like, osmotic pressure resistance to glycerol, a salt, or the like, or metal ion resistance to copper or the like.

The foreign gene expression vector for use in the method for producing a foreign gene-derived protein according to the present invention may be a vector that is not integrated into chromosomal DNA. In general, the foreign gene expression vector is randomly integrated into the chromosome after transfection of host cells. By contrast, use of a constituent derived from a mammalian virus such as simian virus 40 (SV40), papillomavirus (BPV, HPV), or EBV allows the foreign gene expression vector to be used as an episomal vector capable of replicating autonomously in the transfected host cells. For example, a vector having a sequence encoding a SV40-derived replication origin and a trans-acting factor SV40 large T antigen, or a vector having a sequence encoding EBV-derived oriP and EBNA-1 is widely used. The DNA element is capable of exhibiting foreign gene expression-enhancing activity, regardless of the type of vector or the presence or absence of integration into the chromosome.

6. Transformed Cells

The transformed cells for use in the method for producing a foreign gene-derived protein according to the present invention are transformed cells comprising the foreign gene expression vector of the preceding section 5. introduced thereinto.

The host cells to be transformed are eukaryotic cells, preferably mammalian cells, more preferably human-, mouse-, rat-, hamster-, monkey-, or bovine-derived cells. Examples of the mammalian cells can include, but are not limited to, COS-1 cells, 293 cells, and CHO cells (CHO-K1, DG44, CHO dhfr-, CHO-S).

In the present invention, the method for introducing the expression vector into host cells can be any method as long as the method allows the introduced gene to be present stably in the host and to be appropriately expressed. Examples thereof can include methods generally used, for example, the calcium phosphate method (Ito et al., (1984) Agric. Biol. Chem., 48, 341), electroporation (Becker, D. M. et al. (1990) Methods. Enzymol., 194, 182-187), the spheroplast method (Creggh et al., Mol. Cell. Biol., 5, 3376 (1985)), the lithium acetate method (Itoh, H. (1983) J. Bacteriol. 153, 163-168), and lipofection.

7. Method for Producing Foreign Protein

The method for producing a foreign protein according to the present invention can be performed by culturing the transformed cells described in the preceding section 6. by a known method, and collecting the foreign protein from the culture, followed by purification. The "culture" means any of a culture supernatant, cultured cells, and a cell homogenate. Not only a monomeric protein but also a multimeric protein may be selected as the foreign protein that can be produced using the transformed cells described in section 6. In the case of producing a heteromultimeric protein constituted by a plurality of different subunits, a plurality of genes encoding these subunits each need to be introduced into the host cells described in section 6.

The method for culturing the transformed cells can be performed according to a usual method for use in the culture of the host cells.

When the transformed cells are mammalian cells, the transformed cells are cultured, for example, at 37° C. under 5% or 8% $CO_2$ conditions for a culture time on the order of 24 to 1000 hours. The culture can be carried out by, for example, static culture, shake culture, stirring culture, batch culture under aeration, fed-batch culture, perfusion culture or continuous culture.

The expression product of the foreign protein gene from the culture (culture solution) described above can be confirmed by SDS-PAGE, Western blotting, ELISA, or the like.

8. Method for Producing Antibody Protein

Examples of the heteromultimeric protein to be produced using the production method described in the preceding section 7. can include antibody proteins. The antibody protein is a tetramer protein consisting of two molecules of a heavy chain polypeptide and two molecules of a light chain polypeptide. Thus, for obtaining an antibody protein in a form that maintains antigen-binding ability, it is necessary to introduce both heavy chain and light chain genes into the transformed cells described in the preceding section 6. In this case, heavy chain and light chain gene expression units may be present on the same expression vector or may be present on different expression vectors.

Examples of the antibody to be produced according to the present invention can include antibodies prepared by immunizing laboratory animals such as rabbits, mice, and rats with the desired antigen. Further examples of the antibody to be produced according to the present invention can include chimeric antibodies and humanized antibodies originating from the antibodies described above. In addition, a human antibody obtained from a genetically engineered animal or by the phage display method is also an antibody to be produced according to the present invention.

The antibody gene for use in antibody production is not limited to an antibody gene having a particular polynucleotide sequence as long as a combination of a heavy chain polypeptide and a light chain polypeptide obtained by the transcription of the antibody gene and subsequent translation retains the activity of binding to an arbitrary antigen protein.

The antibody gene is not necessarily required to encode the full-length molecule of the antibody. A gene encoding an antigen-binding fragment of the antibody can be used. The gene encoding such an antigen-binding fragment can be obtained by genetically engineering a gene encoding the full-length molecule of the antibody protein.

9. Methods for Producing Other Foreign Proteins

Examples of the foreign protein to be produced by the production method of the present invention can include the antibodies mentioned above as well as various human- or non-human animal-derived proteins, antigen-binding fragments thereof, and modified forms of the proteins or the fragments. Examples of such a protein and the like can include, but are not limited to: peptide hormones such as atrial natriuretic peptide (ANP), brain natriuretic peptide (BNP), C-type natriuretic peptide (CNP), vasopressin, somatostatin, growth hormone (GH), insulin, oxytocin, ghrelin, leptin, adiponectin, renin, calcitonin, osteoprotegerin, and insulin-like growth factor (IGF); cytokines such as interleukin, chemokine, interferon, tumor necrosis factor (TNFα/β as well as TNF superfamily, etc.), nerve growth factor (NGF), cell growth factor (EGF, FGF, PDGF, HGF, TGF, etc.), hematopoietic factor (CSF, G-CSF, erythropoietin, etc.), and adiponectin; receptors such as TNF receptor; enzymes such as lysozyme, protease, proteinase, and peptidase; functional fragments thereof (fragments partially or wholly retaining the biological activity of the original protein); and fusion proteins comprising these proteins.

EXAMPLES

Hereinafter, the present invention will be specifically described with reference to Examples. However, these Examples do not limit the technical scope of the present invention by any means. Plasmids, restriction enzymes, DNA-modifying enzymes, etc. used in Examples of the present invention are commercially available and can be used according to common methods. Operations used in DNA cloning, polynucleotide sequencing, transformation of host cells, culture of transformed cells, collection of a protein from the resulting culture, purification, etc. are also well known to a person skilled in the art or can be derived from the literature.

(Example 1) Construction of Humanized Antibody X-Expressing Cell Line 1-1) Construction of Humanized Antibody Gene X Expression Vector Humanized antibody gene X expression vector pDSLH4.1-X having pDSLH4.1 described in Non Patent Literature 9 as a vector backbone was constructed.

1-2) Generation of Humanized Antibody X-Expressing Stable Pool

CHO-K1 cells (ATCC) were adapted to suspension culture in a serum-free suspension culture condition, to obtain CHO-O1 cells as host cells. The CHO-O1 cells were transfected with the humanized antibody gene X expression vector pDSLH4.1-X constructed in (1-1) using a transfection apparatus Neon Transfection System (Invitrogen), and cultured in 5% $CO_2$ at 37° C. in a T25 flask. One day after the transfection, Geneticin (Life Technologies Corporation) was added thereto at a final concentration of 800 µg/mL, followed by drug selection culture for 1 week. Then, the cells were cultured in 5% $CO_2$ at 37° C. in a 125 mL Erlenmeyer flask to obtain a humanized antibody X-expressing stable pool.

1-3) Construction of Humanized Antibody X-Expressing Cell Line

The humanized antibody X-expressing stable pool generated in (1-2) was monocloned to obtain humanized antibody X-expressing cell lines X #1 and X #2.

Specifically, the humanized antibody X-expressing stable pool generated in (1-2) was suspended in a soft agar medium, seeded onto a 6-well plate, and cultured in 5% $CO_2$ at 37° C. After the culturing, a colony highly expressing humanized antibody X was picked onto a 96-well plate using ClonePix 2 (Genetix). The colony thus picked was subcultured by successive cell expansion steps to a 24-well plate, a 6-well plate, a T25 flask, and a 125 mL Erlenmeyer flask in that order, to obtain humanized antibody X-expressing cell lines X #1 and X #2.

(Example 2) Transcriptome Analysis of Humanized Antibody X-Expressing Cell Lines X #1 and X #2

Fed-batch culture was performed using the humanized antibody X-expressing cell lines X #1 and X #2 generated in Example 1. Transcriptome analysis was conducted on the time-dependent samples thereof to identify a highly expressed gene.

2-1) Fed-Batch Culture of Humanized Antibody X-Expressing Cell Lines X #1 and X #2

Each humanized antibody X-expressing cell line generated in Example 1 was subjected to fed-batch culture in a 1 L jar. For Jar #1, the cell line used was X #1, and the basal medium/feed medium used was G13 (custom medium manufactured by JX Energy)/F13 (custom medium manufactured by JX Energy). For Jar #2, the cell line used was X #1, and the basal medium/feed medium used was DA1 (custom medium manufactured by Life Technologies Corporation)/DAFM3 (custom medium manufactured by Life Technologies Corporation). For Jar #3, the cell line used was X #2, and the basal medium/feed medium used was G13/F13.

Figure 1B:
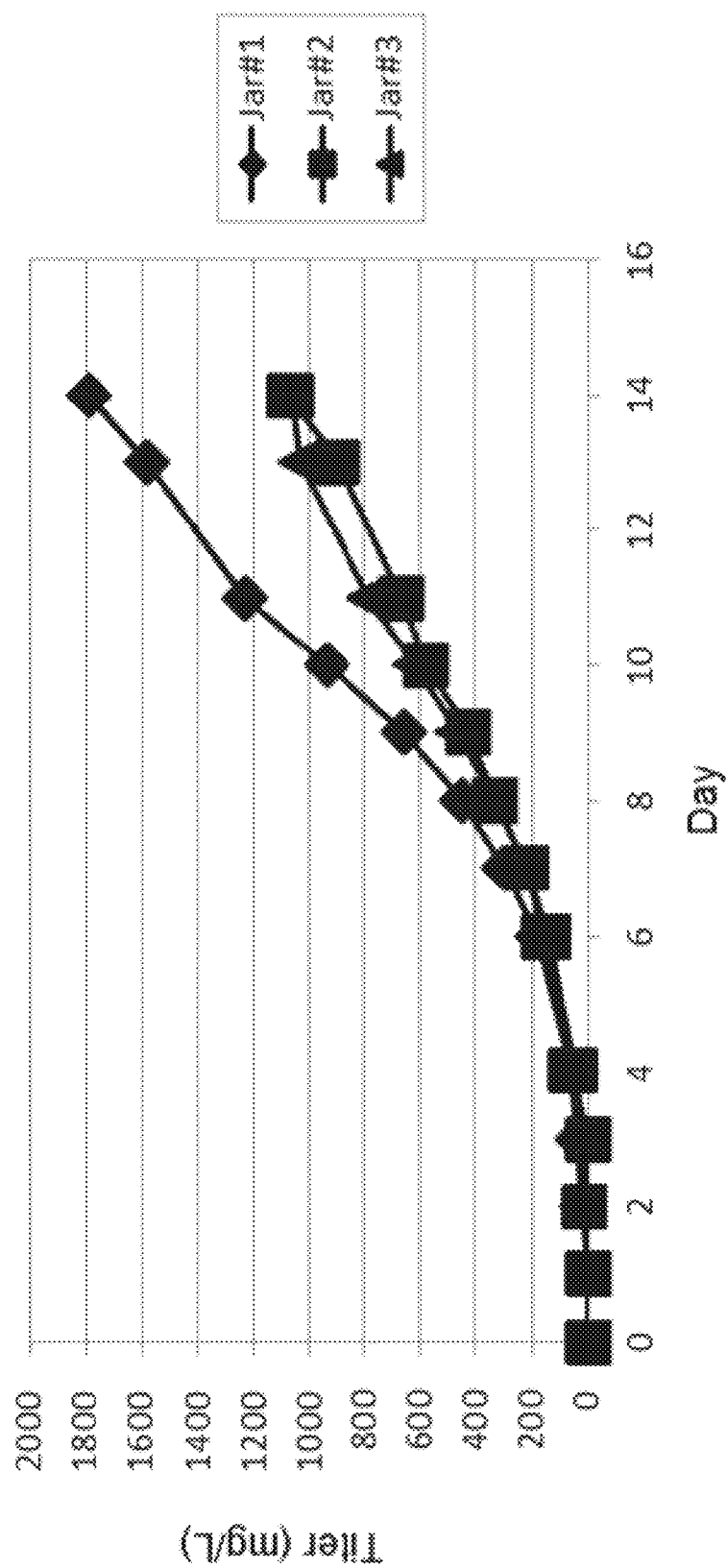
FIG. 1B Results of fed-batch culture of humanized antibody X-expressing cell lines X #1 and X #2 using a 1 L jar are shown.

The change in the number of viable cells and the change in the amount of the antibody produced are shown in FIGS. 1A and 1B, respectively. The amount of antibody produced was compared between the cell lines and was found to be higher in X #1 than in X #2. The amount of antibody produced was compared between the basal media/feed media and was found to be higher in G13/F13 than in DA1/DAFM3.

2-2) Transcriptome Analysis of Humanized Antibody X-Expressing Cell Lines X #1 and X #2

Total RNA was extracted using RNAiso Plus (Takara Bio Inc.) from the cells on days 4, 7, 9, 11, and 14 of the fed-batch culture carried out in (2-1). Subsequently, a sequencing library was prepared using TruSeq RNA Sample Prep Kit v2 (illumina). Specifically, polyA+ RNA was isolated from the total RNA and fragmented. Double-stranded cDNA was synthesized with the obtained RNA fragments as templates. The synthesized double-stranded cDNA was blunt-ended at both ends and phosphorylated, followed by 3'-dA overhang reaction. An indexed adaptor was linked thereto. The adaptor-linked double-stranded cDNA was used as a template in PCR amplification. Then, the obtained PCR products were purified by the magnetic bead method using AMPure XP (Beckman Coulter) to prepare a sequencing library. Then, a cluster serving as a sequencing template was formed using the sequencing library and applied to a HiSeq 2000 system (illumina) where high-speed sequencing analysis was conducted to obtain sequencing data.

2-3) Data Analysis of Transcriptome Analysis Results

Read sequences obtained by the sequencing analysis were mapped onto reference sequences using Bowtie (version. 1.0.0) described in Non Patent Literature 10. The reference sequences were prepared by adding spliced sequences extracted on the basis of Chinese hamster gene information registered in NCBI to Chinese hamster chromosomal sequences registered in NCBI. The expression levels of the read sequences (RPKM: reads per kilobase of exon [intron/intergenic] model per million mapped reads) and novel gene expression regions were studied using ERANGE 3.2 described in Non Patent Literature 11.

Figure 2A:
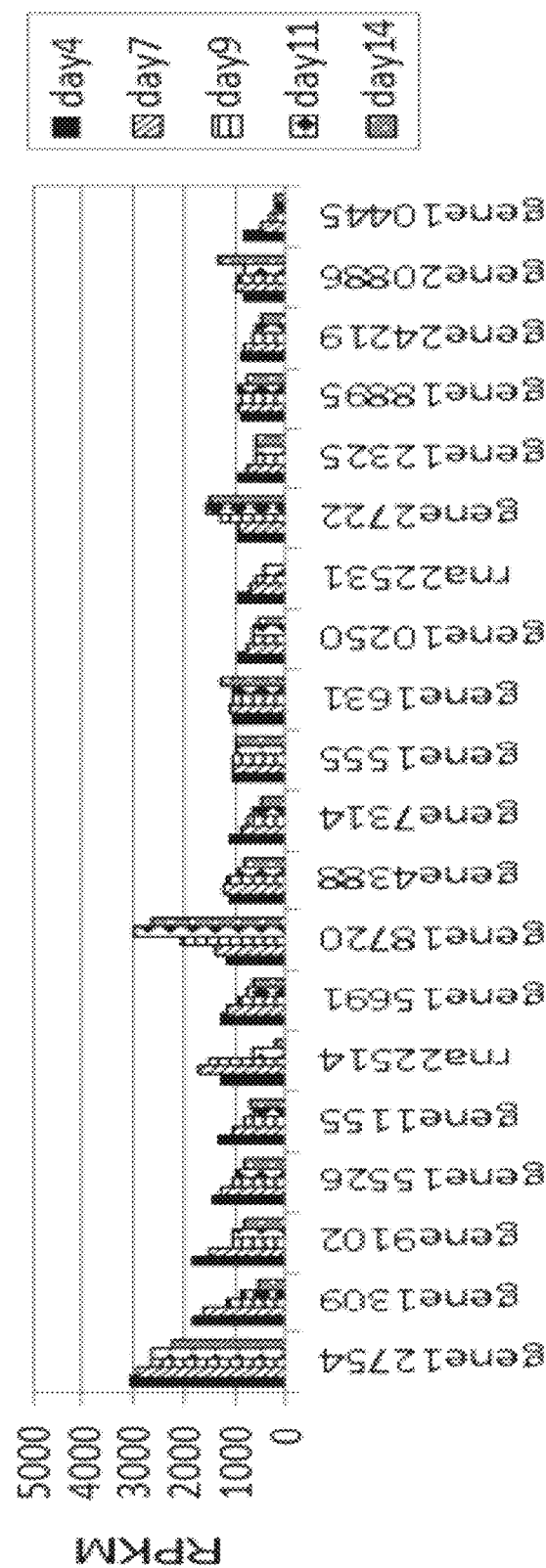
FIG. 2A The expression level of each gene on each day of sampling in fed-batch culture is shown.
Figure 2B:
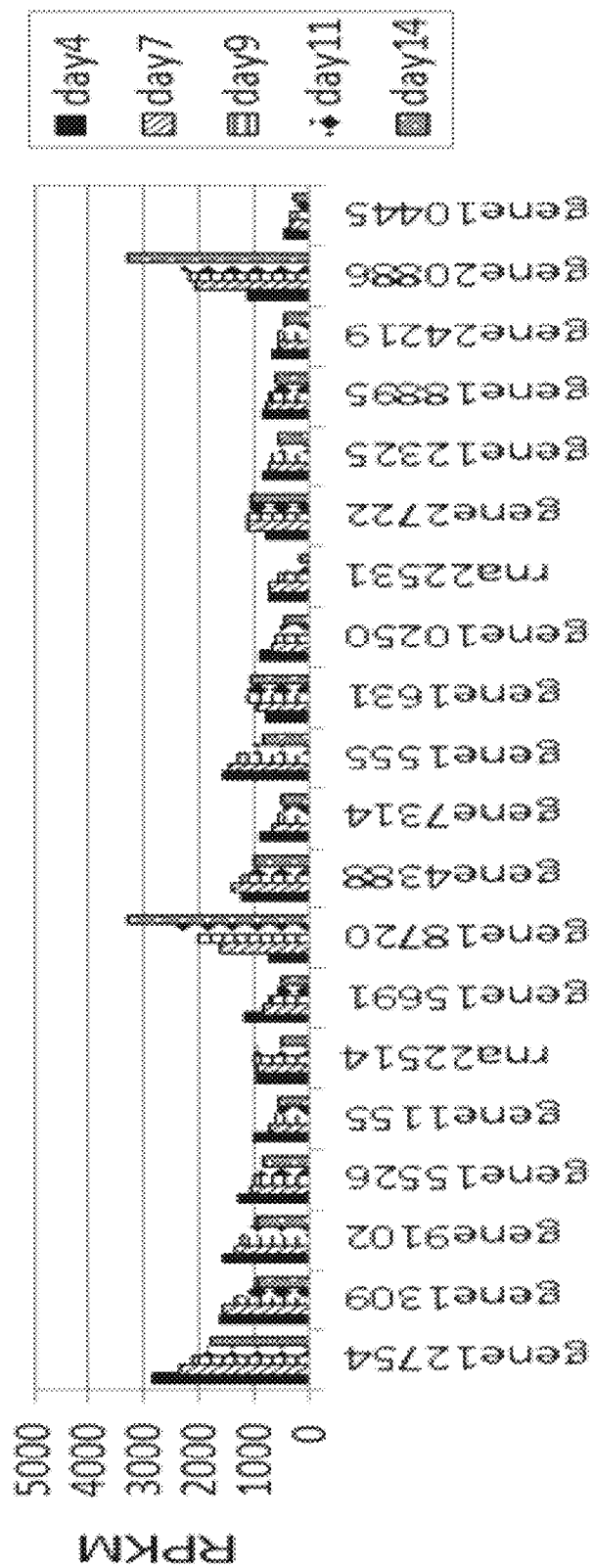
FIG. 2B The expression level of each gene on each day of sampling in fed-batch culture is shown.
Figure 2C:
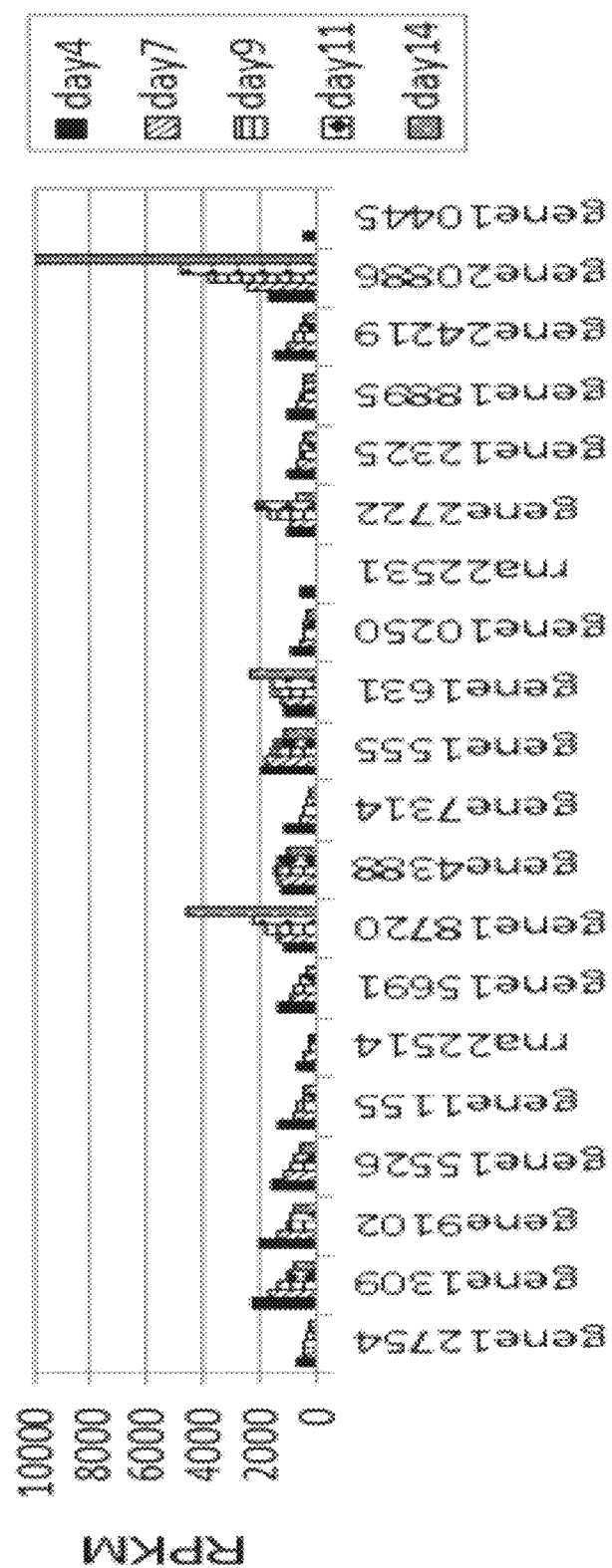
FIG. 2C The expression level of each gene on each day of sampling in fed-batch culture is shown.

The top 20 genes having the highest expression level in the cells on day 4 of Jar #1 are shown in Table 1. The expression levels of the above-mentioned 20 genes on each day of sampling of Jar #1, Jar #2, and Jar #3 are shown in FIGS. 2A, 2B, and 2C, respectively. The Hspa5 (heat shock protein 5) gene exhibited a higher level of expression at the late stage of culture under all the conditions of Jar #1, Jar #2, and Jar #3, and the Fth1 (ferritin heavy chain 1) gene exhibited a higher level of expression at the late stage of culture under the conditions of Jar #2 and Jar #3. The expression level of the Hspa5 gene rose at the late stage of culture irrespective of cell line and medium conditions, suggesting that its promoter activity was increased at the late stage of culture.

TABLE 1

| RPKM/Jar#1, day4 | gene id | gene name | GenBank Accession No. |
|---|---|---|---|
| 1 | gene12754 | Rps14 (ribosomal protein S14) | NM_001244519.1 |
| 2 | gene1309 | Gapdh (glyceraldehyde-3-phosphate dehydrogenase) | NM_001244854.1 |
| 3 | gene9102 | Eef1a1 (eukaryotic translation elongation factor 1 alpha 1) | NM_001244402.1 |
| 4 | gene15526 | Rps11 (40S ribosomal protein S11-like) | XM_003508652.1 |
| 5 | gene1155 | Rplp0 (60S acidic ribosomal protein P0-like) | XM_003495916.1/ XM_003495915.1 |
| 6 | rna22514 | tRNA-Leu | |
| 7 | gene15691 | Rps4 (ribosomal protein S4) | NM_001246673.1 |
| 8 | gene18720 | Hspa5 (heat shock protein 5) | NM_001246739.1 |
| 9 | gene4388 | PKM (pyruvate kinase isozymes M1/M2-like) | XM_003498918.1/ XM_003498920.1/ XM_003498919.1 |
| 10 | gene7314 | Rps2 (ribosomal protein S2) | NM_001244043.1 |
| 11 | gene1555 | Actb (actin, beta) | NM_001244575.1 |
| 12 | gene1631 | Chub2 (polyubiquitin) | NM_001244378.1 |
| 13 | gene10250 | Rps3 (40S ribosomal protein S3a-like) | XM_003504173.1 |
| 14 | rna22531 | tRNA-Glu | |
| 15 | gene2722 | Prdx1 (peroxiredoxin 1) | NM_001246765.1 |
| 16 | gene12325 | Rpsa (ribosomal protein SA) | NM_001244033.1 |
| 17 | gene18895 | Rps25 (40S ribosomal protein S25-like) | XM_003511566.1 |
| 18 | gene24219 | Rpl8 (60S ribosomal protein L8-like) | XM_003515662.1 |
| 19 | gene20886 | Fth1 (ferritin heavy chain 1) | XM_003513182.1 |
| 20 | gene10445 | Hspd1 (heat shock protein 1) | XM_003504341.1 |

(Example 3) Cloning of Promoter Region of Highly Expressed Gene

The promoter region of each gene was cloned for the 18 genes among the top 20 genes having the highest expression level found in Example 2 except for tRNA.

3-1) Cloning of Hspa5 Promoter Region

The Hspa5 promoter region used was a sequence from a nucleotide approximately 3.0 kbp upstream of the start codon of Hspa5 to the nucleotide immediately upstream of the nucleotide sequence corresponding to the start codon with reference to the sequence of mRNA registered under NM_001246739.1 and the scaffold sequence of the Chinese hamster genome registered under NW_003615108.1 in GenBank.

The Hspa5 promoter region was amplified by PCR with the genomic DNA of CHO cells as a template using the primer set given below and KOD FX Neo (Toyobo), and the PCR product was purified using QIAquick PCR Purification kit (Qiagen). The purified DNA fragment was digested with KpnI-HindIII and then inserted into the KpnI-HindIII site of pGL4.10[luc2] (Promega) to construct pGL4.10-Hspa5. The nucleotide sequence of the cloned Hspa5 promoter region is shown in SEQ ID NO: 1 in the sequence listing.

```
Primer set for Hspa5 promoter
Hspa5-KpnI-F:
                                  (SEQ ID NO: 10)
GGGGGGGTACCTATAGCCCAGGCACACATGAACTTG Hspa5-HindIII-R:
                                  (SEQ ID NO: 11)
GGGGGAAGCTTCTTGCCGGCGCTGTGGGCCAGTGCT
```

3-2) Cloning of Promoter Regions of Other Highly Expressed Genes

In accordance with the method described in the preceding section 3-1), Rps14 (ribosomal protein S14), Gapdh (glyceraldehyde-3-phosphate dehydrogenase), Eef1a1 (eukaryotic translation elongation factor 1 alpha 1), Rps11 (40S ribosomal protein S11-like), Rplp0 (60S acidic ribosomal protein PO-like), Rps4 (ribosomal protein S4), PKM (pyruvate kinase isozymes M1/M2-like), Rps2 (ribosomal protein S2), Actb (actin, beta), Chub2 (polyubiquitin), Rps3 (40S ribosomal protein S3a-like), Prdx1 (peroxiredoxin 1), Rpsa (ribosomal protein SA), Rps25 (40S ribosomal protein S25-like), Rpl8 (60S ribosomal protein L8-like), Fth1 (ferritin heavy chain 1), and Hspd1 (heat shock protein 1) promoter regions were each cloned and inserted into the multicloning site of pGL4.10[luc2].

3-3) Construction of pGL4.10-hEF1α

Next, a human EF1-α promoter was amplified by PCR with pEF1/V5-His A (Invitrogen) as a template using the primer set given below and KOD-Plus-Ver. 2 (Toyobo), and the PCR product was purified using a QIAquick PCR Purification kit. The purified DNA fragment was digested with NheI-HindIII and then inserted into the NheI-HindIII site of pGL4.10[luc2] to construct pGL4.10-hEF1α.

```
Primer set for hEF1α promoter
hEF1α-NheI-F:
                                  (SEQ ID NO: 12)
GAGTGGGCTAGCGAATTGGCTCCGGTGCCCGTCAGTG hEF1α-HindIII-R:
                                  (SEQ ID NO: 13)
GAGTGGAAGCTTCCTCACGACACCTGAAATGGAAG
```

(Example 4) Activity Evaluation of Each Promoter with Transient Expression Level of Firefly Luciferase as Indicator 4-1) Transfection The CHO-O1 cells described in (1-2) were suspended at $2.5 \times 10^5$ cells/mL in Opti-MEM I Reduced Serum Medium (Life Technologies Corporation) and seeded at 1 mL/well onto a 24-well plate. 3.2 μg of pGL4.10[luc2] having an insert of each promoter constructed in Example 3, and 0.4 μg of control vector pGL4.74[hRluc/TK] for transfection efficiency correction (Promega) were diluted with 68 μL of OptiPro SFM (Life Technologies Corporation). Meanwhile, 8 μL of Lipofectamine 2000 CD (Life Technologies Corporation) was diluted with 68 μL of OptiPro SFM, mixed with the plasmid solution, and left at room temperature for 20 minutes. Then, half the amount was added to each of 2 wells and cultured in 5% $CO_2$ at 37° C.

4-2) Luciferase Assay

On the day following transfection, the transient expression level of luciferase was measured using a Dual-Luciferase Reporter Assay System (Promega). Specifically, the culture solution was centrifuged at 9000 G for 1 minute, and the supernatant was removed. The cell pellets were washed once with PBS. Then, a cell lysate was prepared using the Passive Lysis Buffer attached to the kit. Then, the amounts of luminescence of firefly luciferase and *Renilla* luciferase were measured using the kit and a luminometer.

Figure 3:
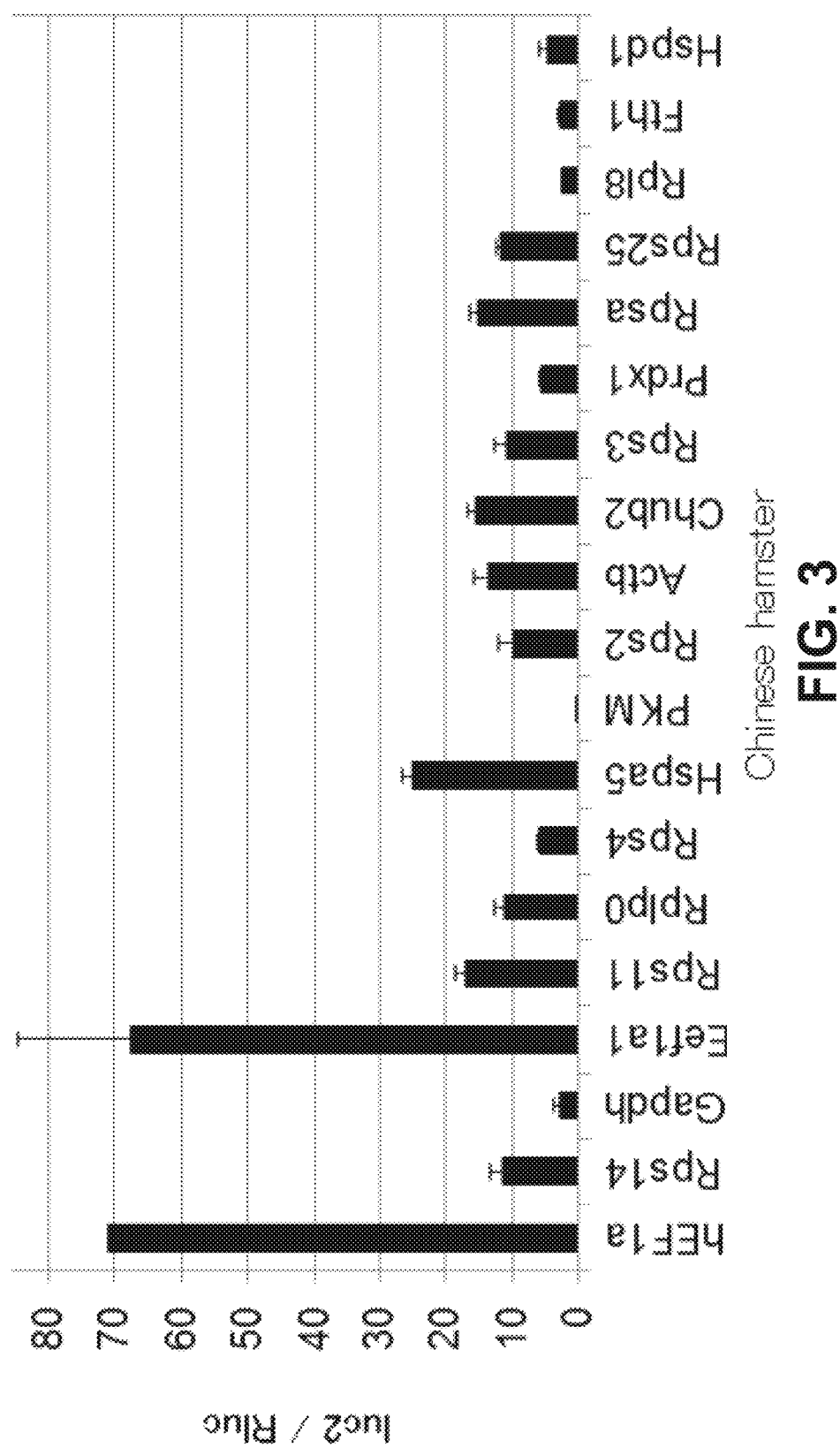
FIG. 3 shows a value obtained by transfecting cells with a firefly luciferase expression vector having an insert of each promoter, and normalizing the firefly luciferase value (luc2) by the *Renilla* luciferase value (Rluc).

FIG. 3 shows a value obtained by transfecting the cells with the luciferase expression vector having an insert of each promoter, and normalizing the amount of luminescence of firefly luciferase (luc2) with the amount of luminescence of *Renilla* luciferase (Rluc) measured on the next day. Eef1a1 exhibited strong promoter activity, which was comparable to that of human EF1-α used as a control. Hspa5 exhibited the second strongest promoter activity after Eef1a1 among the studied promoters.

(Example 5) Evaluation of Hspa5 Promoter by Fed-Batch Culture with Antibody Expression Level as Indicator In the transcriptome analysis, the expression level of the Hspa5 gene was increased at the late stage of culture, suggesting enhanced promoter activity at the late stage of culture. Also, the Hspa5 gene promoter exhibited strong promoter activity in the evaluation of transient expression using the luciferase assay. Accordingly, this promoter was evaluated by the fed-batch culture of an antibody expressing stable pool.

5-1) Construction of Antibody Expression Vector

Figure 4:
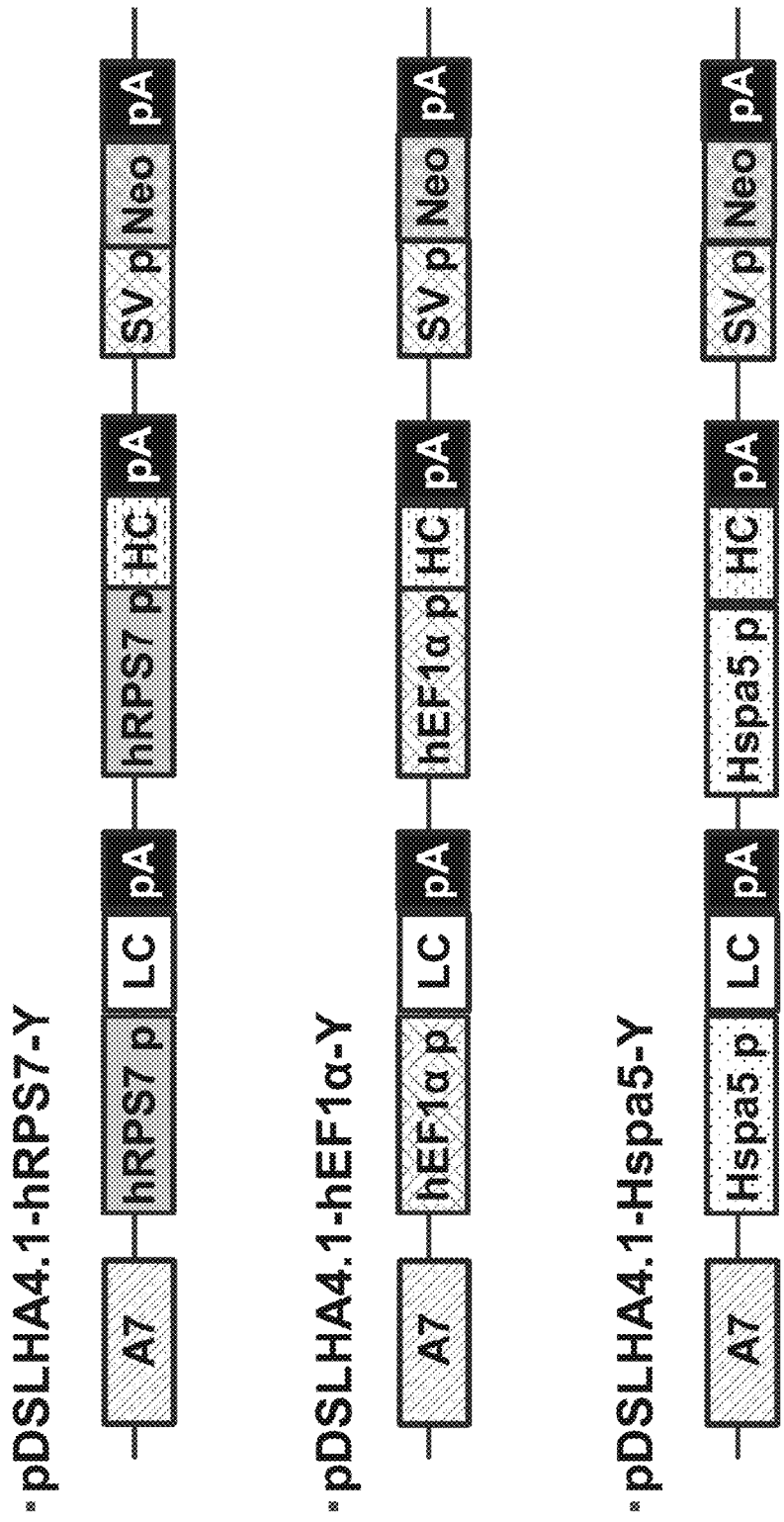
FIG. 4 schematically shows humanized antibody gene Y expression vectors pDSLHA4.1-Hspa5-Y, pDSLHA4.1-hRPS7-Y, and pDSLHA4.1-hEF1α-Y containing a Hspa5 gene, human RPS7 gene or human EF1-α gene-derived promoter as a promoter for antibody H chain and L chain gene expression.

Humanized antibody gene Y expression vector pDSLHA4.1-hRPS7-Y having pDSLH4.1 described in Non Patent Literature 9 as a vector backbone was constructed. This vector contained the human RPS7 promoter described in Patent Literature 2 for the expression of antibody H chain and L chain genes and DNA element A7 described in Patent Literature 2 as a DNA element. Subsequently, pDSLHA4.1-Hspa5-Y and pDSLHA4.1-hEF1α-Y were constructed by substituting the promoter for the antibody H chain and L chain genes in the humanized antibody gene Y expression vector pDSLHA4.1-hRPS7-Y with a Hspa5 or human EF1-α promoter. The vectors are schematically shown in FIG. 4.

pDSLHA4.1-Hspa5-Y was constructed by the following method: first, a Chinese hamster Hspa5 promoter was amplified by PCR with pGL4.10-Hspa5 as a template using the primer set given below and PrimeSTAR Max DNA Polymerase (Takara Bio Inc.), and the PCR product was purified using a QIAquick PCR Purification kit. The purified DNA fragment was digested with NotI-XbaI and then inserted into the NotI-NheI sites of H chain gene expression vector pDSH1.1-hRPS7-Y and L chain gene expression vector pDSL2.1-hRPS7-Y to construct pDSH1.1-Hspa5-Y and pDSL2.1-Hspa5-Y, respectively. Next, a DNA fragment obtained by the digestion of pDSL2.1-Hspa5-Y with AatII-HindIII was inserted into the AatII-HindIII site of pDSH1.1-Hspa5-Y to construct pDSLH3.1-Hspa5-Y. DNA element A7 described in Patent Literature 2 was inserted upstream of the expression cassette of pDSLH3.1-Hspa5-Y to construct pDSLHA4.1-Hspa5-Y.

```
Primer set for Hspa5 promoter
Hspa5-NotI-F:
                                  (SEQ ID NO: 14)
GGGGGGCGGCCGCTATAGCCCAGGCACACATGAACTTG Hspa5-XbaI-R:
                                  (SEQ ID NO: 15)
GGGGGTCTAGACTTGCCGGCGCTGTGGGCCAGTGCT
```

On the other hand, pDSLHA4.1-hEF1α-Y was constructed by the following method: first, a human EF1-α promoter was amplified by PCR with pGL4.10-hEF1α as a template using the primer set given below and KOD-Plus-Ver. 2, and the PCR product was purified using a QIAquick PCR Purification kit. The purified DNA fragment was digested with NotI-NheI and then inserted to the NotI-NheI sites of H chain gene expression vector pDSH1.1-hRPS7-Y and L chain gene expression vector pDSL2.1-hRPS7-Y to construct pDSH1.1-hEF1α-Y and pDSL2.1-hEF1α-Y, respectively. Next, a DNA fragment obtained by the digestion of pDSL2.1-hEF1α-Y with AatII-HindIII was inserted into the AatII-HindIII site of pDSH1.1-hEF1α-Y to construct pDSLH3.1-hEF1α-Y. DNA element A7 described in Patent Literature 2 was inserted upstream of the expression cassette of pDSLH3.1-hEF1α-Y to construct pDSLHA4.1-hEF1α-Y.

```
Primer set for hEF1α promoter
hEF1α-NotI-F:
                              (SEQ ID NO: 16)
GAGTGGGCGGCCGCGAATTGGCTCCGGTGCCCGTCAGTG hEF1α-NheI-R:
                              (SEQ ID NO: 17)
GAGTGGGCTAGCCCTCACGACACCTGAAATGGAAG
```

5-2) Generation of Humanized Antibody Y-Expressing Stable Pool

The CHO-O1 cells described in (1-2) were transfected with the antibody expression vector pDSLHA4.1-Hspa5-Y, pDSLHA4.1-hRPS7-Y, or pDSLHA4.1-hEF1α-Y constructed in (5-1), according to the method described in (4-1). One day after the transfection, the culture solution was centrifuged, and the supernatant was removed. The cell pellets were suspended in a medium containing 800 μg/mL Geneticin, followed by drug selection culture for 1 week on a 6-well plate. Then, the transfectants were cultured in 5% $CO_2$ at 37° C. in a T25 flask and subsequently in a 125 mL Erlenmeyer flask to generate a humanized antibody Y-expressing stable pool. The stable pool was generated at N=2 with each antibody expression vector.

5-3) Evaluation of Amount of Antibody Produced by Fed-Batch Culture of Humanized Antibody Y-Expressing Stable Pool Fed-batch culture was performed in a 125 mL Erlenmeyer flask using each humanized antibody Y-expressing stable pool generated in (5-2). The basal medium used was G13, and the feed medium used was F13.

Figure 5A:
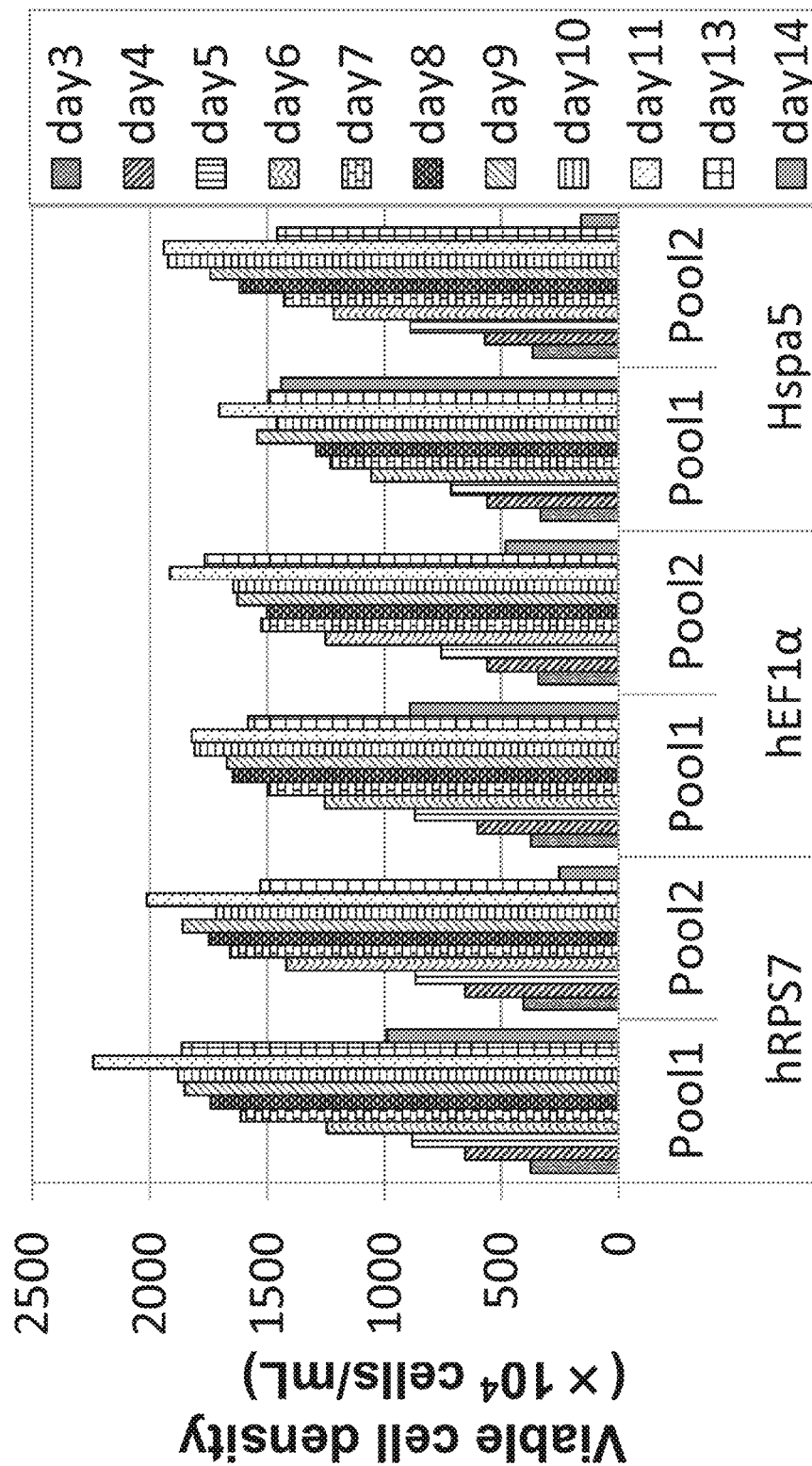
FIG. 5A The amount of antibody produced in fed-batch culture using a humanized antibody Y-expressing stable pool was compared between expression under a Hspa5 gene promoter and expression under a human RPS7 gene promoter or a human EF1-α gene promoter.
Figure 5B:
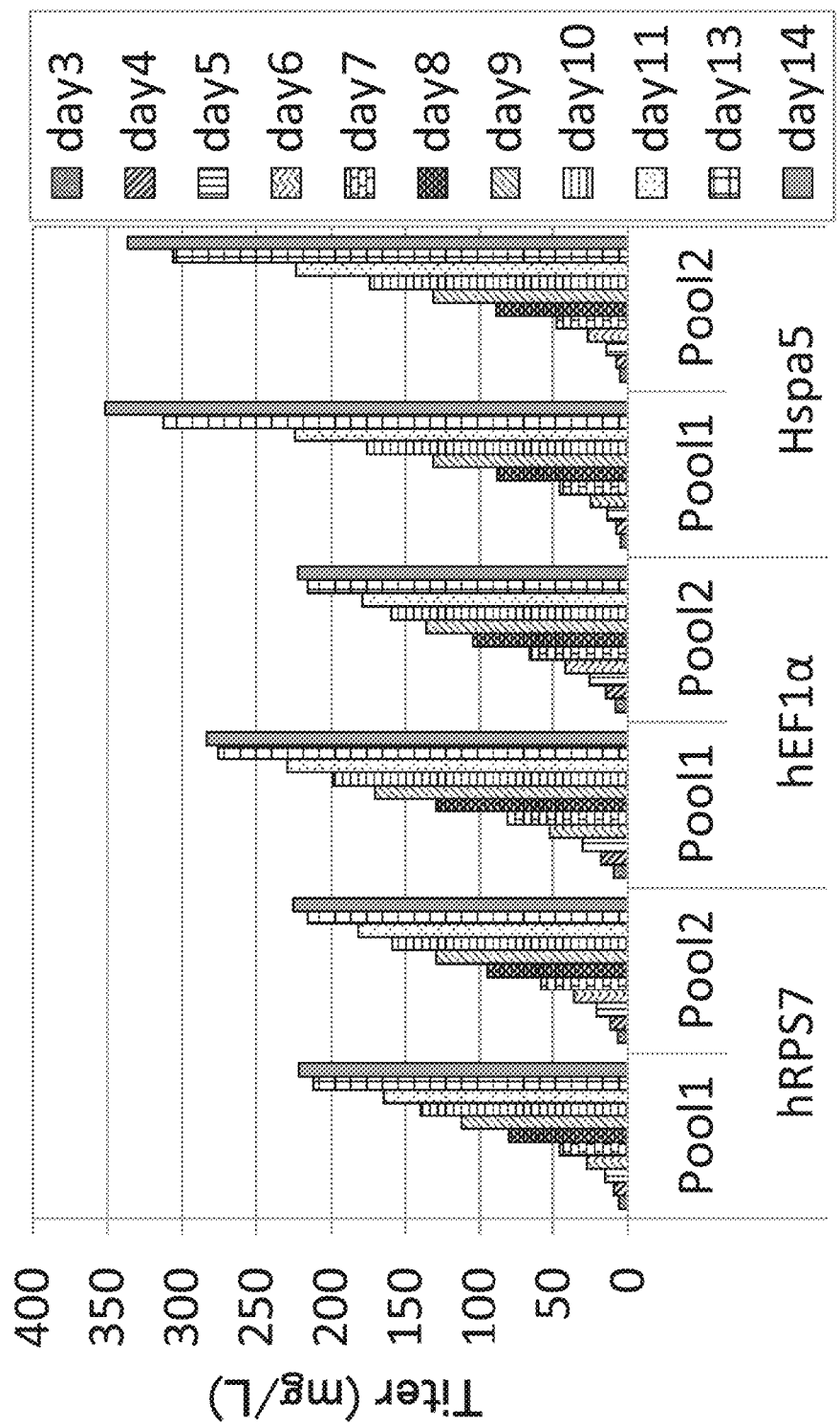
FIG. 5B The amount of antibody produced in fed-batch culture using a humanized antibody Y-expressing stable pool was compared between expression under a Hspa5 gene promoter and expression under a human RPS7 gene promoter or a human EF1-α gene promoter.
Figure 5C:
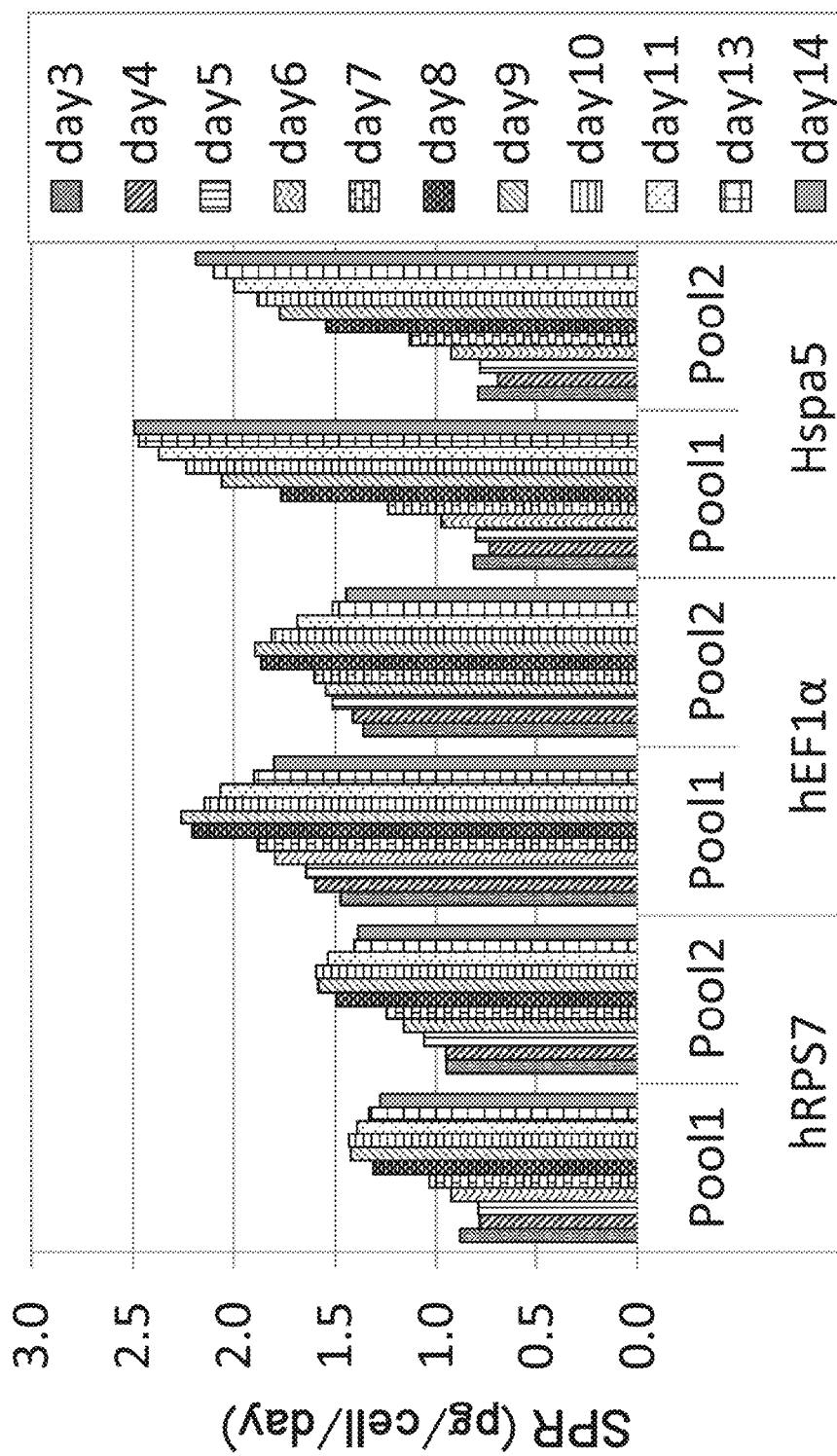
FIG. 5C The amount of antibody produced in fed-batch culture using a humanized antibody Y-expressing stable pool was compared between expression under a Hspa5 gene promoter and expression under a human RPS7 gene promoter or a human EF1-α gene promoter.

Change in the number of viable cells, change in the amount of the antibody produced, and change in the amount of the antibody produced per cell and per day (SPR: specific production rate) are shown in FIGS. 5A, 5B, and 5C, respectively. The amount of the antibody produced per cell and per day was calculated by dividing the amount of the antibody produced at the time of sampling by the integrated number of viable cells up to the time of sampling. At the initial stage of culture, both the amount of the antibody produced and the amount of the antibody produced per cell and per day for the Hspa5 promoter were comparable to those for the human RPS7 promoter used as a control and lower than those for the human EF1-α promoter. However, the amount of the antibody produced per cell and per day for the Hspa5 promoter increased drastically at the intermediate stage or later of culture and was 1.3 and 0.9 times the values for the human RPS7 promoter and the human EF1-α promoter, respectively, on day 10 of culture and 1.8 and 1.4 times the values for the human RPS7 promoter and the human EF1-α promoter, respectively, on day 14 of culture. As a result, the amount of the antibody produced for the Hspa5 promoter on day 14 of culture reached 1.5 and 1.4 times the values for the human RPS7 promoter and the human EF1-α promoter, respectively, and thus greatly exceeded the amount of the antibody produced for the promoters currently frequently used.

Figure 6:
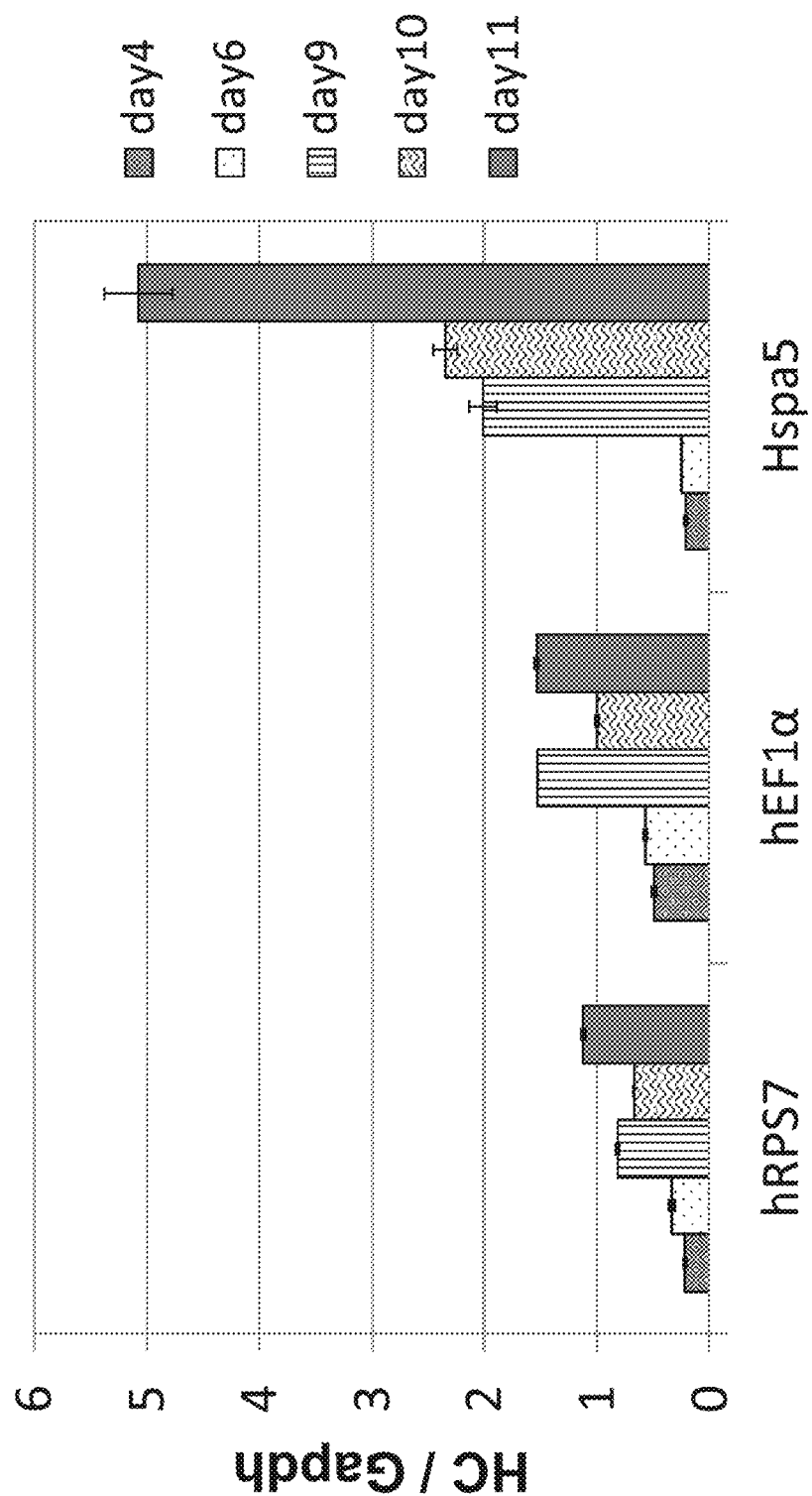
FIG. 6 shows results of comparing the time-dependent relative expression level of a H chain gene in fed-batch culture using a humanized antibody Y-expressing stable pool between a Hspa5 gene promoter, a human RPS7 gene promoter and a human EF1-α gene promoter.

5-4) mRNA Expression Level Evaluation by Fed-Batch Culture of Humanized Antibody Y-Expressing Stable Pool The mRNA expression level of the antibody Y gene of interest was compared by real-time PCR using the cells obtained over time in the fed-batch culture carried out in (5-3). Total RNA was extracted from the cells on days 4, 6, 9, 10, and 11 of fed-batch culture using a RNeasy Micro Kit (Qiagen), and cDNA was synthesized by a reverse transcription reaction with the total RNA as a template using a PrimeScript High Fidelity RT-PCR Kit (Takara Bio Inc.). Next, real-time PCR was carried out with the reverse transcription reaction solution as a template using the primer set given below and SYBR Premix Ex Taq II (Takara Bio Inc.). Calibration curves were prepared using the humanized antibody Y expression vector used in transfection for the H chain gene, and plasmid DNA obtained by the TOPO cloning of a DNA fragment amplified with the primer set given below for the Gapdh gene to calculate the numbers of copies of the H chain gene and the Gapdh gene in each sample. The expression level of the H chain gene normalized by dividing the number of copies of the H chain gene by the number of copies of the Gapdh gene in each sample is shown in FIG. 6. At the initial stage of culture, the mRNA expression level of the H chain gene under the Hspa5 promoter was comparable to that under the human RPS7 promoter used as a control and lower than that under the human EF1-α promoter. However, the expression level of the H chain gene under the Hspa5 promoter was increased greatly at the intermediate stage or later of culture and largely exceeded the values under the human RPS7 promoter and the human EF1-α promoter. The results showing this time-dependent change in mRNA expression level were similar to the results for the protein expression level shown in FIG. 5C. These results indicated that the increase in protein expression level at the late stage of culture for the Hspa5 promoter was ascribable to an increase in promoter activity of the Hspa5 promoter.

```
Primer set for H chain gene
HC-F:
                              (SEQ ID NO: 18)
TGGCTGAACGGCAAAGAGTA

HC-R:
                              (SEQ ID NO: 19)
TTGGCCTTGGAGATGGTCTT

Primer set for Gapdh gene
Gapdh-F:
                              (SEQ ID NO: 20)
GTATTGGACGCCTGGTTACCAG Gapdh-R:
                              (SEQ ID NO: 21)
AGTCATACTGGAACATGTAGAC
```

(Example 6) Evaluation of Hspa5 Promoter by Fed-Batch Culture with *Renilla* Luciferase Expression Level as Indicator 6-1) Construction of *Renilla* Luciferase Expression Vector A Hspa5 promoter, a human RPS7 promoter, or a human EF1-α promoter was inserted into the multicloning site of *Renilla* luciferase expression vector pGL4.82[hRluc/Puro] (Promega) to construct pGL4.82-Hspa5, pGL4.82-hRPS7, or pGL4.82-hEF1α.

Specifically, the KpnI-HindIII-digested Hspa5 promoter prepared in (3-1) was inserted into the KpnI-HindIII site of pGL4.82[hRluc/Puro] to construct pGL4.82-Hspa5.

Next, a human RPS7 promoter was amplified by PCR with pDSLHA4.1-hRPS7-Y as a template using the primer set given below and PrimeSTAR Max DNA Polymerase (Takara Bio Inc.), and the PCR product was purified using a QIAquick PCR Purification kit. The purified DNA fragment was digested with XhoI-HindIII and then inserted into the XhoI-HindIII site of pGL4.82[hRluc/Puro] to construct pGL4.82-hRPS7.

```
Primer set for hRPS7 promoter
hRPS7-XhoI-F:
                          (SEQ ID NO: 22)
GGGGGCTCGAGTGTATATTAACAGCACATTA hRPS7-HindIII-R:
                          (SEQ ID NO: 23)
GGGGGAAGCTTCGGCTTTCTCCTGGGAGAAC
```

Also, the NheI-HindIII-digested human EF1-α promoter prepared in (3-3) was inserted into the NheI-HindIII site of pGL4.82[hRluc/Puro] to construct pGL4.82-hEF1α.

6-2) Generation of *Renilla* Luciferase-Expressing Stable Pool

The CHO-O1 cells described in (1-2) were transfected with the *Renilla* luciferase expression vector pGL4.82-Hspa5, pGL4.82-hRPS7, or pGL4.82-hEF1α constructed in (6-1), according to the method described in (4-1). One day after the transfection, the culture solution was centrifuged, and the supernatant was removed. The cell pellets were suspended in a medium containing 8 μg/mL puromycin, followed by drug selection culture for 12 days on a 6-well plate. Then, the transfectants were cultured in 5% CO$_2$ at 37° C. in a T25 flask and subsequently in a 125 mL Erlenmeyer flask to generate a *Renilla* luciferase-expressing stable pool. The stable pool was generated at N=3 with each *Renilla* luciferase expression vector.

6-3) Evaluation of Amount of Protein Produced by Fed-Batch Culture of *Renilla* Luciferase Expressing Stable Pool Fed-batch culture was performed in a 125 mL Erlenmeyer flask using each *Renilla* luciferase-expressing stable pool generated in (6-2). The basal medium used was G13, and the feed medium used was F13. The expression level of *Renilla* luciferase was measured with respect to the cells on days 3, 4, 7, 9, and 11 of fed-batch culture using *Renilla* Luciferase Assay System (Promega).

Specifically, the culture solution was centrifuged at 9000 G for 1 minute, and the supernatant was removed. The cell pellets were washed once with PBS. Then, a cell lysate was prepared using *Renilla* Luciferase Assay Lysis Buffer attached to the kit. Then, the amount of luminescence of *Renilla* luciferase was measured using the kit and a luminometer.

Figure 7A:
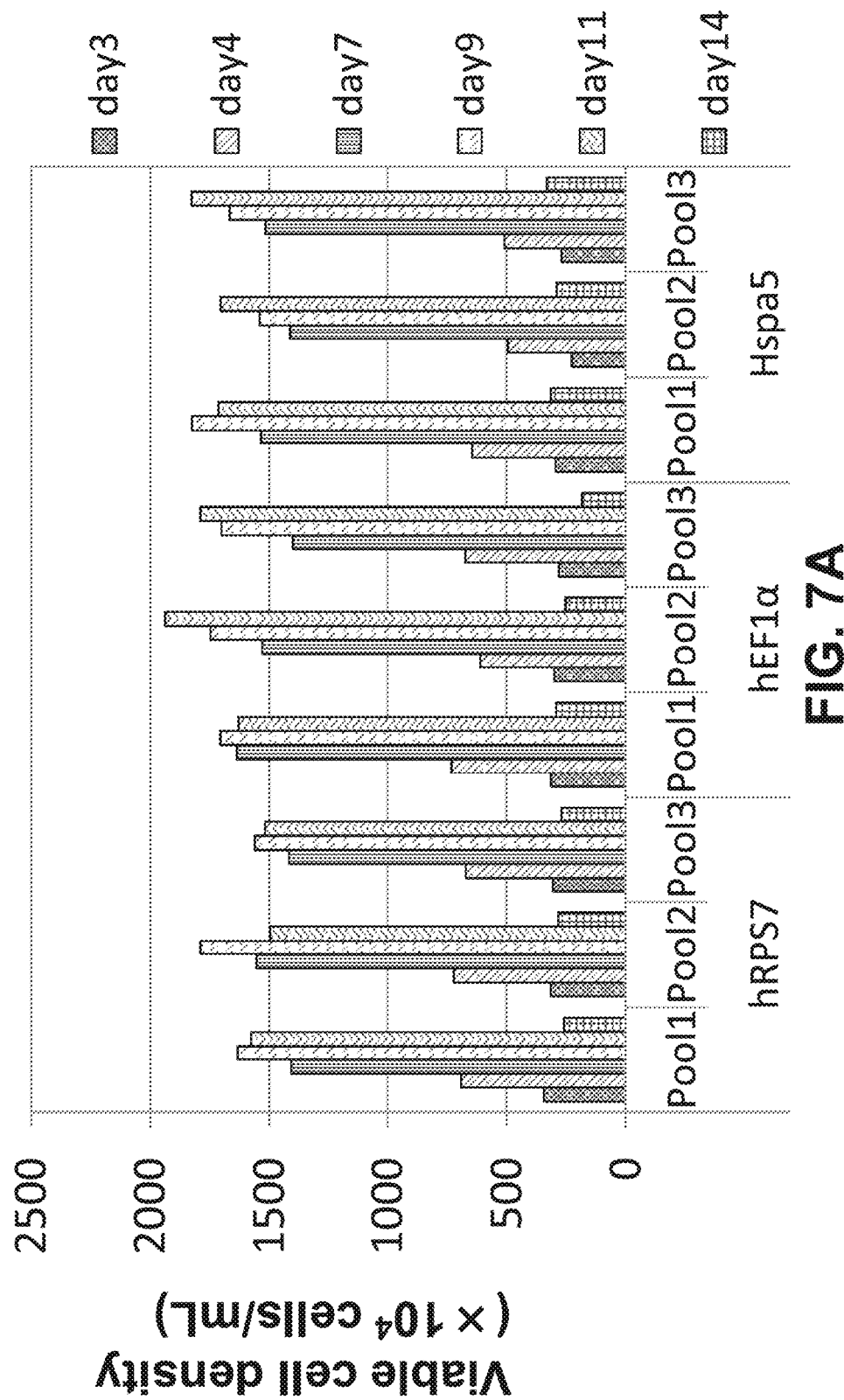
FIG. 7A The amount of *Renilla* luciferase produced in fed-batch culture using a *Renilla* luciferase (Rluc) expressing stable pool was compared between expression under a Hspa5 gene promoter (3 kbp) and expression under a human RPS7 gene promoter and a human EF1-α gene promoter.
Figure 7B:
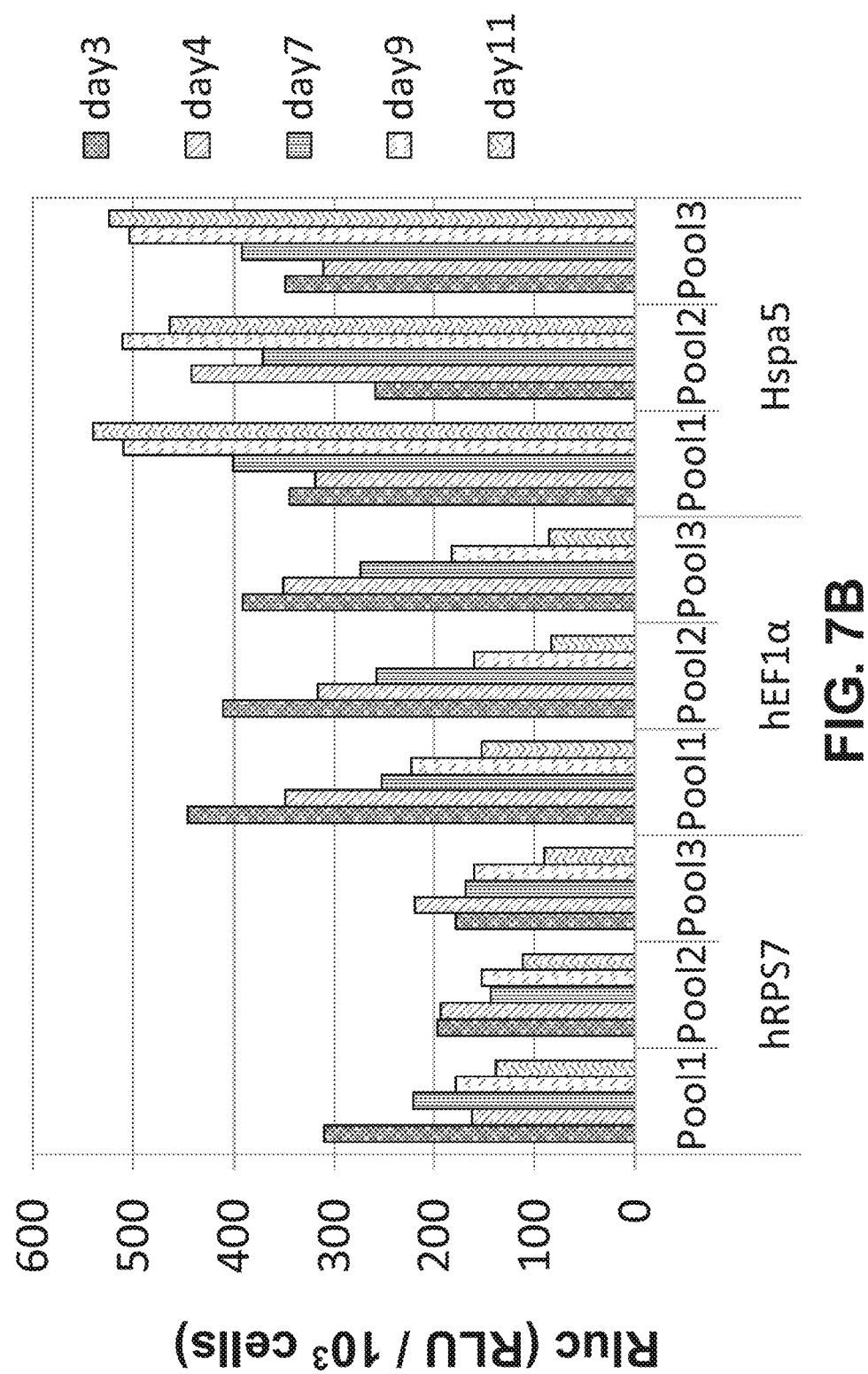
FIG. 7B The amount of *Renilla* luciferase produced in fed-batch culture using a *Renilla* luciferase (Rluc)-expressing stable pool was compared between expression under a Hspa5 gene promoter (3 kbp) and expression under a human RPS7 gene promoter and a human EF1-α gene promoter.

Change in the number of viable cells and change in the amount of luminescence of *Renilla* luciferase per $10^3$ cells are shown in FIGS. 7A and 7B, respectively. In the cells at the initial stage of culture, the amount of luminescence of *Renilla* luciferase for the Hspa5 promoter was higher than that for the human RPS7 promoter used as a control and comparable to that for the human EF1-α promoter. However, the amount of luminescence of *Renilla* luciferase for the Hspa5 promoter was increased over time in the cells at the intermediate stage or later of culture, whereas the amount of luminescence of *Renilla* luciferase decreased drastically for the human RPS7 promoter and the human EF1-α promoter. Hence, in the cells on day 11 of culture, the amount of luminescence of *Renilla* luciferase for the Hspa5 promoter was as large as 4.5 and 4.8 times the values for the human RPS7 promoter and the human EF1-α promoter, respectively. Thus, as a result of attempting the expression of *Renilla* luciferase, it was possible to confirm that the Hspa5 promoter was superior to the existing human RPS7 promoter and human EF1-α promoter in the effect of enhancing the amount of protein produced in a system other than an antibody expression system. These results indicated that the Hspa5 promoter is also useful in the production of proteins other than antibodies.

(Example 7) Study on Hspa5 Promoter Length with Antibody Expression Level as Indicator in Fed-Batch Culture 7-1) Construction of Antibody Expression Vector pDSLHA4.1-Hspa5-2.5-Y, pDSLHA4.1-Hspa5-2.0-Y, pDSLHA4.1-Hspa5-1.5-Y, pDSLHA4.1-Hspa5-1.1-Y, and pDSLHA4.1-Hspa5-0.6-Y were constructed by substituting the promoter for antibody H chain and L chain genes in the humanized antibody gene Y expression vector pDSLHA4.1-hRPS7-Y by a partial sequence of the Hspa5 promoter. In these expression vectors, the partial sequence of the Hspa5 promoter used was a sequence from a nucleotide approximately 2.5, 2.0, 1.5, 1.1, and 0.6 kbp, respectively, upstream of the start codon of Hspa5 to the nucleotide immediately upstream of the nucleotide sequence corresponding to the start codon.

pDSLHA4.1-Hspa5-2.5-Y was constructed by the following method: first, the partial sequence of the Chinese hamster Hspa5 promoter was amplified by PCR with pGL4.10-Hspa5 as a template using the primer set given below and PrimeSTAR Max DNA Polymerase, and the PCR product was purified using a QIAquick PCR Purification kit. The purified DNA fragment was digested with NotI-XbaI and then inserted to the NotI-NheI sites of H chain gene expression vector pDSH1.1-hRPS7-Y and L chain gene expression vector pDSL2.1-hRPS7-Y to construct pDSH1.1-Hspa5-2.5-Y and pDSL2.1-Hspa5-2.5-Y, respectively. Next, a DNA fragment obtained by the digestion of pDSL2.1-Hspa5-2.5-Y with AatII-HindIII was inserted into the AatII-HindIII site of pDSH1.1-Hspa5-2.5-Y to construct pDSLH3.1-Hspa5-2.5-Y. DNA element A7 described in Patent Literature 2 was inserted upstream of the expression cassette of pDSLH3.1-Hspa5-2.5-Y to construct pDSLHA4.1-Hspa5-2.5-Y. pDSLHA4.1-Hspa5-2.0-Y, pDSLHA4.1-Hspa5-1.5-Y, pDSLHA4.1-Hspa5-1.1-Y, and pDSLHA4.1-Hspa5-0.6-Y were constructed in the same way as above.

```
Primer set for Hspa5 promoter 2.5 kbp
Hspa5-NotI-2500F:
                                     (SEQ ID NO: 24)
GGGGGGCGGCCGCTGGTCGGTGGTTAAGAGCAC Hspa5-XbaI-R:
                                     (SEQ ID NO: 15)
GGGGGTCTAGACTTGCCGGCGCTGTGGGCCAGTGCT Primer set for Hspa5 promoter 2.0 kbp
Hspa5-NotI-2000F:
                                     (SEQ ID NO: 25)
GGGGGGCGGCCGCTCCCAACTGGACACAGTAAT Hspa5-XbaI-R:
                                     (SEQ ID NO: 15)
GGGGGTCTAGACTTGCCGGCGCTGTGGGCCAGTGCT Primer set for Hspa5 promoter 1.5 kbp
Hspa5-NotI-1500F:
                                     (SEQ ID NO: 26)
GGGGGGCGGCCGCAATTCTACCTGTACCACTCA Hspa5-XbaI-R:
                                     (SEQ ID NO: 15)
GGGGGTCTAGACTTGCCGGCGCTGTGGGCCAGTGCT Primer set for Hspa5 promoter 1.1 kbp
Hspa5-NotI-1100F:
                                     (SEQ ID NO: 27)
GGGGGGCGGCCGCCGGGAACATTATGGGCGAC Hspa5-XbaI-R:
                                     (SEQ ID NO: 15)
GGGGGTCTAGACTTGCCGGCGCTGTGGGCCAGTGCT Primer set for Hspa5 promoter 0.6 kbp
Hspa5-NotI-600F:
                                     (SEQ ID NO: 28)
GGGGGGCGGCCGCGGAACTGACACGCAGACCCC Hspa5-XbaI-R:
                                     (SEQ ID NO: 15)
GGGGGTCTAGACTTGCCGGCGCTGTGGGCCAGTGCT
```

7-2) Generation of Humanized Antibody Y-Expressing Stable Pool

The CHO-O1 cells described in (1-2) were transfected with the antibody expression vector pDSLHA4.1-hRPS7-Y, pDSLHA4.1-hEF1α-Y, pDSLHA4.1-Hspa5-Y, pDSLHA4.1-Hspa5-2.5-Y, pDSLHA4.1-Hspa5-2.0-Y, pDSLHA4.1-Hspa5-1.5-Y, pDSLHA4.1-Hspa5-1.1-Y, or pDSLHA4.1-Hspa5-0.6-Y constructed in (5-1) or (7-1), according to the method described in (4-1). Then, drug selection culture was performed by the method described in (5-2) to generate a humanized antibody Y-expressing stable pool. The stable pool was generated at N=3 with each antibody expression vector.

7-3) Evaluation of Amount of Antibody Produced by Fed-Batch Culture of Humanized Antibody Y-Expressing Stable Pool Fed-batch culture was performed in a 125 mL Erlenmeyer flask using each humanized antibody Y-expressing stable pool generated in (7-2). The basal medium used was G13, and the feed medium used was F13.

Figure 8A:
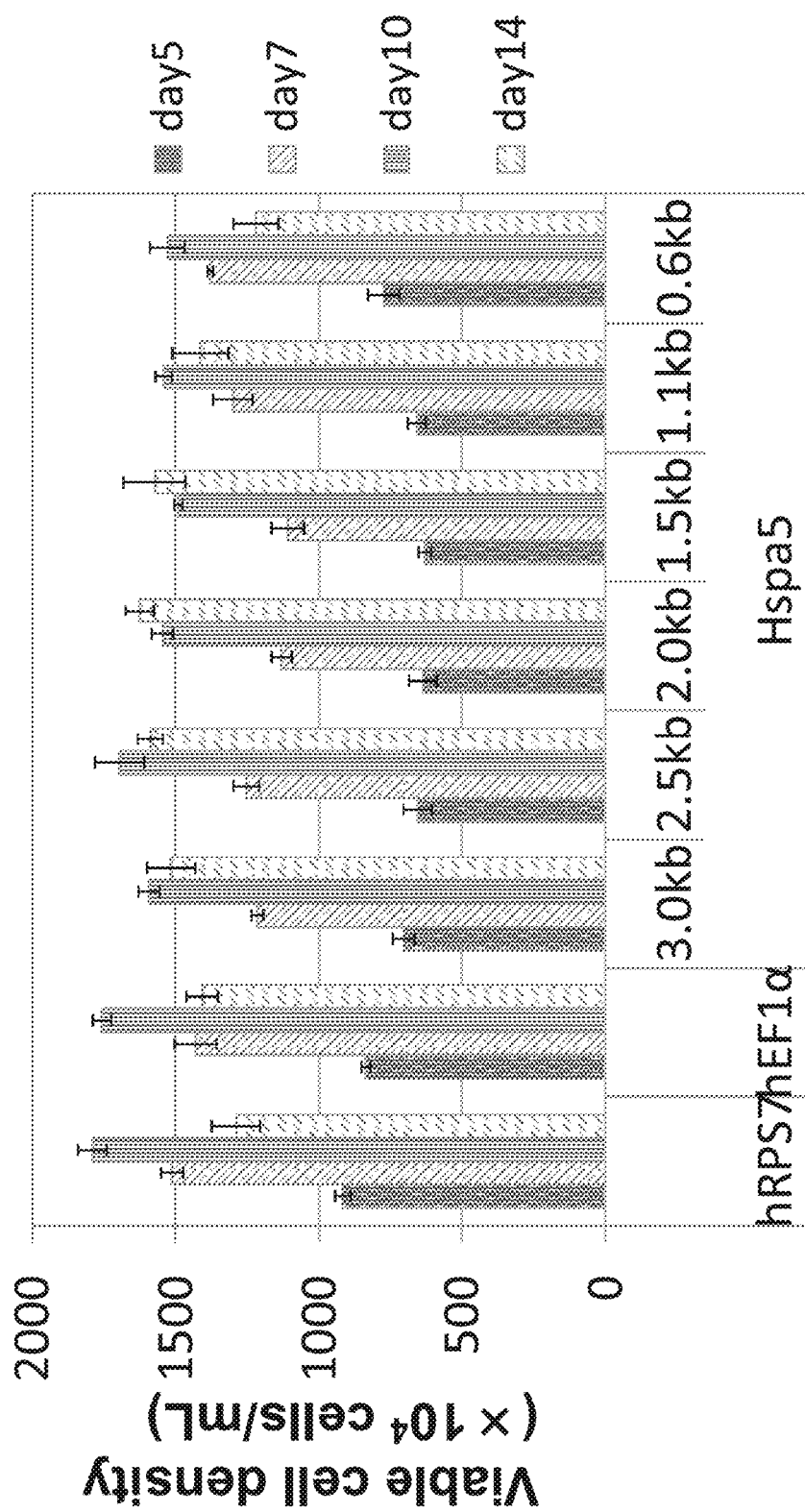
FIG. 8A The amount of antibody produced in the fed-batch culture of a humanized antibody Y-expressing stable pool generated using a Hspa5 gene promoter of each promoter length was compared with that for a human RPS7 gene promoter and a human EF1-α gene promoter.
Figure 8B:
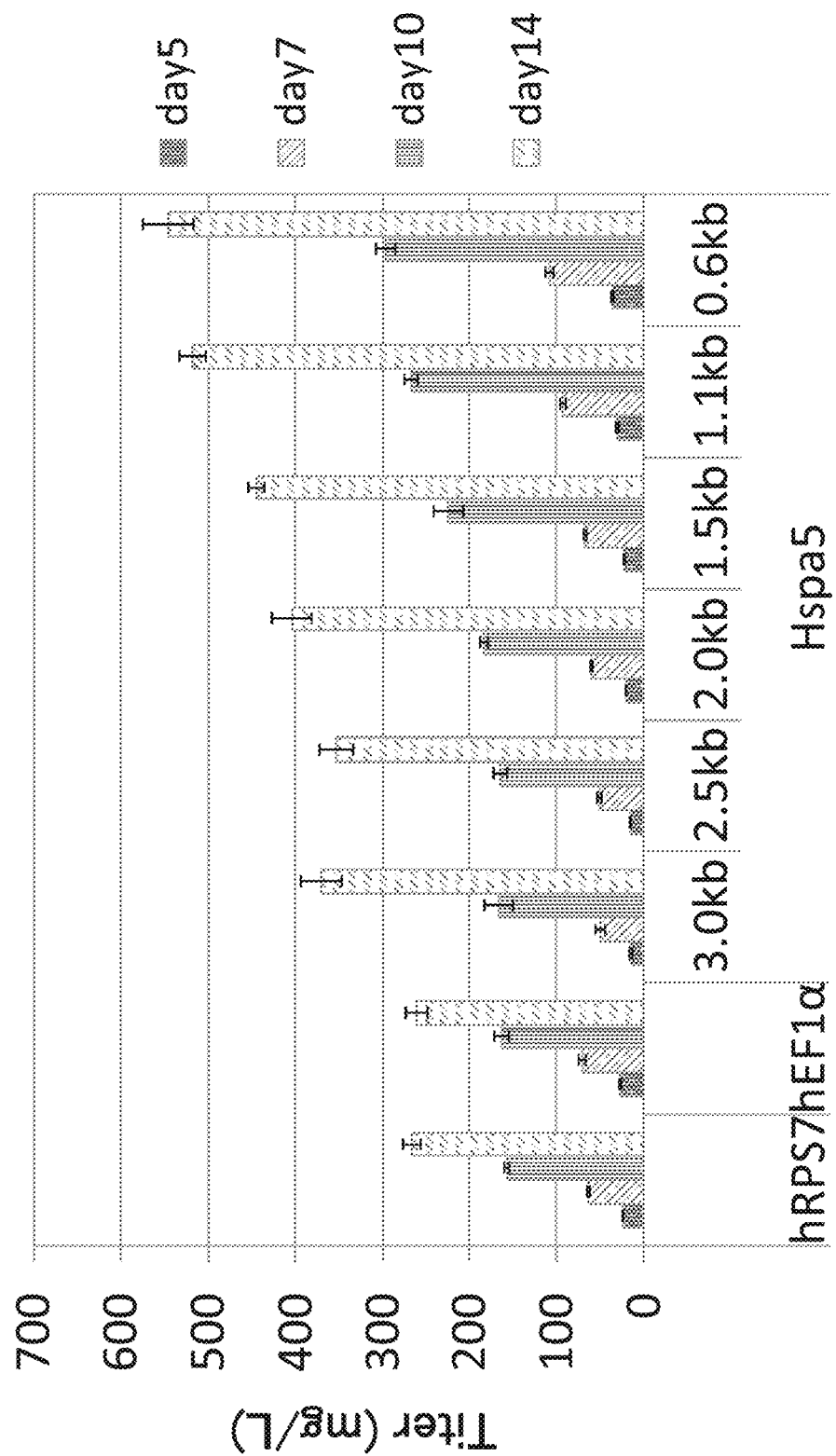
FIG. 8B The amount of antibody produced in the fed-batch culture of a humanized antibody Y-expressing stable pool generated using a Hspa5 gene promoter of each promoter length was compared with that for a human RPS7 gene promoter and a human EF1-α gene promoter.
Figure 8C:
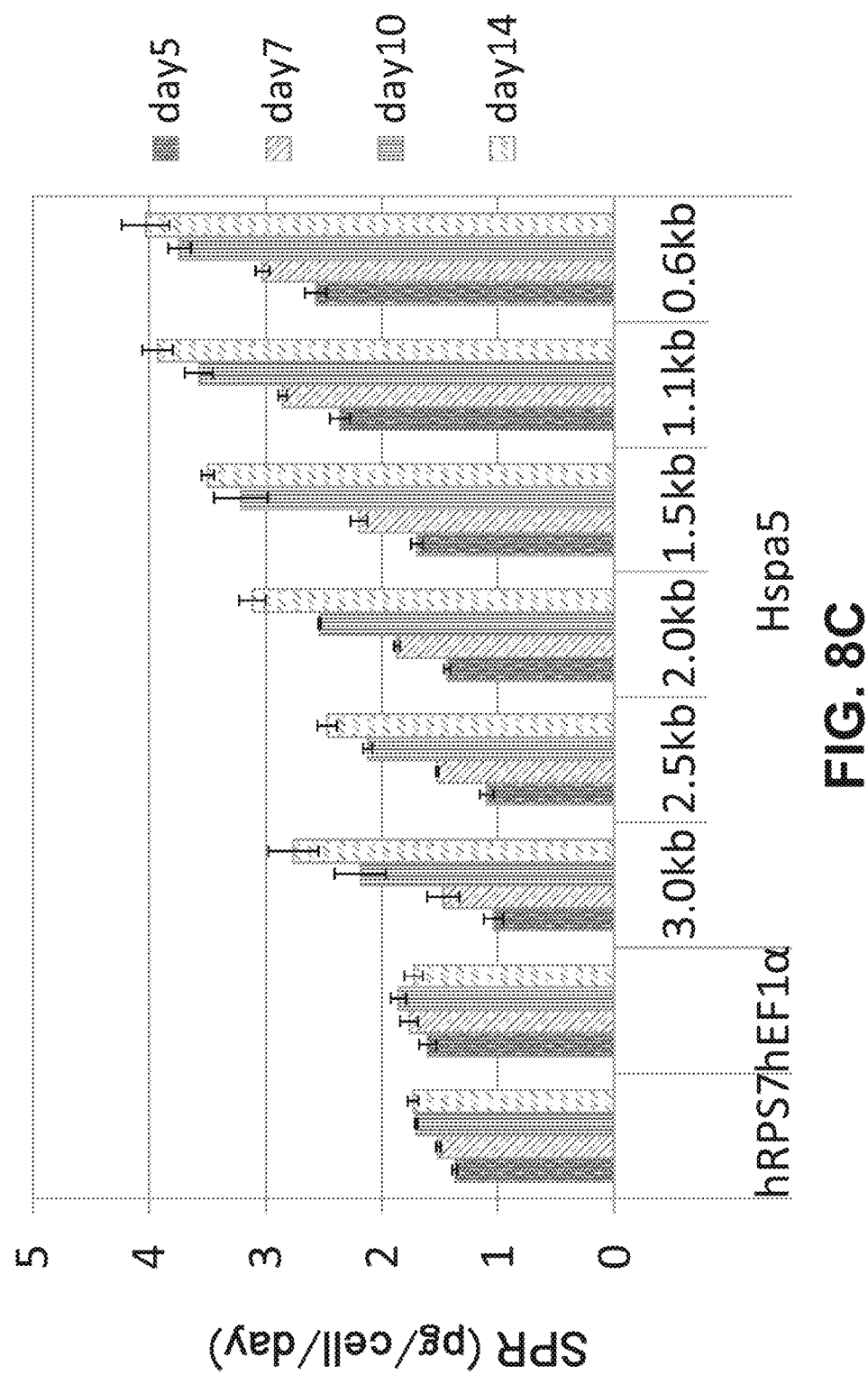
FIG. 8C The amount of antibody produced in the fed-batch culture of a humanized antibody Y-expressing stable pool generated using a Hspa5 gene promoter of each promoter length was compared with that for a human RPS7 gene promoter and a human EF1-α gene promoter.

Change in the number of viable cells, change in the amount of the antibody produced, and change in the amount of the antibody produced per cell and per day (SPR: specific production rate) are shown in FIGS. 8A, 8B, and 8C, respectively. Unexpectedly, the Hspa5 promoters having a length decreased from 3.0 kbp to 0.6 or 1.1 kbp exhibited high productivity from the initial stage of culture. On day 5 of culture, both the amount of the antibody produced and the amount of the antibody produced per cell and per day for the Hspa5 promoters were higher than those for the human RPS7 promoter and the human EF1-α promoter used as controls. Furthermore, the amount of the antibody produced per cell and per day was increased at the intermediate stage or later of culture, irrespective of the length of the Hspa5 promoter, and both the values for the 0.6 and 1.1 kbp Hspa5 promoters were 2.3 times the value for the human EF1-α promoter on day 14 of culture. As a result, the amounts of the antibody produced for the 0.6 and 1.1 kbp Hspa5 promoters on day 14 of culture both exceeded 0.5 g/L and reached 2.1 and 2.0 times, respectively, the value for the human EF1-α promoter. The Hspa5 promoter having the optimized length was able to exert its maximum promoter activity and consequently surpassed the promoters currently in frequent use in terms of the amount of the antibody produced.

7-4) Evaluation of Amount of Antibody Produced by Fed-Batch Culture of Humanized Antibody Y-Expressing Monoclone A monoclone was obtained from the humanized antibody Y-expressing stable pool generated using the 0.6 kbp partial sequence of the Hspa5 promoter in (7-2), and evaluated for the amount of the antibody produced by fed-batch culture.

First, highly expressing cells were enriched using a flow cytometer. Specifically, the culture solution was centrifuged at 200 G for 3 minutes, and the supernatant was removed. The cell pellets were washed twice with 2% BSA-PBS and then resuspended in 2% BSA-PBS. Fluorescein isothiocyanate (FITC)-conjugated Goat F(ab')$_2$ Fragment Anti-Human IgG (H+L) (Beckman Coulter) was added to the obtained cell suspension, which was then stained at 4° C. for 30 minutes. Then, the cell suspension was centrifuged at 200 G for 3 minutes, and the supernatant was removed. The cell pellets were washed twice with 2% BSA-PBS and then resuspended in 2% BSA-PBS. The obtained cell suspension was sorted using a BD FACSAria Fusion sorter (Becton Dickinson). The sorting was carried out under the following conditions: first, in a dot plot with FSC-Area on the abscissa against SSC-Area on the ordinate, two gates were set on the basis of the value of SSC, and four gates were further set on the basis of the value of FSC. Then, the top 5% cell population that exhibited the highest fluorescence intensity was sorted in cell populations in fractions having the smallest value of FSC and a smaller value of SSC.

Next, the sorted cell population was cultured, then suspended in a soft agar medium, seeded onto a 6-well plate, and cultured in 5% CO$_2$ at 37° C. After the culturing, a colony highly expressing humanized antibody Y was picked onto a 96-well plate using ClonePix 2. The colony thus picked was subcultured by successive cell expansion steps to a 24-well plate, a 6-well plate, a T25 flask, and a 125 mL Erlenmeyer flask in that order.

Batch cultures were performed using the obtained humanized antibody Y-expressing monoclones to select a highly expressing monoclone. Subsequently, fed-batch culture was performed in a 125 mL Erlenmeyer flask using the selected humanized antibody Y-expressing monoclone. The basal medium used was G13, and the feed medium used was F13.

Figure 9A:
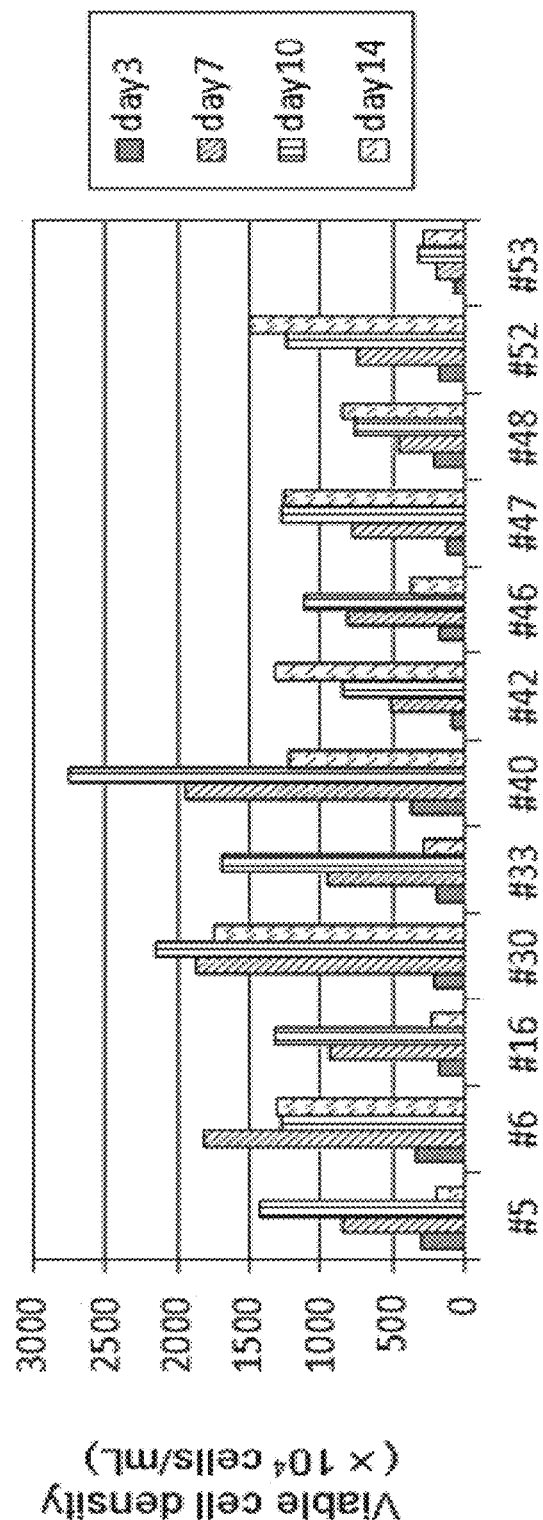
FIG. 9A Results of evaluating the amount of antibody produced in the fed-batch culture of a humanized antibody Y-expressing monoclone obtained using a Hspa5 gene promoter (0.6 kbp) are shown.
Figure 9B:
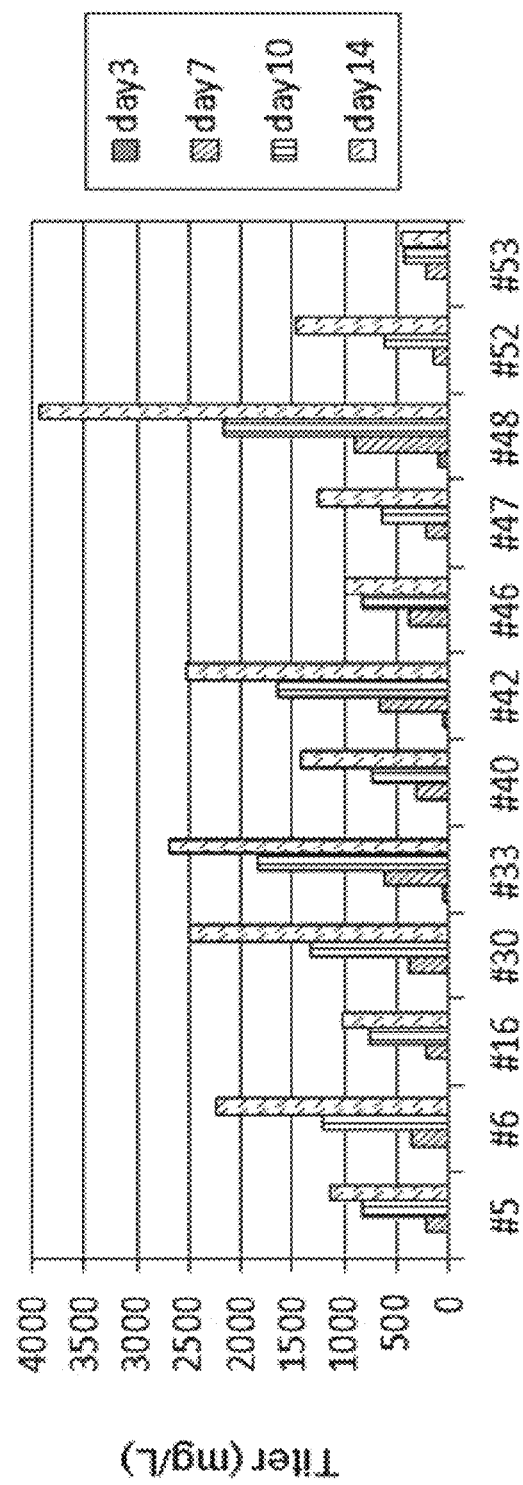
FIG. 9B Results of evaluating the amount of antibody produced in the fed-batch culture of a humanized antibody Y-expressing monoclone obtained using a Hspa5 gene promoter (0.6 kbp) are shown.
Figure 9C:
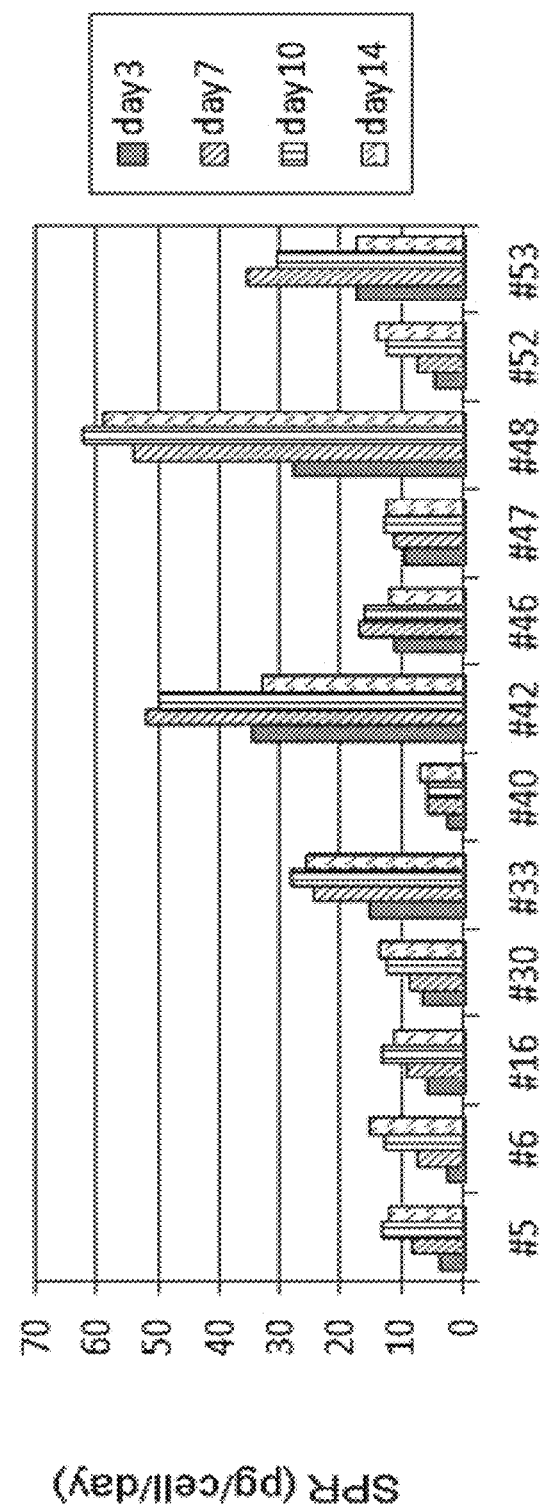
FIG. 9C Results of evaluating the amount of antibody produced in the fed-batch culture of a humanized antibody Y-expressing monoclone obtained using a Hspa5 gene promoter (0.6 kbp) are shown.

Change in the number of viable cells, change in the amount of the antibody produced, and change in the amount of the antibody produced per cell and per day (SPR: specific production rate) are shown in FIGS. 9A, 9B, and 9C, respectively. The amount of the antibody produced per cell and per day was increased at the intermediate stage or later of culture in many clones, as in the stable pool. Among 12 clones evaluated, 5 clones exhibited 2 g/L or more, and #48 had the highest amount of the antibody produced which reached approximately 4 g/L. These results demonstrated that use of the Hspa5 promoter having the optimized promoter length allows highly producing clones to be obtained even without evaluating many clones, and these clones include a clone that exhibits the amount of the antibody produced being as very high as approximately 4 g/L.

(Example 8) Evaluation of Human, Mouse, and Rat Hspa5 Promoters by Fed-Batch Culture with Antibody Expression Level as Indicator 8-1) Construction of Antibody Expression Vector pDSLHA4.1-hHspa5-Y, pDSLHA4.1-mHspa5-Y, and pDSLHA4.1-rHspa5-Y were constructed by substituting the promoter for antibody H chain and L chain genes in the humanized antibody gene Y expression vector pDSLHA4.1-hRPS7-Y with human, mouse, and rat Hspa5 promoters, respectively. In each expression vector, the Hspa5 promoter used was a sequence from a nucleotide approximately 1.0 kbp upstream of the start codon of Hspa5 to the nucleotide immediately upstream of the nucleotide sequence corresponding to the start codon. The nucleotide sequences of the cloned human, mouse, and rat Hspa5 promoters are shown in SEQ ID NOs: 2, 3, and 4, respectively, in the sequence listing.

pDSLHA4.1-hHspa5-Y was constructed by the following method: first, a human Hspa5 promoter was amplified by PCR with human genomic DNA as a template using the primer set given below and PrimeSTAR Max DNA Polymerase, and the PCR product was purified using a QIAquick PCR Purification kit. The purified DNA fragment was digested with NotI-NheI and then inserted into the NotI-NheI sites of H chain gene expression vector pDSH1.1-hRPS7-Y and L chain gene expression vector pDSL2.1-hRPS7-Y to construct pDSH1.1-hHspa5-Y and pDSL2.1-hHspa5-Y, respectively. Next, a DNA fragment obtained by the digestion of pDSL2.1-hHspa5-Y with AatII-HindIII was inserted into the AatII-HindIII site of pDSH1.1-hHspa5-Y to construct pDSLH3.1-hHspa5-Y. DNA element A7 described in Patent Literature 2 was inserted upstream of the expression cassette of pDSLH3.1-hHspa5-Y to construct pDSLHA4.1-hHspa5-Y. pDSLHA4.1-mHspa5-Y and pDSLHA4.1-rHspa5-Y were constructed in the same way as above.

```
Primer set for human Hspa5 promoter
Hspa5-human-NotI-F:
                                   (SEQ ID NO: 29)
GTGTTGCGGCCGCACAGTAGGGAGGGGACTCAGAGC Hspa5-human-NheI-R:
                                   (SEQ ID NO: 30)
GTGGGGCTAGCCTTGCCAGCCAGTTGGGCAGCAG Primer set for mouse Hspa5 promoter
Hspa5-mouse-NotI-F:
                                   (SEQ ID NO: 31)
GGTGGGCGGCCGCATGGTGGAAAGTGCTCGTTTGACC Hspa5-mouse-XbaI-R:
                                   (SEQ ID NO: 32)
GGTGGTCTAGAGCCGGCGCTGAGGACCAGTCGCTC Primer set for rat Hspa5 promoter
Hspa5-rat-NotI-F:
                                   (SEQ ID NO: 33)
GGTGAGCGGCCGCCTCAACGGAGAAGGGCTCCGGAC Hspa5-rat-XbaI-R:
                                   (SEQ ID NO: 34)
GGTAGGTCTAGACTTGCCGGCGCTGTGGACCAGTC
```

8-2) Generation of Humanized Antibody Y-Expressing Stable Pool

The CHO-O1 cells described in (1-2) were transfected with the antibody expression vector pDSLHA4.1-Hspa5-1.1-Y, pDSLHA4.1-Hspa5-0.6-Y, pDSLHA4.1-hHspa5-Y, pDSLHA4.1-mHspa5-Y, or pDSLHA4.1-rHspa5-Y constructed in (7-1) or (8-1), according to the method described in (4-1). Then, drug selection culture was performed by the method described in (5-2) to generate a humanized antibody Y-expressing stable pool. The stable pool was generated at N=2 with each antibody expression vector.

8-3) Evaluation of Amount of Antibody Produced by Fed-Batch Culture of Humanized Antibody Y-Expressing Stable Pool Fed-batch culture was performed in a 125 mL Erlenmeyer flask using each humanized antibody Y-expressing stable pool generated in (8-2). The basal medium used was G13, and the feed medium used was F13.

Figure 10A:
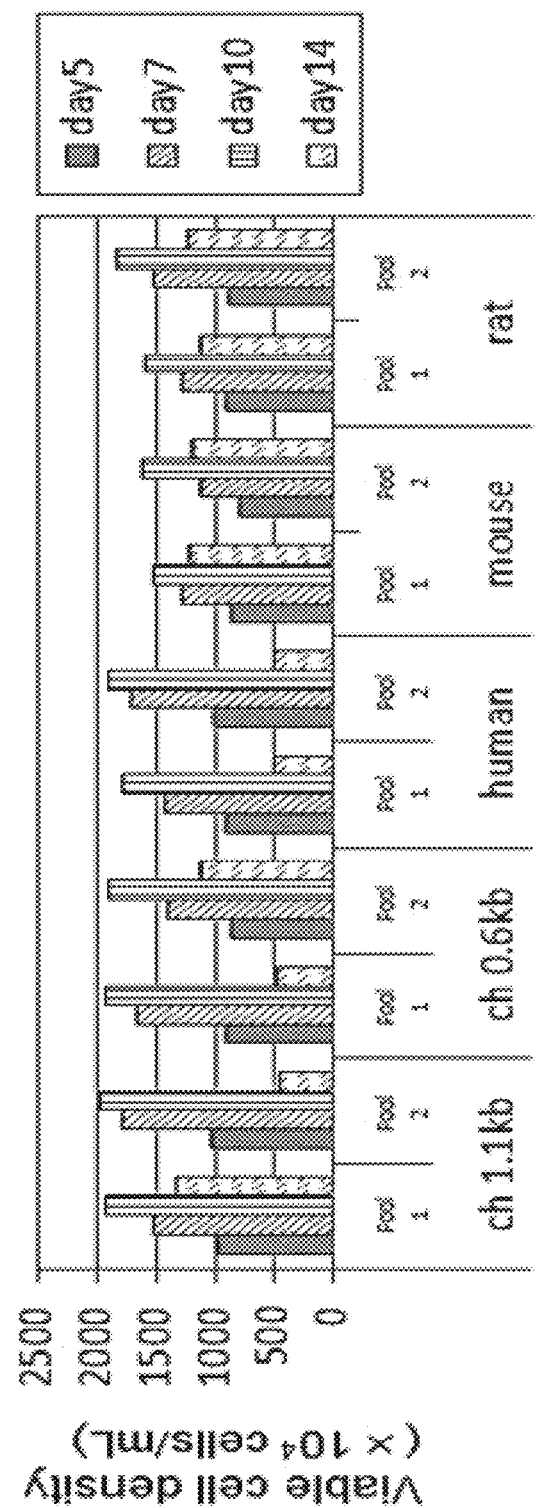
FIG. 10A The amount of antibody produced in the fed-batch culture of a humanized antibody Y-expressing stable pool generated using a Hspa5 gene promoter was compared between species from which the Hspa5 gene promoter was derived.
Figure 10B:
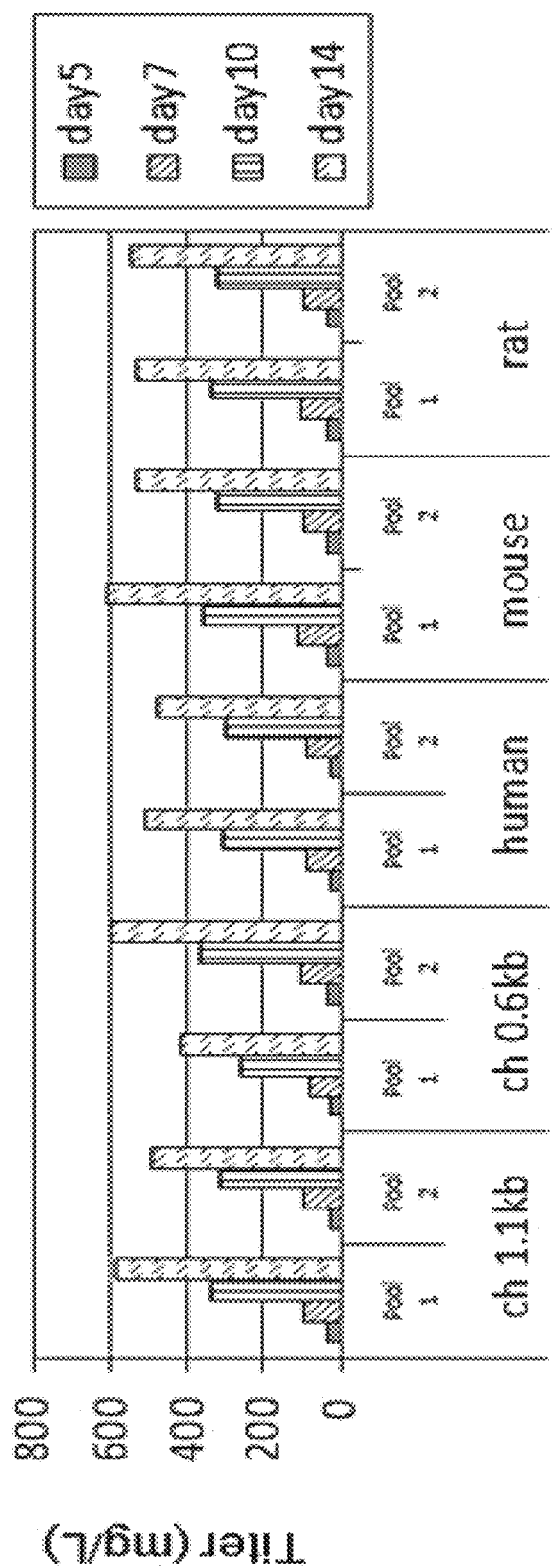
FIG. 10B The amount of antibody produced in the fed-batch culture of a humanized antibody Y-expressing stable pool generated using a Hspa5 gene promoter was compared between species from which the Hspa5 gene promoter was derived.
Figure 10C:
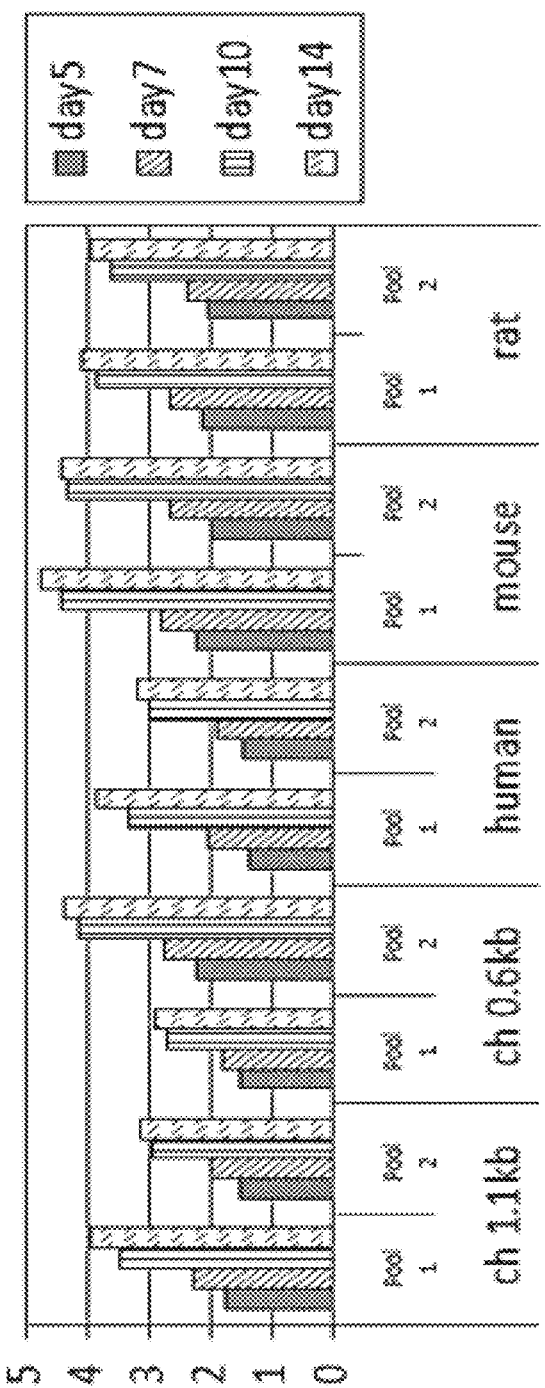
FIG. 10C The amount of antibody produced in the fed-batch culture of a humanized antibody Y-expressing stable pool generated using a Hspa5 gene promoter was compared between species from which the Hspa5 gene promoter was derived.

Change in the number of viable cells, change in the amount of the antibody produced, and change in the amount of the antibody produced per cell and per day (SPR: specific production rate) are shown in FIGS. 10A, 10B, and 10C, respectively. The amount of the antibody produced per cell and per day was increased at the intermediate stage or later of culture in the stable pool generated using any of the human, mouse, and rat Hspa5 promoters, as in the Chinese hamster Hspa5 promoter. Thus, these stable pools were able to achieve production of a high amount of the antibody. These results suggested that antibody productivity can be increased by use of any of the human, mouse, rat, and Chinese hamster Hspa5 promoters, and the effect does not depend on the organism.

(Example 9) Study on Effect Brought about by Combination of Hspa5 Promoter and A7 with Antibody Expression Level as Indicator in Fed-Batch Culture 9-1) Generation of Humanized Antibody Y-Expressing Stable Pool The CHO-O1 cells described in (1-2) were transfected with the DNA element A7-containing antibody expression vector pDSLHA4.1-Hspa5-1.1-Y or pDSLHA4.1-Hspa5-0.6-Y constructed in (7-1), or DNA element A7-free antibody expression vector pDSLH3.1-Hspa5-1.1-Y or pDSLH3.1-Hspa5-0.6-Y, according to the method described in (4-1). Then, drug selection culture was performed by the method described in (5-2) to generate a humanized antibody Y-expressing stable pool. The stable pool was generated at N=2 with each antibody expression vector.

9-2) Evaluation of Amount of Antibody Produced by Fed-Batch Culture of Humanized Antibody Y-Expressing Stable Pool Fed-batch culture was performed in a 125 mL Erlenmeyer flask using each humanized antibody Y-expressing stable pool generated in (9-1). The basal medium used was G13, and the feed medium used was F13.

Figure 11A:
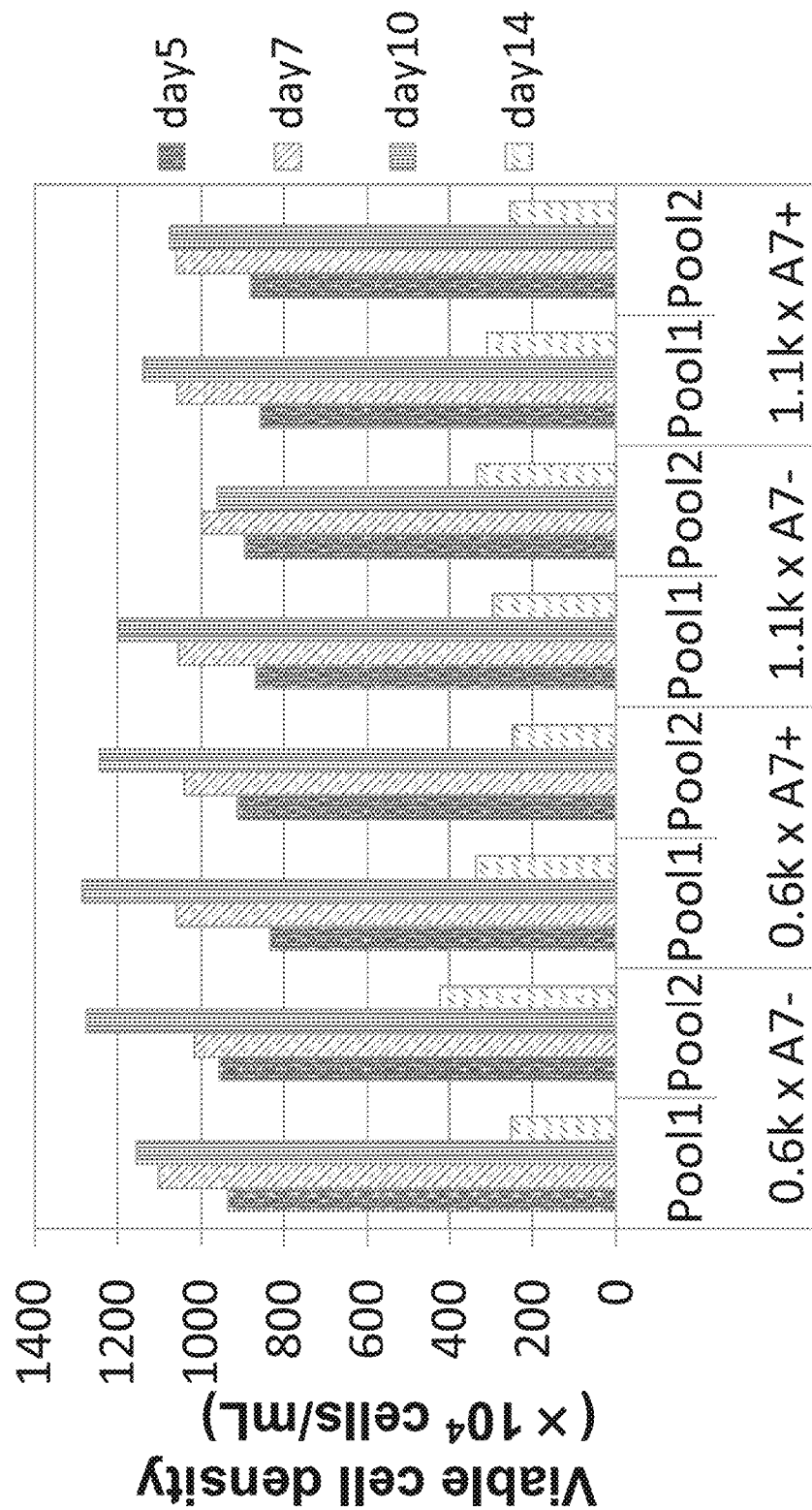
FIG. 11A The amount of antibody produced in the fed-batch culture of a stable pool generated using a humanized antibody Y expression vector containing or not containing DNA element A7 was compared between the presence and absence of the DNA element A7.
Figure 11B:
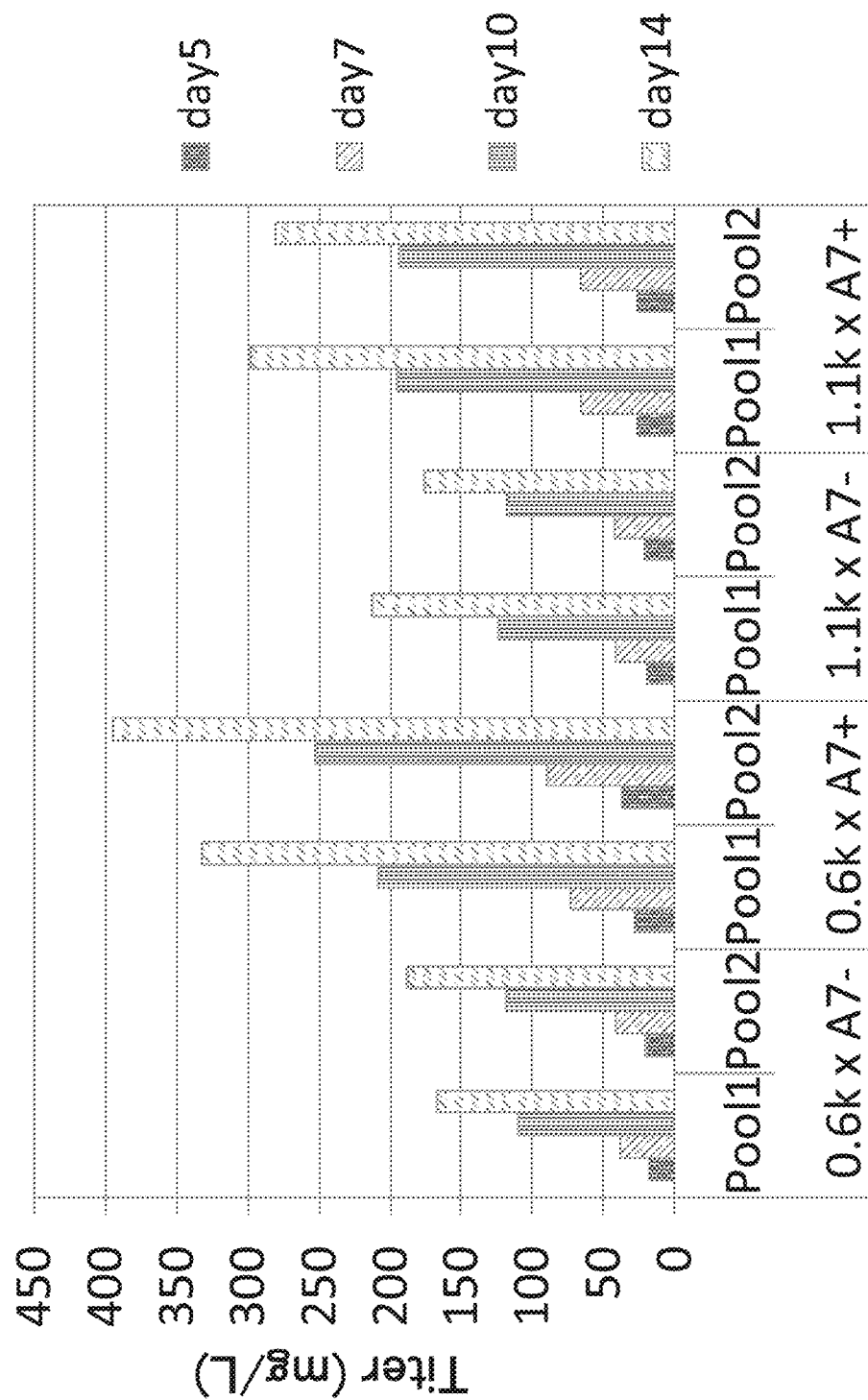
FIG. 11B The amount of antibody produced in the fed-batch culture of a stable pool generated using a humanized antibody Y expression vector containing or not containing DNA element A7 was compared between the presence and absence of the DNA element A7.
Figure 11C:
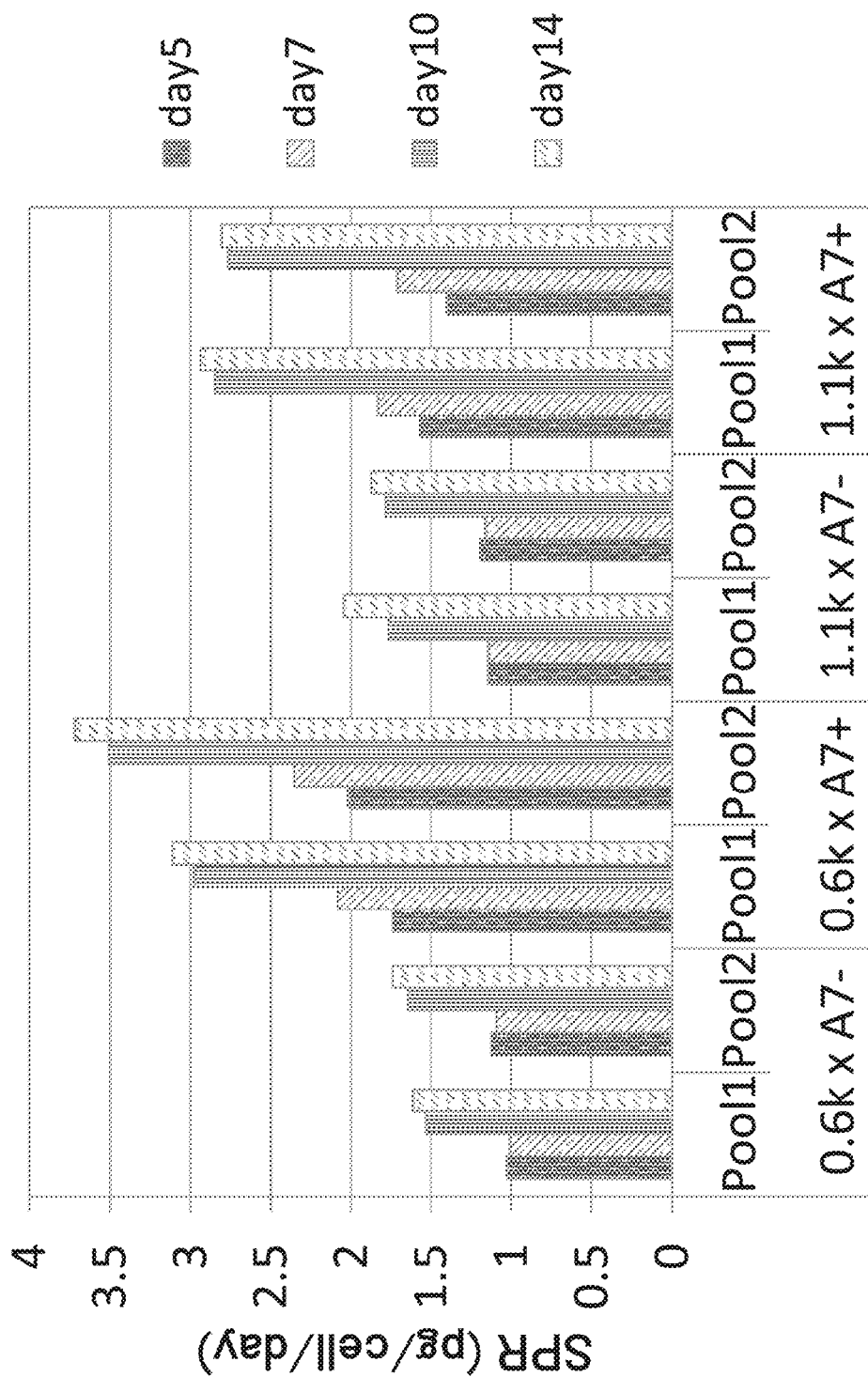
FIG. 11C The amount of antibody produced in the fed-batch culture of a stable pool generated using a humanized antibody Y expression vector containing or not containing DNA element A7 was compared between the presence and absence of the DNA element A7.

Change in the number of viable cells, change in the amount of the antibody produced, and change in the amount of the antibody produced per cell and per day (SPR: specific production rate) are shown in FIGS. 11A, 11B, and 11C, respectively. In the case of using any of the 0.6 and 1.1 kbp Hspa5 promoters, both the amount of the antibody produced and the amount of the antibody produced per cell and per day were higher for the A7-containing antibody expression vector than for the A7-free antibody expression vector. On day 14, the amounts of the antibody produced for the 0.6 and 1.1 kbp Hspa5 promoters combined with A7 were 2.1 and 1.5 times, respectively, the values for the 0.6 and 1.1 kbp Hspa5 promoters without A7. The amount of the antibody produced per cell and per day was increased at the intermediate stage or later of culture, regardless of the presence or absence of A7. These results demonstrated that combined use of the Hspa5 promoter with DNA element A7 effectively achieves high production by synergistic effects.

INDUSTRIAL APPLICABILITY

The method for producing a foreign gene according to the present invention is capable of increasing the productivity of a foreign gene such as a therapeutic protein or an antibody. Particularly, the productivity can be increased by the production method of the present invention using a heat-shock protein A5 gene promoter that permits strong expression of a foreign gene throughout the culture period of cultured mammalian cells without attenuating a foreign gene expression regulation function throughout the culture period of mammalian cells.

Sequence Listing Free Text
SEQ ID NO: 1—Chinese hamster-derived Hspa5 promoter
SEQ ID NO: 2—Human-derived Hspa5 promoter
SEQ ID NO: 3—Mouse-derived Hspa5 promoter
SEQ ID NO: 4—Rat-derived Hspa5 promoter
SEQ ID NO: 5—Nucleotide sequence of Chinese hamster-derived Hspa5 promoter from a nucleotide approximately 2.5 kbp upstream of the start codon of Chinese hamster Hspa5 to the nucleotide immediately upstream of the nucleotide sequence corresponding to the start codon
SEQ ID NO: 6—Nucleotide sequence of Chinese hamster-derived Hspa5 promoter from a nucleotide approximately 2.0 kbp upstream of the start codon of Chinese hamster Hspa5 to the nucleotide immediately upstream of the nucleotide sequence corresponding to the start codon
SEQ ID NO: 7—Nucleotide sequence of Chinese hamster-derived Hspa5 promoter from a nucleotide approximately 1.5 kbp upstream. of the start codon. of Chinese hamster Hspa5 to the nucleotide immediately upstream. of the nucleotide sequence corresponding to the start codon
SEQ ID NO: 8—Nucleotide sequence of Chinese hamster-derived Hspa5 promoter from a nucleotide approximately 1.1 kbp upstream of the start codon of Chinese hamster Hspa5 to the nucleotide immediately upstream of the nucleotide sequence corresponding to the start codon
SEQ ID NO: 9—Nucleotide sequence of Chinese hamster-derived Hspa5 promoter from a nucleotide approximately 0.6 kbp upstream of the start codon of Chinese hamster Hspa5 to the nucleotide immediately upstream of the nucleotide sequence corresponding to the start codon
SEQ ID NO: 10—Primer Hspa5-KpnI-F for Hspa5 promoter
SEQ ID NO: 11—Primer Hspa5-HindIII-R for Hspa5 promoter
SEQ ID NO: 12—Primer hEF1α-NheI-F for hEF1α promoter
SEQ ID NO: 13—Primer hEF1α-HindIII-R for hEF1α promoter
SEQ ID NO: 14—Primer Hspa5-NotI-F for Hspa5 promoter
SEQ ID NO: 15—Primer Hspa5-XbaI-R for Hspa5 promoter
SEQ ID NO: 16—Primer hEF1α-NotI-F for hEF1α promoter
SEQ ID NO: 17—Primer hEF1α-NheI-R for hEF1α promoter
SEQ ID NO: 18—Primer HC-F for the H chain gene of humanized antibody Y
SEQ ID NO: 19—Primer HC-R for the H chain gene of humanized antibody Y
SEQ ID NO: 20—Primer Gapdh-F for Gapdh gene
SEQ ID NO: 21—Primer Gapdh-R for Gapdh gene
SEQ ID NO: 22—Primer hRPS7-XhoI-F for hRPS7 promoter
SEQ ID NO: 23—Primer hRPS7-HindIII-R for hRPS7 promoter
SEQ ID NO: 24—Primer Hspa5-NotI-2500F for Hspa5 promoter 2.5 kbp
SEQ ID NO: 25—Primer Hspa5-NotI-2000F for Hspa5 promoter 2.0 kbp
SEQ ID NO: 26—Primer Hspa5-NotI-1500F for Hspa5 promoter 1.5 kbp
SEQ ID NO: 27—Primer Hspa5-NotI-1100F for Hspa5 promoter 1.1 kbp
SEQ ID NO: 28—Primer Hspa5-NotI-600F for Hspa5 promoter 0.6 kbp
SEQ ID NO: 29—Primer Hspa5-human-NotI-F for human Hspa5 promoter
SEQ ID NO: 30—Primer Hspa5-human-NheI-R for human Hspa5 promoter
SEQ ID NO: 31—Primer Hspa5-mouse-NotI-F for mouse Hspa5 promoter
SEQ ID NO: 32—Primer Hspa5-mouse-XbaI-R for mouse Hspa5 promoter
SEQ ID NO: 33—Primer Hspa5-rat-NotI-F for rat Hspa5 promoter
SEQ ID NO: 34—Primer Hspa5-rat-XbaI-R for rat Hspa5 promoter
SEQ ID NO: 35—Nucleotide sequence of DNA element A2
SEQ ID NO: 36—Nucleotide sequence of DNA element A7
SEQ ID NO: 37—Nucleotide sequence of DNA element A18

The invention claimed is:

1. A polynucleotide consisting of a nucleotide sequence selected from (a) to (f):
   (a) a polynucleotide consisting of the nucleotide sequence of SEQ ID NO: 1;
   (b) a polynucleotide consisting of nucleotides 444 to 2949 of SEQ ID NO: 1 as set forth in the nucleotide sequence of SEQ ID NO: 5;
   (c) a polynucleotide consisting of nucleotides 944 to 2949 of SEQ ID NO: 1 as set forth in the nucleotide sequence of SEQ ID NO: 6;
   (d) a polynucleotide consisting of nucleotides 1443 to 2949 of SEQ ID NO: 1 as set forth in the nucleotide sequence of SEQ ID NO: 7;
   (e) a polynucleotide consisting of nucleotides 1841 to 2949 of SEQ ID NO: 1 as set forth in the nucleotide sequence of SEQ ID NO: 8; and
   (f) a polynucleotide consisting of nucleotides 2341 to 2949 of SEQ ID NO: 1 as set forth in the nucleotide sequence of SEQ ID NO: 9.

2. The polynucleotide according to claim 1, which consists of the nucleotide sequence shown in SEQ ID NO: 1.

3. The polynucleotide according to claim 1, which consists of nucleotides 444 to 2949 of SEQ ID NO: 1 as set forth in the nucleotide sequence of SEQ ID NO: 5.

4. The polynucleotide according to claim 1, which consists of nucleotides 944 to 2949 of SEQ ID NO: 1, as set forth in SEQ ID NO: 6.

5. The polynucleotide according to claim 1, which consists of nucleotides 1443 to 2949 of SEQ ID NO: 1, as set forth in SEQ ID NO: 7.

6. The polynucleotide according to claim 1, which consists of nucleotides 1841 to 2949 of SEQ ID NO: 1, as set forth in SEQ ID NO: 8.

7. The polynucleotide according to claim 1, which consists of nucleotides 2341 to 2949 of SEQ ID NO: 1, as set forth in SEQ ID NO: 9.

8. A polynucleotide consisting of a nucleotide sequence having 95% or higher identity to the nucleotide sequence according to claim 1, the polynucleotide having promoter activity.

9. A polynucleotide consisting of a nucleotide sequence having 99% or higher identity to the nucleotide sequence according to claim 1, the polynucleotide having promoter activity.

10. A polynucleotide that hybridizes under stringent conditions to a polynucleotide consisting of a nucleotide sequence complementary to the nucleotide sequence according to claim 1, the polynucleotide having promoter activity, and wherein the stringent conditions comprise (a) a hybridization solution at 68 degrees Celsius, or (b) a DNA-immobilized filter with 0.7 to 1.0 M NaCl at 68 degrees Celsius and the hybridized polynucleotides are washed at 68 degrees Celsius with a 0.1× to 2× saline-sodium citrate (SSC) solution.

11. A foreign gene expression unit comprising the polynucleotide according to claim 1 and a foreign gene.

12. The foreign gene expression unit according to claim 11, wherein the foreign gene is a gene encoding a multimeric protein.

13. The foreign gene expression unit according to claim 11, wherein the foreign gene is a gene encoding a heteromultimeric protein.

14. The foreign gene expression unit according to claim 11, wherein the foreign gene is a gene encoding an antibody or an antigen-binding fragment thereof.

15. A foreign gene expression vector comprising the foreign gene expression unit according to claim 11.

16. A foreign gene expression vector comprising the foreign gene expression unit according to claim 11 and any one or more polynucleotides selected from polynucleotides (a) to (e) of the following group A:

group A (a) a polynucleotide consisting of the nucleotide sequence of SEQ ID NO: 35 in the sequence listing, (b) a polynucleotide consisting of the nucleotide sequence of SEQ ID NO: 36 in the sequence listing, (c) a polynucleotide consisting of the nucleotide sequence of SEQ ID NO: 37 in the sequence listing, (d) a polynucleotide consisting of a nucleotide sequence having 95% or higher identity to the nucleotide sequence of any one of the polynucleotides (a) to (c), the polynucleotide having foreign gene expression-enhancing activity, and (e) a polynucleotide consisting of a nucleotide sequence having 99% or higher identity to the nucleotide sequence of any one of the polynucleotides (a) to (c), the polynucleotide having foreign gene expression-enhancing activity.

17. A transformed cell into which the foreign gene expression vector according to claim 15 has been introduced.

18. The transformed cell according to claim 17, wherein the cell is a cultured cell derived from a mammal.

19. The transformed cell according to claim 18, wherein the cultured cell derived from a mammal is a COS-1 cell, a 293 cell, or a CHO cell.

20. A method for producing a foreign gene-derived protein, comprising culturing the transformed cell according to claim 17, and obtaining the foreign gene-derived protein from the culture.

* * * * *

SEQUENCE LISTING

```
<160> NUMBER OF SEQ ID NOS: 37

<210> SEQ ID NO 1
<211> LENGTH: 2949
<212> TYPE: DNA
<213> ORGANISM: Cricetulus griseus

<400> SEQUENCE: 1
tatagcccag gcacacatga acttgtaatc ctcctgcttc agcctcttca gtagctgggg      60
ttacaggcct accactaggt gtggctcagg tatcactttt ttaaatgtta caaaaattgg     120
```

```
tgcaagtact tcattaatca aaaaacaggc tgaaattgag ttttgtattt tagtggaaat      180
agactgtgat acagatgtgc ttgaaatgac atgaagctgt gatgtggtca atagtgatt      240 tttttctttc atttcttctt cttgttctta ctcttttttc atataggggtt tcaatatgca     300 gctctggaac tatttagacc aggatggcct tgaattcaag agatccctct gcttctgcct      360
cccttgtgct gagattaaag tcatgagcca ccatatccgg ctgtagtctc ctttaaaatt      420
caagccaaaa gtatctgcaa agatggtcgg tggttaagag cactggctgc tctttcatgg      480
gaccagggat taaaggcatg cagcagtaaa ctgggcttag tgacttctgt cttcatactg      540
gactggtaca gtcccaagga agatcaatgt tatgacagta ttacaagcct tactgaaagt      600
ggtgtatgat gcaacatctg tagaaaagat ggtgttgact gagtcaccaa cataaccttt      660
gaggaacaag aaaggagaaa ttcctgaaca gtgactcaca agctcacatt ttagtgaact      720
gtgtgtaatg ttccagtagt attcagacag tctacttatg aagctcaaga tacatttaat      780
gggaatactg gagtcatttc ctgcccgtga caacatccta agcatctcct ataagcatgt      840
atataagtaa gcacatggga ggcagagaca gtagatctga gagctccatc ccaggggatg      900
gatatcagtc agttgcctag catgcacaga atcttgggtc aagtcccaac tggacacagt      960
aatgtatgcc tattagtccc aacacttgga aggtattggc agaaggttca ggagttcaaa     1020
gtcatctgct acaaagtgtt gaggctagcc tgggttacat gagtctccat ctttaaaaaa     1080
agaaaaaagt ggggctggaa agatggctca gtggttaaga gcaccgcctg ctcttccaaa     1140
ggtcctgagt tcaattccca gcaaccacat ggtggctcaa aaccatctgt agtgaaatct     1200
ggtgccctct gtgtacaaga taaatgaatg aatcttaaaa aaaaaagtca gtgggtggtg     1260
gtggcgcaca ccttagtccc agcactcgg gagaggcagg tgtgagttcg agaccagcct      1320
ggtctacaag agctacttcc aggacaaagc ctccaaagcc acagagaaac cctgtctcga     1380
aaaaccaaac caaccaaac caaaaaagtc aatagcataa gctacagatc aaccaggtta     1440
tcaattctac ctgtaccact caccagtgac tattctattt agccaccccc cccccaatga     1500
tctcttctgg aaaatgggaa acatctacca agaattaatc aaaggactaa atgcacatg      1560 caaaaaaaaa aaaaccttag aacagtgttt taagcaggat aagtagttca agaccagttt     1620
ggaccatgtc tcaaaactaa aggaacaacg aagtacattt agtatttttt gcaacatgtt     1680
attattacat agcatcagga agacaatttt ttctttgtct gctaaatgcc tttgtcatat     1740
cagacctatt tcaagagtca ggatagaatg gtgtcaagaa gggatgagga aggacttgta     1800
aattataacc aagccacaaa tgaaaatgat agacaaggat cgggaacatt atggggcgac     1860
aagctagaga aaaaaatga tatattccag ggtggaaagt gctcgcttga ctattcatag     1920
aacagaatag ccacagcata gcgggggggct cagtactagg ttgcaaatgg ccaggccaat     1980
tctgggactt aaccccaaga aaagaaaaat tggcaaggcc aggatagaca aatgcagctg     2040
gcctaggggt gaagggaaaa cagttggctg agaagagcca cgattcgcag agaggcagaa     2100
cacagactag gacccagctc gagacgtgca ggccgggtgg gtaacataga gcccgggcgc     2160
tcggctaccc gagaacgtga gggaggcttg gaagggcaga gatgcgttcc caggcgacca     2220
cagcatctat gctgaggctg agcagctcgg gacccgaggg gacttaggag gagaaaaggc     2280
cgcatactgc ttcggggtaa gggacagacc ggggaaggac ccaagtccca ccgcccagag     2340
ggaactgaca cgcagacccc gcagcagtcc ccggggggccg ggtgacggga ggacctggac     2400
ggttaccggc ggaaacggtc tcgggttgag aggtcacctg agggacaggc agctgctgaa     2460
```

| | |
|---|---:|
| ccaataggac cggcgcacag gcggatgct gcctctcatt ggcggccgtt gagagtaacc | 2520 |
| agtagccaat gagtcagccc gggggggcgta gcggtgacgt aagttgcgga ggaggccgct | 2580 |
| tcgaatcggc agcggccagc ttggtggcat ggaccaatca gcgtcctcca acgagaagcg | 2640 |
| ccttcaccaa tcggaggcct ccacgacggg gctgggggga gggtatataa gccaagtcgg | 2700 |
| cggcggcgcg ctccacactg gccaagacaa cagtgaccgg aggacctgcc tttgcggctc | 2760 |
| cgagaggtaa gcgccgcggc ctgctcttgc cagacctcct ttgagcctgt ctcgtggctc | 2820 |
| ctcctgaccc gggggggcttc tgtcgccctc agatcggaac gccgccgcgc tccgggacta | 2880 |
| cagcctgttg ctggacttcg agactgcaga cggaccgacc gctgagcact ggcccacagc | 2940 |
| gccggcaag | 2949 |

```
<210> SEQ ID NO 2
<211> LENGTH: 999
<212> TYPE: DNA
<213> ORGANISM: Homo sapiens

<400> SEQUENCE: 2
```

| | |
|---|---:|
| acagtaggga gggactcag agctggaggc aattcctttg gccgggcttg tcctgcgact | 60 |
| taccgtgggg cagcgcaatg tggagaggcc tggtaaaatg gctgggcaag ggtgcggagg | 120 |
| ggacataact ggcaggaagg agtcatgatt cgtggtcgaa cagagtccag accagctcga | 180 |
| cctgtgagca acgaacggcc ctgagactcg cataccccaa taccggtagt ggccgtgaag | 240 |
| ggcaaagaaa tgtgttctga ggcgatccca gcatctaagc tgcgactggt ctactcagag | 300 |
| actggatgga agctgggaag agaaagctgc ttcccgcttc ggggtgaggg atggaggaag | 360 |
| ggagaacaag cagtagagaa ggaaaagttt cagatcccac agccccgggg ggtcactcct | 420 |
| gctggatcta ctccgacccc ctagggccgg gagtgaaggc gggacttgtg cggttaccag | 480 |
| cggaaatgcc tcggggtcag aagtcgcagg agagatagac agctgctgaa ccaatgggac | 540 |
| cagcggatgg ggcggatgtt atctaccatt ggtgaacgtt agaaacgaat agcagccaat | 600 |
| gaatcagctg gggggggcgga gcagtgacgt ttattgcgga gggggccgct tcgaatcggc | 660 |
| ggcggccagc ttggtggcct gggccaatga acggcctcca acgagcaggg ccttcaccaa | 720 |
| tcggcggcct ccacgacggg gctgggggag ggtatataag ccgagtaggc gacggtgagg | 780 |
| tcgacgccgg ccaagacagc acagacagat tgacctattg gggtgttttcg cgagtgtgag | 840 |
| agggaagcgc cgcggcctgt atttctagac ctgcccttcg cctggttcgt ggcgccttgt | 900 |
| gaccccgggc ccctgccgcc tgcaagtcgg aaattgcgct gtgctcctgt gctacggcct | 960 |
| gtggctggac tgcctgctgc tgcccaactg gctggcaag | 999 |

```
<210> SEQ ID NO 3
<211> LENGTH: 1000
<212> TYPE: DNA
<213> ORGANISM: Mus musculus

<400> SEQUENCE: 3
```

| | |
|---|---:|
| atggtggaaa gtgctcgttt gaccatagta ctgaatctcc gcggcggaga aagggaatag | 60 |
| gttacaattg gccaggccaa tcctgggact taaccccggc aaagggaaga ttcgaaaggc | 120 |
| ctggaaagac acatacggct agccttgggg tgaaggagaa acacggttag ctgagaagca | 180 |
| ccaggattct cagcgaggca gaatccagat caggccccag ctcgagacgt gcaggccggg | 240 |
| cgagtaacag ggcctggact ctgggacatc cgagaacgtg tggaggctgg ggagggcgat | 300 |
| cacagctgag gccgggcagc tcaggacgcg gggaatcgag gaggagaaag gccgcgtact | 360 |

| | |
|---|---|
| tcttcagagt gagagacaga aaaggagacc ccgagggaac tgacacgcag accccactcc | 420 |
| agtccccggg ggcctggcgt gaggggagga cctgaacggt taccggcgga aacggtctcg | 480 |
| gggtgagagg tcacccgaag gacaggcagc tgctgaacca ataggaccag cgctcagggc | 540 |
| ggatgctgcc tctcattggt ggccgttaag aatgaccagt agccaatgag tcagcccggg | 600 |
| gggcgtagca atgacgtgag ttgcggagga ggccgcttcg aatcggcagc agccagcttg | 660 |
| gtggcatgga ccaatcagcg gcctccaacg agtagcgact tcaccaatcg gaggcctcca | 720 |
| cgacggggct gtgggagggt atataaggc gagtcggcga cggcgcgctc gatactggcc | 780 |
| gagacaacac tgacctggac acttgggctt ctgcgtgtgt gtgaggtaag cgccgcggcc | 840 |
| tgctgctagg cctgctccga gtctgcttcg tgtctcctcc tgaccccgag gccctgtcg | 900 |
| ccctcagacc agaaccgtcg tcgcgtttcg gggccacagc tgttgctgg actcctaaga | 960 |
| ctcctgcctg actgctgagc gactggtcct cagcgccggc | 1000 |

<210> SEQ ID NO 4
<211> LENGTH: 1000
<212> TYPE: DNA
<213> ORGANISM: Rutilus rutilus

<400> SEQUENCE: 4

| | |
|---|---|
| ctcaacggag aagggctccg gactaggtta caattggcca ggccaatcct gggacttatc | 60 |
| cccgggaaag ggaaaatcag aaaggcccag aaacatacat acaactagac ttggggtgaa | 120 |
| cgaggagcat gattagctga gaagagccag gattctcagc gaggcagaac ccataccagg | 180 |
| ccccagcccg ggacatgcag gcccgttgag taacagggcc tggacgctgg aacacccgag | 240 |
| aaaagtgccg aggctgggaa gggtgatcac agcatcacag ctgaggccgg gcagctgaag | 300 |
| acatgagtga atctaggaga agaaaggcag cgtacttctt ccgagtgaga gacagaaaga | 360 |
| gaggacccga gtctcacagc cctgaggaa ctgacacgca gaccccactc cagtccccgg | 420 |
| gggcccaacg tgagggggagg acctggacgg ttaccggcgg aaacggtttc caggtgagag | 480 |
| gtcacccgag ggacaggcag ctgctcaacc aataggacca gctctcaggg cggatgctgc | 540 |
| ctctcattgg cggccgttaa gaatgaccag tagccaatga gtcggcctgg ggggcgtacc | 600 |
| agtgacgtga gttgcggagg aggccgcttc gaatcggcag cggccagctt ggtggcatga | 660 |
| accaaccagc ggcctccaac gagtagcgag ttcaccaatc ggaggcctcc acgacggggc | 720 |
| tgcggggagg atatataagc cgagtcggcg accggcgcgc tcgatactgg ctgtgactac | 780 |
| actgacttgg acacttggcc ttttgcgggt ttgagaggta agcgtcgcgg cctgcttcca | 840 |
| ggcctaccct gattttggtt cgtggctcct cctgaccctg agacctctgt cgccctcaga | 900 |
| tcagaaccgt cgtcgcgttt cggggctaca gcctgttgct ggactctgtg agacacctga | 960 |
| ccgaccgctg agcgactgac tggtccacag cgccggcaag | 1000 |

<210> SEQ ID NO 5
<211> LENGTH: 2506
<212> TYPE: DNA
<213> ORGANISM: Cricetulus griseus

<400> SEQUENCE: 5

| | |
|---|---|
| tggtcggtgg ttaagagcac tggctgctct ttcatgggac cagggattaa aggcatgcag | 60 |
| cagtaaactg ggcttagtga cttctgtctt catactggac tggtacagtc ccaaggaaga | 120 |
| tcaatgttat gacagtatta caagccttac tgaaagtggt gtatgatgca acatctgtag | 180 |

-continued

```
aaaagatggt gttgactgag tcaccaacat aacctttgag gaacaagaaa ggagaaattc      240
ctgaacagtg actcacaagc tcacatttta gtgaactgtg tgtaatgttc cagtagtatt      300
cagacagtct acttatgaag ctcaagatac atttaatggg aatactggag tcatttcctg      360
cccgtgacaa catcctaagc atctcctata agcatgtata aagtaagca catgggaggc       420
agagacagta gatctgagag ctccatccca ggggatggat atcagtcagt tgcctagcat      480
gcacagaatc ttgggtcaag tcccaactgg acacagtaat gtatgcctat tagtcccaac      540
acttggaagg tattggcaga aggttcagga gttcaaagtc atctgctaca aagtgttgag      600
gctagcctgg gttacatgag tctccatctt taaaaaaaga aaaagtgggg ctggaaaga      660
tggctcagtg gttaagagca ccgcctgctc ttccaaaggt cctgagttca attcccagca     720
accacatggt ggctcaaaac catctgtagt gaaatctggt gccctctgtg tacaagataa     780
atgaatgaat cttaaaaaaa aaagtcagtg ggtggtggtg gcgcacacct ttagtcccag     840
cactcgggag aggcaggtgt gagttcgaga ccagcctggt ctacaagagc tacttccagg     900
acaaagcctc caaagccaca gagaaaccct gtctcgaaaa accaaaccaa accaaaccaa      960
aaaagtcaat agcataagct acagatcaac caggttatca attctacctg taccactcac     1020
cagtgactat tctatttagc cacccccccc ccaatgatct cttctggaaa atgggaaaca     1080
tctaccaaga attaatcaaa ggactaaatg acacatgcaa aaaaaaaaa accttagaac     1140
agtgttttaa gcaggataag tagttcaaga ccagtttgga ccatgtctca aaactaaagg     1200
aacaacgaag tacatttagt atttttttgca acatgttatt attacatagc atcaggaaga    1260
caatttttc tttgtctgct aaatgccttt gtcatatcag acctatttca agagtcagga     1320
tagaatggtg tcaagaaggg atgaggaagg acttgtaaat tataaccaag ccacaaatga    1380
aaatgataga caaggatcgg gaacattatg gggcgacaag ctagagaaaa aaaatgatat    1440
attccagggt ggaaagtgct cgcttgacta ttcatagaac agaatagcca cagcatagcg   1500
gggggctcag tactaggttg caaatggcca ggccaattct gggacttaac cccaagaaaa    1560
gaaaaattgg caaggccagg atagacaaat gcagctggcc tagggtgaa gggaaaacag    1620
ttggctgaga agagccacga ttcgcagaga ggcagaacac agactaggac ccagctcgag   1680
acgtgcaggc cgggtgggta acatagagcc cgggcgctcg gctacccgag aacgtgaggg   1740
aggcttggaa gggcagagat gcgttcccag gcgaccacag catctatgct gaggctgagc   1800
agctcgggac ccgaggggac ttaggaggag aaaaggccgc atactgcttc ggggtaaggg   1860
acagaccggg gaaggaccca agtcccaccg cccagaggga actgacacgc agaccccgca   1920
gcagtccccg ggggccgggt gacgggagga cctggacggt taccggcgga aacggtctcg   1980
ggttgagagg tcacctgagg gacaggcagc tgctgaacca ataggaccgg cgcacagggc   2040
ggatgctgcc tctcattggc ggccgttgag agtaaccagt agccaatgag tcagcccggg   2100
gggcgtagcg gtgacgtaag ttgcggagga ggccgcttcg aatcggcagc ggccagcttg   2160
gtggcatgga ccaatcagcg tcctccaacg agaagcgcct tcaccaatcg gaggcctcca   2220
cgacggggct gggggaggg tatataagcc aagtcggcgg cggcgcgctc cacactggcc    2280
aagacaacag tgaccggagg acctgccttt gcggctccga gaggtaagcg ccgcggcctg    2340
ctcttgccag acctcctttg agcctgtctc gtggctcctc ctgacccggg gggcttctgt    2400
cgccctcaga tcggaacgcc gccgcgctcc gggactacag cctgttgctg gacttcgaga   2460
ctgcagacgg accgaccgct gagcactggc ccacagcgcc ggcaag                    2506
```

<210> SEQ ID NO 6
<211> LENGTH: 2006
<212> TYPE: DNA
<213> ORGANISM: Cricetulus griseus

<400> SEQUENCE: 6

| | | | | | |
|---|---|---|---|---|---|
| tcccaactgg | acacagtaat | gtatgcctat | tagtcccaac | acttggaagg | tattggcaga | 60 |
| aggttcagga | gttcaaagtc | atctgctaca | aagtgttgag | gctagcctgg | gttacatgag | 120 |
| tctccatctt | taaaaaaaga | aaaagtgggg | gctggaaaga | tggctcagtg | gttaagagca | 180 |
| ccgcctgctc | ttccaaaggt | cctgagttca | attcccagca | accacatggt | ggctcaaaac | 240 |
| catctgtagt | gaaatctggt | gccctctgtg | tacaagataa | atgaatgaat | cttaaaaaaa | 300 |
| aaagtcagtg | ggtggtggtg | gcgcacacct | ttagtcccag | cactcgggag | aggcaggtgt | 360 |
| gagttcgaga | ccagcctggt | ctacaagagc | tacttccagg | acaaagcctc | caaagccaca | 420 |
| gagaaaccct | gtctcgaaaa | accaaaccaa | accaaaccaa | aaaagtcaat | agcataagct | 480 |
| acagatcaac | caggttatca | attctacctg | taccactcac | cagtgactat | tctatttagc | 540 |
| caccccccc | ccaatgatct | cttctggaaa | atgggaaaca | tctaccaaga | attaatcaaa | 600 |
| ggactaaatg | acacatgcaa | aaaaaaaaaa | accttagaac | agtgttttaa | gcaggataag | 660 |
| tagttcaaga | ccagtttgga | ccatgtctca | aaactaaagg | aacaacgaag | tacatttagt | 720 |
| atttttttgca | acatgttatt | attacatagc | atcaggaaga | caatttttttc | tttgtctgct | 780 |
| aaatgccttt | gtcatatcag | acctatttca | agagtcagga | tagaatggtg | tcaagaaggg | 840 |
| atgaggaagg | acttgtaaat | tataaccaag | ccacaaatga | aaatgataga | caaggatcgg | 900 |
| gaacattatg | gggcgacaag | ctagagaaaa | aaatgatat | attccagggt | ggaaagtgct | 960 |
| cgcttgacta | ttcatagaac | agaatagcca | cagcatagcg | gggggctcag | tactaggttg | 1020 |
| caaatggcca | ggccaattct | gggacttaac | cccaagaaaa | gaaaaattgg | caaggccagg | 1080 |
| atagacaaat | gcagctggcc | taggggtgaa | gggaaaacag | ttggctgaga | agagccacga | 1140 |
| ttcgcagaga | ggcagaacac | agactaggac | ccagctcgag | acgtgcaggc | cgggtgggta | 1200 |
| acatagagcc | cgggcgctcg | gctacccgag | aacgtgaggg | aggcttggaa | gggcagagat | 1260 |
| gcgttcccag | gcgaccacag | catctatgct | gaggctgagc | agctcgggac | ccgaggggac | 1320 |
| ttaggaggag | aaaaggccgc | atactgcttc | ggggtaaggg | acagaccggg | gaaggaccca | 1380 |
| agtcccaccg | cccagaggga | actgacacgc | agaccccgca | gcagtccccg | ggggccgggt | 1440 |
| gacgggagga | cctggacggt | taccggcgga | aacggtctcg | ggttgagagg | tcacctgagg | 1500 |
| gacaggcagc | tgctgaacca | ataggaccgg | cgcacagggc | ggatgctgcc | tctcattggc | 1560 |
| ggccgttgag | agtaaccagt | agccaatgag | tcagcccggg | gggcgtagcg | gtgacgtaag | 1620 |
| ttgcggagga | ggccgcttcg | aatcggcagc | ggccagcttg | gtggcatgga | ccaatcagcg | 1680 |
| tcctccaacg | agaagcgcct | tcaccaatcg | gaggcctcca | cgacggggct | gggggagggg | 1740 |
| tatataagcc | aagtcggcgg | cggcgcgctc | cacactggcc | aagacaacag | tgaccggagg | 1800 |
| acctgccttt | gcggctccga | gaggtaagcg | ccgcggcctg | ctcttgccag | acctcctttg | 1860 |
| agcctgtctc | gtggctcctc | ctgacccggg | gggcttctgt | cgccctcaga | tcggaacgcc | 1920 |
| gccgcgctcc | gggactacag | cctgttgctg | gacttcgaga | ctgcagacgg | accgaccgct | 1980 |
| gagcactggc | ccacagcgcc | ggcaag | | | | 2006 |

<210> SEQ ID NO 7
<211> LENGTH: 1507
<212> TYPE: DNA

<213> ORGANISM: Cricetulus griseus

<400> SEQUENCE: 7

| | | | | | |
|---|---|---|---|---|---|
| aattctacct | gtaccactca | ccagtgacta | ttctatttag | ccaccccccc | cccaatgatc | 60 |
| tcttctggaa | aatgggaaac | atctaccaag | aattaatcaa | aggactaaat | gacacatgca | 120 |
| aaaaaaaaa | aaccttagaa | cagtgtttta | agcaggataa | gtagttcaag | accagtttgg | 180 |
| accatgtctc | aaaactaaag | gaacaacgaa | gtacatttag | tattttttgc | aacatgttat | 240 |
| tattacatag | catcaggaag | acaattttt | ctttgtctgc | taaatgcctt | tgtcatatca | 300 |
| gacctatttc | aagagtcagg | atagaatggt | gtcaagaagg | gatgaggaag | gacttgtaaa | 360 |
| ttataaccaa | gccacaaatg | aaaatgatag | acaaggatcg | ggaacattat | ggggcgacaa | 420 |
| gctagagaaa | aaaaatgata | tattccaggg | tggaaagtgc | tcgcttgact | attcatagaa | 480 |
| cagaatagcc | acagcatagc | gggggctca | gtactaggtt | gcaaatggcc | aggccaattc | 540 |
| tgggacttaa | ccccaagaaa | agaaaaattg | gcaaggccag | gatagacaaa | tgcagctggc | 600 |
| ctaggggtga | agggaaaaca | gttggctgag | aagagccacg | attcgcagag | aggcagaaca | 660 |
| cagactagga | cccagctcga | gacgtgcagg | ccgggtgggt | aacatagagc | ccgggcgctc | 720 |
| ggctacccga | gaacgtgagg | gaggcttgga | agggcagaga | tgcgttccca | ggcgaccaca | 780 |
| gcatctatgc | tgaggctgag | cagctcggga | cccgaggga | cttaggagga | gaaaaggccg | 840 |
| catactgctt | cggggtaagg | gacagaccgg | ggaaggaccc | aagtcccacc | gcccagaggg | 900 |
| aactgacacg | cagacccgc | agcagtcccc | ggggccggg | tgacgggagg | acctggacgg | 960 |
| ttaccggcgg | aaacggtctc | gggttgagag | gtcacctgag | ggacaggcag | ctgctgaacc | 1020 |
| aataggaccg | gcgcacaggg | cggatgctgc | ctctcattgg | cggccgttga | gagtaaccag | 1080 |
| tagccaatga | gtcagcccgg | ggggcgtagc | ggtgacgtaa | gttgcggagg | aggccgcttc | 1140 |
| gaatcggcag | cggccagctt | ggtggcatgg | accaatcagc | gtcctccaac | gagaagcgcc | 1200 |
| ttcaccaatc | ggaggcctcc | acgacggggc | tgggggagg | gtatataagc | caagtcggcg | 1260 |
| gcggcgcgct | ccacactggc | caagacaaca | gtgaccggag | gacctgcctt | tgcggctccg | 1320 |
| agaggtaagc | gccgcggcct | gctcttgcca | gacctccttt | gagcctgtct | cgtggctcct | 1380 |
| cctgacccgg | ggggcttctg | tcgccctcag | atcggaacgc | cgccgcgctc | cgggactaca | 1440 |
| gcctgttgct | ggacttcgag | actgcagacg | gaccgaccgc | tgagcactgg | cccacagcgc | 1500 |
| cggcaag | | | | | 1507 |

<210> SEQ ID NO 8
<211> LENGTH: 1109
<212> TYPE: DNA
<213> ORGANISM: Cricetulus griseus

<400> SEQUENCE: 8

| | | | | | |
|---|---|---|---|---|---|
| cgggaacatt | atggggcgac | aagctagaga | aaaaaaatga | tatattccag | ggtggaaagt | 60 |
| gctcgcttga | ctattcatag | aacagaatag | ccacagcata | gcgggggct | cagtactagg | 120 |
| ttgcaaatgg | ccaggccaat | tctgggactt | aaccccaaga | aaagaaaaat | tggcaaggcc | 180 |
| aggatagaca | aatgcagctg | gcctaggggt | gaagggaaaa | cagttggctg | agaagagcca | 240 |
| cgattcgcag | agaggcagaa | cacagactag | gacccagctc | gagacgtgca | ggccgggtgg | 300 |
| gtaacataga | gccgggcgc | tcggctaccc | gagaacgtga | gggaggcttg | gaagggcaga | 360 |
| gatgcgttcc | caggcgacca | cagcatctat | gctgaggctg | agcagctcgg | gacccgaggg | 420 |
| gacttaggag | gagaaaaggc | cgcatactgc | ttcggggtaa | gggacagacc | ggggaaggac | 480 |

```
ccaagtccca ccgcccagag ggaactgaca cgcagacccc gcagcagtcc ccggggccg      540 ggtgacggga ggacctggac ggttaccggc ggaaacggtc tcgggttgag aggtcacctg     600
agggacaggc agctgctgaa ccaataggac cggcgcacag gcggatgct gcctctcatt     660 ggcggccgtt gagagtaacc agtagccaat gagtcagccc ggggggcgta gcggtgacgt     720
aagttgcgga ggaggccgct tcgaatcggc agcggccagc ttggtggcat ggaccaatca     780
gcgtcctcca acgagaagcg ccttcaccaa tcggaggcct ccacgacggg ctgggggga     840 gggtatataa gccaagtcgg cggcggcgcg ctccacactg gccaagacaa cagtgaccgg     900
aggacctgcc tttgcggctc cgagaggtaa gcgccgcggc ctgctcttgc cagacctcct     960
ttgagcctgt ctcgtggctc ctcctgaccc gggggcttc tgtcgccctc agatcggaac     1020
gccgccgcgc tccgggacta cagcctgttg ctggacttcg agactgcaga cggaccgacc     1080
gctgagcact ggcccacagc gccggcaag                                      1109

<210> SEQ ID NO 9
<211> LENGTH: 609
<212> TYPE: DNA
<213> ORGANISM: Cricetulus griseus

<400> SEQUENCE: 9
ggaactgaca cgcagacccc gcagcagtcc ccggggccg ggtgacggga ggacctggac       60
ggttaccggc ggaaacggtc tcgggttgag aggtcacctg agggacaggc agctgctgaa     120
ccaataggac cggcgcacag gcggatgct gcctctcatt ggcggccgtt gagagtaacc     180
agtagccaat gagtcagccc ggggggcgta gcggtgacgt aagttgcgga ggaggccgct     240
tcgaatcggc agcggccagc ttggtggcat ggaccaatca gcgtcctcca acgagaagcg     300
ccttcaccaa tcggaggcct ccacgacggg ctgggggga gggtatataa gccaagtcgg     360
cggcggcgcg ctccacactg gccaagacaa cagtgaccgg aggacctgcc tttgcggctc     420
cgagaggtaa gcgccgcggc ctgctcttgc cagacctcct ttgagcctgt ctcgtggctc     480
ctcctgaccc gggggcttc tgtcgccctc agatcggaac gccgccgcgc tccgggacta     540
cagcctgttg ctggacttcg agactgcaga cggaccgacc gctgagcact ggcccacagc     600
gccggcaag                                                           609

<210> SEQ ID NO 10
<211> LENGTH: 36
<212> TYPE: DNA
<213> ORGANISM: Artificial Sequence
<220> FEATURE:
<223> OTHER INFORMATION: Hspa5-KpnI-F

<400> SEQUENCE: 10
gggggggtac ctatagccca ggcacacatg aacttg                               36

<210> SEQ ID NO 11
<211> LENGTH: 36
<212> TYPE: DNA
<213> ORGANISM: Artificial Sequence
<220> FEATURE:
<223> OTHER INFORMATION: Hspa5-HindIII-R

<400> SEQUENCE: 11
gggggaagct tcttgccggc gctgtgggcc agtgct                               36

<210> SEQ ID NO 12
```

<211> LENGTH: 37
<212> TYPE: DNA
<213> ORGANISM: Artificial Sequence
<220> FEATURE:
<223> OTHER INFORMATION: hEF1??-NheI-F

<400> SEQUENCE: 12
gagtgggcta gcgaattggc tccggtgccc gtcagtg					37

<210> SEQ ID NO 13
<211> LENGTH: 35
<212> TYPE: DNA
<213> ORGANISM: Artificial Sequence
<220> FEATURE:
<223> OTHER INFORMATION: hEF1??-HindIII-R

<400> SEQUENCE: 13
gagtggaagc ttcctcacga cacctgaaat ggaag						35

<210> SEQ ID NO 14
<211> LENGTH: 38
<212> TYPE: DNA
<213> ORGANISM: Artificial Sequence
<220> FEATURE:
<223> OTHER INFORMATION: Hspa5-NotI-F

<400> SEQUENCE: 14 gggggggcggc cgctatagcc caggcacaca tgaacttg					38

<210> SEQ ID NO 15
<211> LENGTH: 36
<212> TYPE: DNA
<213> ORGANISM: Artificial Sequence
<220> FEATURE:
<223> OTHER INFORMATION: Hspa5-XbaI-R

<400> SEQUENCE: 15
gggggtctag acttgccggc gctgtgggcc agtgct						36

<210> SEQ ID NO 16
<211> LENGTH: 39
<212> TYPE: DNA
<213> ORGANISM: Artificial Sequence
<220> FEATURE:
<223> OTHER INFORMATION: hEF1a-NotI-F

<400> SEQUENCE: 16
gagtgggcgg ccgcgaattg gctccggtgc ccgtcagtg					39

<210> SEQ ID NO 17
<211> LENGTH: 35
<212> TYPE: DNA
<213> ORGANISM: Artificial Sequence
<220> FEATURE:
<223> OTHER INFORMATION: hEF1a-NheI-R

<400> SEQUENCE: 17
gagtgggcta gccctcacga cacctgaaat ggaag						35

<210> SEQ ID NO 18
<211> LENGTH: 20
<212> TYPE: DNA
<213> ORGANISM: Artificial Sequence
<220> FEATURE:
<223> OTHER INFORMATION: HC-F

<400> SEQUENCE: 18
tggctgaacg gcaaagagta                                                        20

<210> SEQ ID NO 19
<211> LENGTH: 20
<212> TYPE: DNA
<213> ORGANISM: Artificial Sequence
<220> FEATURE:
<223> OTHER INFORMATION: HC-R

<400> SEQUENCE: 19
ttggccttgg agatggtctt                                                        20

<210> SEQ ID NO 20
<211> LENGTH: 22
<212> TYPE: DNA
<213> ORGANISM: Artificial Sequence
<220> FEATURE:
<223> OTHER INFORMATION: Gapdh-F

<400> SEQUENCE: 20
gtattggacg cctggttacc ag                                                     22

<210> SEQ ID NO 21
<211> LENGTH: 22
<212> TYPE: DNA
<213> ORGANISM: Artificial Sequence
<220> FEATURE:
<223> OTHER INFORMATION: Gapdh-R

<400> SEQUENCE: 21
agtcatactg gaacatgtag ac                                                     22

<210> SEQ ID NO 22
<211> LENGTH: 31
<212> TYPE: DNA
<213> ORGANISM: Artificial Sequence
<220> FEATURE:
<223> OTHER INFORMATION: hRPS7-XhoI-F

<400> SEQUENCE: 22
gggggctcga gtgtatatta acagcacatt a                                           31

<210> SEQ ID NO 23
<211> LENGTH: 31
<212> TYPE: DNA
<213> ORGANISM: Artificial Sequence
<220> FEATURE:
<223> OTHER INFORMATION: hRPS7-HindIII-R

<400> SEQUENCE: 23
gggggaagct tcggctttct cctgggagaa c                                           31

<210> SEQ ID NO 24
<211> LENGTH: 33
<212> TYPE: DNA
<213> ORGANISM: Artificial Sequence
<220> FEATURE:
<223> OTHER INFORMATION: Hspa5-NotI-2500F

<400> SEQUENCE: 24 gggggcggc cgctggtcgg tggttaagag cac                                          33

<210> SEQ ID NO 25
<211> LENGTH: 33
<212> TYPE: DNA

```
<213> ORGANISM: Artificial Sequence
<220> FEATURE:
<223> OTHER INFORMATION: Hspa5-NotI-2000F

<400> SEQUENCE: 25 gggggggcggc cgctcccaac tggacacagt aat                          33

<210> SEQ ID NO 26
<211> LENGTH: 33
<212> TYPE: DNA
<213> ORGANISM: Artificial Sequence
<220> FEATURE:
<223> OTHER INFORMATION: Hspa5-NotI-1500F

<400> SEQUENCE: 26 gggggggcggc cgcaattcta cctgtaccac tca                          33

<210> SEQ ID NO 27
<211> LENGTH: 33
<212> TYPE: DNA
<213> ORGANISM: Artificial Sequence
<220> FEATURE:
<223> OTHER INFORMATION: Hspa5-NotI-1100F

<400> SEQUENCE: 27 gggggggcggc cgccgggaac attatggggc gac                          33

<210> SEQ ID NO 28
<211> LENGTH: 33
<212> TYPE: DNA
<213> ORGANISM: Artificial Sequence
<220> FEATURE:
<223> OTHER INFORMATION: Hspa5-NotI-600F

<400> SEQUENCE: 28 gggggggcggc cgcggaactg acacgcagac ccc                          33

<210> SEQ ID NO 29
<211> LENGTH: 36
<212> TYPE: DNA
<213> ORGANISM: Artificial Sequence
<220> FEATURE:
<223> OTHER INFORMATION: Hspa5-human-NotI-F

<400> SEQUENCE: 29
gtgttgcggc cgcacagtag ggaggggact cagagc                        36

<210> SEQ ID NO 30
<211> LENGTH: 34
<212> TYPE: DNA
<213> ORGANISM: Artificial Sequence
<220> FEATURE:
<223> OTHER INFORMATION: Hspa5-human-NheI-R

<400> SEQUENCE: 30
gtggggctag ccttgccagc cagttgggca gcag                          34

<210> SEQ ID NO 31
<211> LENGTH: 37
<212> TYPE: DNA
<213> ORGANISM: Artificial Sequence
<220> FEATURE:
<223> OTHER INFORMATION: Hspa5-mouse-NotI-F

<400> SEQUENCE: 31
ggtgggcggc cgcatggtgg aaagtgctcg tttgacc                       37
```

<210> SEQ ID NO 32
<211> LENGTH: 35
<212> TYPE: DNA
<213> ORGANISM: Artificial Sequence
<220> FEATURE:
<223> OTHER INFORMATION: Hspa5-mouse-XbaI-R

<400> SEQUENCE: 32
ggtggtctag agccggcgct gaggaccagt cgctc                              35

<210> SEQ ID NO 33
<211> LENGTH: 36
<212> TYPE: DNA
<213> ORGANISM: Artificial Sequence
<220> FEATURE:
<223> OTHER INFORMATION: Hspa5-rat-NotI-F

<400> SEQUENCE: 33
ggtgagcggc cgcctcaacg gagaagggct ccggac                             36

<210> SEQ ID NO 34
<211> LENGTH: 35
<212> TYPE: DNA
<213> ORGANISM: Artificial Sequence
<220> FEATURE:
<223> OTHER INFORMATION: Hspa5-rat-XbaI-R

<400> SEQUENCE: 34
ggtaggtcta gacttgccgg cgctgtggac cagtc                              35

<210> SEQ ID NO 35
<211> LENGTH: 8450
<212> TYPE: DNA
<213> ORGANISM: Homo sapiens

<400> SEQUENCE: 35
attttgcttg aaaggatagc atcaaggaag tgaaatgaca acccacagaa tgagagataa     60
tttttgcaaa tcatgtatct gataaggggac ctgtagtcag aatatgcaaa gaacccttac   120
aattcaataa gacaacccaa tttaaaaaca ggcaaaggat gtgaataggc atttctccaa   180
agatacggaa aaacggccaa taagcacata aaaagatgct caaaatcatt tgccatttgg   240
gaaatgcaat caaaaccaca atgaggtatc acttcacgcc cattagggtg ctatagatc    300 agaaagtcag ataacatgtg ttggcaagca catggaaaca ctgaagtcct tacacactgc   360
tggtaggaat gtaaaatggt gcagccactg tggaaaacag ttttccaatt tctcaaaatg   420
ttaaacacag ttatcataca cccaagcaat tctactctta ggtatatacc caagagaaat   480
gaaaacatat gtcttcacca gaacttgctg ttcacagcag cattatgcat aatagaccaa   540
aagtggaaac aactcaactg cccatcaact ggtgaatgga taagtaaaat gtgatgtaac   600
cagtcattgg actgtcattc attaataaaa agaacaaggt actgattcat gttctaacat   660
gagtgaatct tgaaaacact atgctaaatt aaagaagcca gtcacaaaag gccgtgtatt   720
gcatgatttt atatatacat gaacttttat atatatataa ttatatatat tatatataat   780
tttatatata taaatttcta tatataaata tataaaatca tatatatgat atatattttt   840
tcatatacat catatatatt tacaaaaatt atatatcata tatcatatga tatatgagat   900
atatatcatg atatatatga tatatgatat atatcatatg agatatatga tatcatgaga   960
tatatgatat catatgatat atatgatata gatatcatat gatatatata taatatatat  1020

```
atgatagata tattatatat gatagatatg atagatatca tattatatat gatagatatg    1080
atagatatca tattatatat gatagatata gatatcatat tatatatgat agatatgata    1140
gatatcatat tatatatgat agatatgata gatatcatat tatatatgat agatatgata    1200
gatatcatat tatatatgat agatatgata gatatcatat tatatatgat agatatgata    1260
gatatcatat tatatatgat agatatgata gatatcatat tatatatgat agatatgata    1320
gatatcatat tatatatgat agatatgata gatatcatat tatatatgat agatatgata    1380
gatatcatat tatatatgat agatatgata gatatcatat tatatatgat agatatgata    1440
gatatcatat tatatatgat agatatgata gatatcatat tatatatgat agatatgata    1500
gatatcatat tatatatgat atcatatata taccacatac atcatatata catcatatat    1500
acatcatata tatcatacat atatatgaac tttccagaat aggtatatca ataaagacag    1560
gaagtataca agtggttgcc acagcctgag aggagcaggg aatggtgagt gactgctaat    1620
ggatatggca cttttttggg ggggtgatga aaatgttctg gtcagacaat ggcaattaca    1680
aaactgtata cacacgaaaa accaaagaat cacacacttt aaaagggagg atttagctcg    1740
gcatggtggc atgcgcctgt actcccagtt actcgggagg ctgaagcagg actgcttaga    1800
gcccaggact tcaaggctgc agcgagctat gatcgctcca ctgcactcca acaaggatga    1860
cagtgcgaga cccgttttct aaataataat aataataata ataataaata acccaaggta    1920
cccagttcac atgcaaaacc actggtaaac ataaattatc tccaagtaat ctagaaagaa    1980
aatgagcaca taagacgtct tctaaaaaca cacatatatt tctttacatg ttacatttaa    2040
cgtaaaaatc agctatgcag aagttacatg aacattttat gttggaaagg taaatgacta    2100
ttattaatac agaatggtta agtacattta tgtttttatg tacaaacgca taaaaggaaa    2160
agcatcctta aaataaacac catcaatggc tcctcggtgg tcacaaaaca aaatcctcac    2220
acctttgtct tccttcacaa ttgagcttta tccacctttt caggcttatc tcccattatt    2280
acctgacaca aacttgggtg ggccagagtt tccactgacc atcccccgac tattcatcca    2340
acactatgtt cactgcctcc cattcctgac catttgcctt ttgtcttcaa ctaattctgg    2400
ggacgttttg tccaaataaa tgatccatat tcttgaaggc tggaatcaag tcctattaca    2460
aatatatttt ctcaccctct ccagagcata gcaacccagc atctactggc ctctcacagc    2520
tctaaccatc cacaaccctca agctggcttc tcatcaaacg ggtactttc accacccaaa    2580 ttcaattaat tcactcttac aataatgaag aatagtcgcc tacagcctac cttttccagc    2640
cttgattcaa tcatttatca attttatctt caaagtccct cacttcaggg agatgatata    2700
tcagctttca cccagagtcc taaagaaaac agcactcttg ccaatgacat agtgccacct    2760
agtggcaaca taaggtaaat cacagtggca gtagaaggat ctccacacta cttttacagg    2820
aatgcactgc aggtaaaaaa taagaagcta cagtactgtt tggcaggaca atttgtttca    2880
tacgtgcata ctatcgccct gactaaatta actcgcaagt cttacaggta ttatttgttt    2940
tcagttccat gcacagatta gccatttagt acttactaaa tcaaactcaa tttctgaagt    3000
gtcttacacc aatatattca tgcacatatg gttaaaattt tccttgagga tctatcatgt    3060
gagagtgtgg cttattataa caagtaaaca gaacaaataa atacaaaatg aaaagaaatc    3120
gtatgattta ctcgcatata agggagcttg ttgtggatta agtttcatga cccaggacac    3180
tgaaacagaa atggaataaa tgagaataaa attaaaagtt gtcatcaaaa atatagaagc    3240
catctaaaga cctaggtgtc aagcatagct ctatgagtac aatcccgtgc ctgagattac    3300
catatgccca gctgtatgct atacactaag agatttagga aggaagcggg gtcagggatt    3360
gaccccagac tccatctttt caagtgggga agaaagatct tccgattgaa aaataaaggc    3420
```

```
aaaaaaggct tcaccgtcac agaagtttca acaaccaaca ggatatttaa aacagttatc    3480
aaagcaaaac cattgtatgt tcacttacat ttttacatag tccctcaaac tcacaaaatg    3540
ctgtttactc agggacttct tccggtctta ctagggagcc tggaaagtga cgggaggatt    3600
gcaagggacc actagaaccc tcttcctcaa ttccccttct ctgagaaggg aggctacagc    3660
ttgcctctct aaccactaaa aggcatgacc ctcctcaaag ttaatagccg gattccctga    3720
tagatatttt cactaaatga attctcataa aactctcact aagatttaga gaaggcttcc    3780
agggttgaat tcctgaacat taagaacagc atgttttta aaagtttaac ttggtgattg    3840
gaccaggact tcatctaggc tatgaatgct cagaatggta ggtcctttac caaacagctt    3900
gagtttgtgt ataaagtgat ctcatcctct taagagtcag agaaacagaa ccaagcgact    3960
tcactataat ttgatctgag gaagtttctt actcacaata ggtaaatgaa ggcacatact    4020
aaccagcaat ataacaaca atatcaagtg tcattcacac atgcaaaaaa cagacaaaat    4080
cccaaactct gtgttctaac aaatcgcaaa aacctcacta acaataaatt gaaatgacca    4140
aatgtttgga ctgaaaagca atgccttggt agcctagcca tgcctaactc aaataacaga    4200
accatctcga tgttaaaatc ctcacagatc aagctgtgta tgtctcgggt caagacttcg    4260
ccaaaaagca gtgagcacac acttaagagg gaaaaaatct acctcagcct cctaaatgca    4320
atcatctcta cacgagttgc aggccccaag cttcaacgtg ttctgctgga caacgcagta    4380
gaaagctgac aagcaggtgg ccttcccaca ctgactgaac cacctccatg cccatgtcca    4440
ttcattttct tgcccacccc atgtgctata acagacctcc tggctcaggg cactcttttcc   4500 ttcctgactg ccttcactta atgactttgt acttttaggt gcaaaaatta tctgcagaaa    4560
tccacactga aaaccaagct tgagaaaggc agcaataacc aacatttta caagaagaac    4620 aaggtcaata tcaagcccat cagattcaaa tagcaagcat ggatgaaaat gaaagattga    4680
aaggcttgag tgccttctta atgtattaaa tatccattta atttacaatt aagctcactg    4740
tgctcactgg cctttaatc agcttccag gtcctgctca gcttgccta ggacatggga    4800 atgaaagaac ctatacattt atggaccaat ctaccttaac taacttgtca agtgttcctg    4860
catcaagcag aagaaacatc agtgaaactg atacaggaat taacccttg ttaatccata    4920 aaacttaaag gagcgggatc caatcttctg gcttccctgg ccacgctgg aagaagaatt    4980 gtcttgcgcc acacataaaa tacacgaaca ctaataatag ctgctaagct ttaaaaaat    5040 tgcaaaaaag gaaatctca taatttttg tttgttgtga ggtggagcct cactctgtca    5100
cccaggccga gtgcagtgg caccatcttg gctcactgca acctctgcct cctgggttca    5160
agccattctc ctgcctcagc ctcccgagta gctgggatga taggcgtgtg ccaccatgcc    5220
cagctaattt tcgtattttt agtagagacg gggtttcacc atgttggcca ggctggtctc    5280
aaactcctga cctcaggtga tccacccacc tcggcctccc aaagtgctgg gattacaggt    5340
gtgagccacc gtgcccggcc aatgttttaa gaacgtttac gaatttgtat tgggccacat    5400
tcaaagcctt cacaggctgc atgcagcctg caggccgcgg ttggacaagc ttggattaga    5460
gaaatctaca gagacaaact agtgacttag tagccctctg atagctcatg atttgcaaga    5520
aacttaggat gactatgtgt aaagaccaca aacatcaatt taactgaatg gttcccgcca    5580
cactggaatg aggaagctga gcaaactcag aggactctaa gaaagggctg atgtcatctg    5640
aactgttcgg aattataaac tcctctaaac atgtttcaaa gccagaactt gtaggagttg    5700
ttctgataca cggattaaaa gagggatgac aaagtgtctg tcccccacac tggtcaaagg    5760
```

```
gacaggtcat tgttatgctg gcaatgcagg ctgctgaaaa gaatgtatct gtcaaaagta      5820
atcaaagtaa tgaccccaga aggctccaga aacagactgg taaattcagg ttgcttcag       5880 acttccacaa tgctggcaca caaggggaaa gacaaaacta acatttacag agcattatat     5940
ttgatattac atttaatccc cattaaaaag atactatttc ccgtttcact agtgaaaaag      6000
ttgatctttc aaaggttaaa ttatttaaca ccaaggtcaa agggtaagtt ggagagacca      6060
gattcaaacc cagtctgaca ttaaaacatg tgttttcccc ccacatcgtc tcctgctaat     6120
aacctcaaat ctaaaaactg acttgcccta caccttgagc cccatcctac aaactctccc     6180
tgacgttatt aattcagctg tcactgtgca cctacaacgt gccagacacc atactcctca    6240
acactctgta ggcacagaag gaacagataa aaatccctac cttcatagat attattctag    6300
gggtaacaca ggtaaataaa acattaaaat agttttcaca tagtagcaaa ttccatatag   6360
caaaataaaa cagaagaagg aatagcaaat gagggagatg ccctcttaaa catggtgctg    6420
agggaaggcc tccctgagaa agatatcatt taccccaaaa ataaaaaagc aagtaataga   6480
aaaaacaggt aaaaggtgtt ctagacactt aaacctgcca cattgagaac tcagggttct    6540
gatgcaaaac ctcgctgcat agaatgcatt aacttatttt tatacattta aacaaacaaa    6600
ctctacttaa gaactgtgtt ctaaaggaag gagcatatta caggaaggca atttttggtc    6660
agagtagaca cacttaaaaa ctaaacctat tgaaagacca agaacaactg aaagtctttg    6720 cttttgtcaga tttttgacca aaaggaaaat taaagaaaca caccgtgccc atccaatgat   6780
ttcaccaagg aattttaaga gagaaaatcc tacttcttcc tcacccagta gccagtgaaa    6840
tgactgagca aattcacaag ttcactgggg ctgctttcat gtaacacagg acaacacat     6900 gacagacaca gtggaaccct acaggttgcc tagtatttga aagactgtga agaggaggag    6960
atgtcaaaat tcaaagtctt aaatgatgta gttttaagta tgttcagcaa tttcaccact    7020
cagtagtaaa gccagctaca gttgaaagca atcagaaatt tgagggtgt gaaataagca     7080 gaagcacaga agttaaggat ttgtattctt cccacatttt ccactttatt ttatactgct    7140
gagaaaaaac aaatttaata gttttctgct gtataagaga gacacattca ctttatgtca    7200
cagtaagagt cactcaattt taatacaact atctcaatgt ataaattaac attctcccc     7260 ctgcccacac atagtaagtc tcttatgatg ttgctgatta gagaagcaaa agttgccgct    7320
acaattctct tcctgcattt taatataaac aatcatcagt ctttctcttca tagagtgcag   7380 tgtgggcact atcatcagaa tgtaccagca ctgggtgtgc aaagtttaca aagattagca    7440
agagcaaaag tgttgagatt tttgaaattc atgctgctgc aaagaagtat gtaaaaactc    7500
actcaccata gaggaccaca cagaaactca ggcatgaagt tatatggctg tgtgagtggt    7560
ttgggagaag gaacggaaag cacttccacc aacctatatg cctgagcaaa ttaatgcaaa   7620
acctcagaag ctacaaaaaa gtttatctac ctaaattaaa attggtgtcc acagcagtag   7680
ccagcaaaat gcctgcgaag cgcaaagtgg taaatatttt agggtctgta ggtcatatgg    7740
tctctgttaa acaatatgta aatgaatggg tgtggctgtg ttccaataaa acttcattta    7800
taaaaagagg cagcatggta catccagtca gcaagctata atgtaccaac ccccggtcta   7860
acactaacca aatacctctt aataagccaa agaaactgtg tcctcttagg ccggaagcgg   7920
tggctcacac ctataatccc agcattttgg gaggccgagg cggggagatc acctgaggtc   7980
aggagtttga gaccatcctg gccaacatgg tgaaacccta tttctactaa aaatacaaaa   8040
attagccagg cgtgctggcg ggcgcctgta atgccaacta ctgggaggc tgaagcacga    8100 gaatcgcttg aacccaggag gcagaggttg cagcgagcct agatcacgcc attgcactcc    8160
```

```
agcctgggca acaagagaga aactccgtct caaaaaaaaa aaaggaaata aaagtataca    8220
aagtgaaaac aaagaaatta aactgccctt atttgccagt gacattactg tctatgcaca    8280
aaattccaaa aatctacaaa aaagcttcta gtactaaaaa tgagtttagc aaggttgtag    8340
aatccaaggt cagcatataa cataaaatca ccttcctata tactagcaat caccaactgg    8400
aaattgagaa gtatcattca caacagtacc acaaacatga ataaatgtg               8450
```

<210> SEQ ID NO 36
<211> LENGTH: 8420
<212> TYPE: DNA
<213> ORGANISM: Homo sapiens

<400> SEQUENCE: 36

```
tcttagtatg gtaaaccttt tgaagtagat tcaaatgaga atgggaagag agaaaaggga      60
gagaagcaac ataagaaatc tcttttaagg aattttatat agagagaaac agaggaatca     120
gttgatagtt ggaaattatt ttaaagaaaa tgggttattt taaagaaaaa aggtattaca     180
acatgtttgc actattgtgg gaataatcaa gttgagacag aaaattattt tttaaggaag     240
agtctaattg ctgaagtgaa agagaatgaa tgagaccctg tgcataagtg tgatcagata     300
ggagcatgta cagctcaagt aagaacagga agaaagagac aataaacatg tacagatagg     360
atgggctggt cgatgtggtg gtgaaaagac atgcgagtta ttactgatta cttctatttc     420
cccagtgaaa taggaagcca ggttcataaa ccaaaatgaa gaggagcgag gcagtattgg     480
aagttcagga aaagtaatag gtgtaaaaat atgtaaagta gaattaccag ggagtatgaa     540
gatacatttc caattaagga tgaagaattt aaagtgaggc cagccaatac ccctgctttg     600
cttcagctac atcagctgca taggttcagg cacagaatac atggaacatt gtatttaaat     660
agggcctgga ttttacaaaa gtaacacaat gaagaagaga gatgcaaggc tatttgaggg     720
tgtttgtggg agagattgta aaatattagc taagtaagaa ggggactgca aattttagtg     780
gtataaagga atgaggaaaa gtgtaaatac agtggggtca aagaatgttt ggagccaagg     840
cactagaggc aattagctga aaatgtaggt gattattggt gagtgacatg gtttaaatga     900
aaagtataga agggtacaat tatccatcat gaaaagttct agggtacaac taagatctga     960
gtagctgaag tagaatgaaa gtagaatgga cctttccata tccagccagg ttcagtgaca    1020
gaaggttagg aaacaaatta taaaccactt gagagaacat atcccctaag ttgttttttgc   1080 tattttttctt tcagcatata tttgttggaa tgccaactat gttcagttca attaatatgg    1140
gcttcttaaa taagggctcc agcactggat aatcctgcca tttatttga tacattccat     1200 cctgctgctc agatctattg gcatctacag gatgtctttt gagaagatgg gcattcacat    1260
ccctatgtcc tagcaaattt ccaactcaga aaaccacatt aggcttctct atatatcttc    1320
caactatttc aatggaaaat acaattctct gatttcttcc tatgatattt atcaaagaga    1380
atggtgcctg ccagttctag ggtgggggaa ctcaatacaa atcaccaacc tttagatgac    1440
accctgtctt caaagtgctt tcaaagtctg gcagaaaaaa agtacccagt ggctataaga    1500
ccacccagga gttcagtcat gcattctaag tagcagatca ctggaatgta attggctagt    1560
gagttcattt tactcttctc ttcttggtca catgttaccg cccttgtacc ctgcacgttc    1620
tctttcccag acttacaaag catgttctct tgaattcgtt ctcttttttaa attcacacag    1680 tcttaatgat tcttctttca caagagtctt tcactcttac aattcagttc aagtcatcca    1740
catgcttatt atgagcaagg gtctgggact taggggaaaa gggaataaaa agatgaatga    1800
```

```
aatgtgatcc ctgcagtcca agagcttgct gtgaaaaagg aagtttggct tacattgcct   1860
ccctaatccc ttggctaggc cagaacagaa tattgtctaa aacctcctca cgtcagcagt   1920
cctctggggt ggtgactgga agtagaattt aaacaaaaat ataattgaca cataataatt   1980
gtgcatactt atagggtaca atctgatgtt tcgatatgtg tttaaatggg tgcattgtgt   2040
aatgatcaaa ttgaggtaat ttatccacca ccttgaagag agattttttca atattctcat   2100 tgcgaagaag caggaatttt tagcagacaa ctgagatgct tcttgttcac actaagtcat   2160
tctgacgatg gatttacata acttgttgtt ttttttgtgt gtgtgttttt gagacagagt   2220
cttactttgt cgactaggct gaagtgcagt ggcacaatct cggctcactg caacctccac   2280
ctcccgggtt caaacgattc tcctgcctca gcctcctgag tagctgggat tacaggtgca   2340
tgcaactagg cctggctaat ttttatattt ttaatacaga tgggatttca ccatgttggc   2400
cctgctggtg tcaaattcgt ggcctcaagt gatctaccag ctgcggcctc ccaaagtgca   2460
gggattacag gtgtgagaca ccaagcctgg tacatttaca tttcttatct ggatctttcc   2520
tttagtaagt gctaaggaat cctacttccc ccaatatttt ttcctatttc aatgttttag   2580
catgtatcat gttactactt tgcagacatt tgattttccc ctttgtttac tgtaaagtat   2640
atttttatag cctttgtaat agaagtattc taaaatctgc ctgcaaccta tctttctgac   2700
tctgcatttt agggaataat tctctgttgt ggaatgaaaa aaaaaacaga gcctgtggag   2760
tcagagatct catttcaaat tatagttatc cctaggaata aatctgagtg acaggtagta   2820
tagtataata ataagtataa agctatggtt aaggaaaact caacaacctt atctgtaaat   2880
tgggatgaca acagcctacg tcaaaaaaat gtgaaggtaa atgagataat gtaaggctga   2940
tacttagtaa gcaatttaaa aacacccaaa aaactattgc catgattact ctacttactc   3000
tatttctcta tgctccaggc aaatgaacta ctaatgaccc aggggtcctt ccccattctc   3060
ttcttcacaa ggaaatattc tctctctgtg tgctgtttat taaaatctac tgccccttt   3120 agaagccttt ccagatcatc ccatggccaa gaacgatcgc tgcttcctct tctttacata   3180
cagatgtttt tctcctgctt gacaattatt tttgtgcaat tattttcctt ttgattgtgt   3240
ttttaatgtc ccccccaccc cacaattttc cagactgttt gctccacgag agaggagacc   3300
atcatctctg tgctcaccgt tgtatgacca gtatcctgag gagtggctgt tacataatta   3360
catcaggcac tcaataaaaa tttgatgaat aaacactgga ttttaaggca ggtatcatat   3420
cttacatagc atatcatatc ttacatttta tgtccctcac ataaatacca cagagtgaag   3480
tatatgacag ataaggtcat ttctcttgat aagtacatag tccagtctga aacagatatg   3540
ccaaaaaaaa acaaaactgg agtaaacaag atgaattgtt ttaatagagg cactgtatta   3600
gtttcctagg actgccagaa caaatcacct caaacttagt ggctgaaaac aacaaaaatt   3660
tattgtctca cagttataga tgttagaagt ataaaattaa ggtgtcagtg ggattggttc   3720
cttctggggg ctgtggaaga gaatctgtcc caagccttca cactgtaaag tacagtactg   3780
gagggatagg acttcaactt gctctatctc agatagagag gagccatttg ttgtgaattg   3840
agaagagggg tatgttgaat ccataataag cacataaaaa cttggctggt tcataggaga   3900
agtaacatgt ttccagctct agtaaaaaac aaattgaagt ggcctataaa aaggtacaga   3960
gtacgacaga atgaaaaata aatgaacaag aatacagaga ggatgtggta aattatcatg   4020
tttccctaat atgttattgg acactaaatg gtattagaat tatttatcaa taataattct   4080
aaactgttgc aattgaaaga atatattaag tggtgttata tgagaagtgc cagggcattc   4140
tcatttctgt ccaatgggag aaacattttc gtttgagacc tccgtgaata atacagtctt   4200
```

-continued

```
ttagttagga gagctgcatt ttgagtggtg caggcagaat ggcgatctct cacccacaca    4260
aacactaaga tagagagaga cagagacaga gacagagaca gcagagagag acagagaaag    4320
gaagtacagg tactcagata gagataagcc atttcttgac attaagaaat aaagtagaat    4380
ccattggagg gaaataaaac tgcctcagga acagagttaa ttcacataca catgcaggta    4440
aacacacact gcttgatact tactgtggac tttgaaaatt atgaatgtgt gtgtgtgtgt    4500
gtgtgtacat tcagccctcc atatccatgg attttgcatt cacagattca accaaccatg    4560
aattaaaaac atttggaaat aacaaacatt aaaatataac aatacaacaa taaaaataat    4620
acaaataaaa aatatagtgt aacaactgtt tacatagcat gtatgttgta ttaagtagta    4680
taaatctaga gattacttaa tgtataccag aggatgcata ggctatatgc aaatactatg    4740
ccactttaaa ctgataagaa cagatactaa acttcatctt agccaaaagt cagagaaaca    4800
atataactat gccattttac ataagggact tgagctgagc atcctcagat ttcagtatct    4860
ttggagttcc tggaaacaat tccttgtttt atatatatat atgtgtgtgt atatatatat    4920
atatatatac acacatatat atatatatat atatgataa gctactgagt gacaggtgat     4980
attataccat accacttgtc actcagtagc tgtatatgca tatgtatata tatacatata    5040
catatatgtg tgtatgtgta tgtgtgtgtg tgtgtgtgtg tgtgtgtatg ctgtctttcc    5100
tcggtatcac agggaattgg agatatatat attcttttca gtacaaaaaa aattgaacac    5160
agatgggtat ggtaccagaa cagaaggtaa agacacatga aaaaatttg caacaacatg      5220 aatggaactg gagatcatta tttgaggaga aataatccag gcacagaaaa acaagcattt    5280
tattatttta ggtgaaagac aaacatttta ttttaggtga aataatccag gcacagaaag    5340
acaaacattg catgttctca tttatttgtg ggatgtaaaa atcaaaacaa tagaacgtat    5400
ggaggtagac agcagaagga tagttaccaa aggctgcaaa gggtagtgta ggctttgagg    5460
gtgaggtggg gatggttatt gggtacaaaa aatagttaga aagaataaat aatatctagt    5520
atttaatagc acaacaggtt gactatagtc aaaataacat aattgtacaa tttaaatatg    5580
aaattaaata tatatacaag actagaacac caagttgaat gactccagct tgcgaaaccc    5640
acattgatca ccatgcttgc cccaagggaa gctgtacaat gtctggctcg tccagaaccc    5700
catcatttat cactagcaat ctattgtcca taatcatgtt taaattaata gcattttaaa    5760
ggtacaaata ttttttaaaa aacaaataat tatttaattc gccttttaaa agcttttaa      5820 aaacgttttt aaaaactttt ttaaagtcct gaggactatt ttctttaaag tgctcagtta    5880
cagagctcca tatattgggc tatgatagcc ttacctgatt cttgccaaga atctagtgcc    5940
cagaaaatgc aaatacaaag taagcaactg aaaaataaac aaataagttg gaggtatgct    6000
acctgttgaa atatgaccta gcgcaaacac ctatgccact tgcttatgaa atcatatagg    6060
ttttcggtgt gcagttttga ctgaatgagg gagtttacgc tggaccacaa ggggccccct    6120
ctgtcaataa cgtactccat ttgtgtatta agtcaaaaat gaaatggaag agaaaagaaa    6180
catcgatgac cccaagtctc tttaattgaa tggaggtaaa agggaaacaa cgaatgagaa    6240
aagtactctg cccttttaag aatcttgcat tcacattcct gatgaagtta ttttcctcc      6300 tctcactgat tcccatttca ctctattaca tagcaccgtg ttccccagga gctcctgaat    6360
gaaggacatc actcagctgt gttaagtatc tggaacaata aatatactag tttcaatgtc    6420
taggctatgg gtattccttt ttactgaagg tatgacatat agctgcccag gcctgactaa    6480
attaatagta ataataatta ataatggcaa attttttattc tattaagtta cttggcttga    6540
```

```
cttgtagaaa tagcaacatt catctgaaat gcccccctcct acacttatgt ctaaggacaa      6600
atcccacata caccacagat aacttcattt tacatgtttt attctgttac caaactaaat      6660
ttttatcata tagtctgttg ctcactgaac tcttcagtaa ttctcaacat accatgtaaa      6720
gcattaagca cagttccaac acagagcaaa tgagcaataa ctgttagtta ttataacatt      6780
attatgtgtt ttcagtgcat taaaccactg gtctgatacc tagcccaaca ttctattaaa      6840
ccacataatc cagttgaata atatatgata atataataaa atggcgataa gtgctaaata      6900
tccagataga aacacagatg gaatcagaca gctttcccaa gaaatagaga aaatagtaga      6960
taggcgatct aggcctaagc actctaagca gaagctaagt tatcacagga tatcttggca      7020
atctgtggca cgtgaaccct ttcttctgg agtctggaac tatgttgcaa ctctcacttt       7080
ctccctatct agagactcag tttgttccct tgtgattatc agcagttgag aaatccttag      7140
accttctgaa aggactactt tttaaattta tatatataat atttaaaata catatcttta      7200
tatataatat atatttaaat atataatatt taaattaata tatatttaaa tatataatat      7260
ttaaattaat atatatttaa ataaataaat ttatatttaa atatataata attaaaatat      7320
atttttaatg aacagagagt aaaggattat tttgaagaga aactcctggt tcccacttaa      7380
aatcctttct tgtttccaag tttttcaaat ggagccctct ttaccagctt gcccctcag      7440
agataagctg ttccctact tattcagatc tgagatctga aaacattcct tttcctgtga       7500
gttcagctag gacaaagatg gagcttttg ataaaatttg gcaaacacat ttttaaaga       7560
tgaaaatttt taaaaattga aaaaaaaca tttatagaaa gagacttcta atccaaattt      7620
aacttctcaa actatgtttt gaccggctag cataatgttt cagtcttttct ggagaatgcc    7680
ccttgaaact gttttcttct acacaacttc ctccttcct ttgactttcc tgctctggaa      7740
gggaagaaca ggaagaggac agatcaaatt actcaagagg aaggacaaga aataaggaac      7800
caaattatca acaattggag aaagaaagct gatgtcagta tcatttcata tatgattatg      7860
tcagagtcag gtggataagc caatcctgtt gaatagcata cttttcctgc tactcctgaa      7920
gggtaaagag gtcttctct tacaaagccg tcctagctag taatcttaca ggtgcaaaaa       7980
gcttgtttc atgttattc ttagtaactc aaaatacctc taaagttata catattatga        8040
aagtactaca gtcacagtgc tgagaaaagg agtaaataag acaatgtata taaaaacact      8100
tggctcagcc cctggctctg tggttgataa atattaagtt agtattcatt attattataa     8160
tttccaaaga gtccattaaa agatatagaa gaagggaggc agcaataaca ctaagagaaa      8220
attccattat ctccaactat ttatcctcta gcccaaaata attgccatta gaaagagcaa      8280
cttaacaaa aattttaagt tgcaatagat gttcaacttt aaatccatcc cagaaaaatt       8340
tctaaccaaa ggagcataga agatttgatc ttattttcta agtagtatag acttaattgt      8400
gagaacaaaa taaaaacttg                                                  8420
```

<210> SEQ ID NO 37
<211> LENGTH: 8475
<212> TYPE: DNA
<213> ORGANISM: Homo sapiens

<400> SEQUENCE: 37

```
gcataacttg taagaaatgg agtgaggtct cagttcaaac tggcttctgt atgacttcaa      60
agccaaagtc agcaacttag aaggcaaaaa ttataattta gttggcaaat acgagaaaag     120
gtcagaaaca catgaaatga agctcaatag gaacacttac agggtagcag ggtagtagcc     180
tagggaaaaa agtcagacac taaaattgtt taaataggta agttcaaggg acaggtaaag     240
```

```
accttagtgg gtaagaagcc aatcagcaga cgaactgcaa gcaagcactg tctctctttc    300
ccttctgtct cctcttgtag taactgacca caattaaggc tgcctagggg aataatgaag    360
taatcctcct attatcagca atggtctgat ccagtgccag gcaccacaga caacttggtg    420
ttcagagaag atccttcaag atgaacaaag ggtcaaaata aaaaattcta gaagagagaa    480
gactgatcac aatttaatgt aaggcttgga aggaactgat ctctaccttc cttaacatct    540
caagaacttc ctcagattca ttggatgttg agtgtgtgtg agtctagtag aaaaatgaat    600
ttttgtttct taacttggat atgtgattag gatgttaata attaagtctg gctaatatt     660 gaaggtatct tatgatgggc ttcttaaagc attgatcaca aagactgcat gttcataaac    720
tgagctgcac ttgttaggat tctagatgtt tgaaatttct tgtgttattt ggtctcaga     780 tttctagaca aattttctca aattcctatt tcactttttg acatatcatg agtgactcaa    840
atgtttgccc ttgagtcgga aaacacccag cattaggaat aggcacataa acataatact    900
tcaagcttca gatttaagct caattataaa gtgtttaaag gctgtgctga tagttcttct    960
gagtagaatt cctacaacta tgggtttgtc tataataaaa tgttcactct atattgaacg   1020
ccttatttaa aactcgaaat gtgtaagtag taataaagaa aatatgtcct cctgtaacca   1080
aagctaggac cgattacatg ttcacttgac tgacagatac aatcacctat attaggagca   1140
atcagcactt ccttacaaac taacaacttg agatgtagtg ttcccattgg ctatgaagat   1200
tttctttatt tactcagaat agtctgtagg atctgccagc tgcccctgat tataccagct   1260
gcacccaatg atcacagtga acattatttt acattctaaa taactggtgc aaggtgagcc   1320
atggttttct gagtttccta tcacctttgt gtttcaggtc ctcaaatgtt aatttgtaaa   1380
gctgctgttt caggcaaaac taacaaaatt agcatctaat caataaccat actatgtcca   1440
cccatatcct ataacacaga agtaggggaa gagtgagaaa ggtggaagtg gagaaataga   1500
ggcccaaaaa gaaagtttta tcacaggaat atctagatgt cttctgggat tgtctgttaa   1560
agagctgtga cactcatata aatgcagaat tactctcttt cttccttgtt ggttagaagg   1620
ccaagggtgc catggtaata ctaccaaaca tatatcaaag cttggcagga aaaatggtac   1680
cttcagaaat tttataatct gatatcaaat aggtcaagaa atataataaa actagtttct   1740
ttggtttcct tagaaacctg gaaaacttta aattagaaac ttagaaagct ttaaatcaga   1800 cttttgtagtt aaaaaaggaa attttagttc cttccagcat tagaattccg tgattctctg   1860
actctgagcc tggattaaat ctagcccagc tgagtggaaa cttaagtaac tagctggttg   1920
cctttagtga tcttccactt tatggctgct tccgcctaag aagttcatca tcgtgactta   1980
ctttctttgg ggcaaagtcg tgactaactt tctttggggc aaagttggaa agcagaggtc   2040
aaagtcaatc agaaatggga caaactcact tcctactgcc tggtgaaggg gccattttca   2100
gtagcccctt ttcaagatta gtttcattca agatttgata agctgttttg actttactat   2160
agatcttatt atccatgtca gttaagttta tgcttccact aaatctatct gaattcaaaa   2220
ggtaaaaagc taatgctcag tcttatcaga tttatcttat ttattaatag aatgtggatt   2280
tttttaagca tataacaata atagtaatga taggaccata aatgtggatg gctctttaca   2340
agtcactaac attcataaaa ttcctcaaca acacactctg aggccataac aaactttttag   2400 aaataacaca attggctacg gaactccagc catctagctt catgggctcc cactttaatt   2460
tcaaaacaac agaactgtgc acattcattt acatgattag ggcagagctt aactgtatct   2520
catgtagcac ctacatcatt cttcagacaa acttattgcc ttttacagac aagaaaactg   2580
```

```
gggctcaaaa aaggacttgc ttataactgg ctaataaaga ggaactctgg gttcaaagtg      2640
agtccaattc tttcttccac ccacagcttc tgctaaagtc attacagaaa tgcatagagc      2700
agttcttcca cgttattgct taggtttcta aagagcagtg acctaataca acatgctcta      2760
taatttatta ctgatttaac tatttcacta aggattcact tttaactttt aacttgtaaa      2820
tatgtctaat aaacaccact gaaatagcaa cctctttctt catggccttg tggttgtaaa      2880
gcaagctagt aatatatgtc tgtggatttg tgctaataaa gttctataca cctcattaat      2940
tccacaaatc ctactgggta tttcttatct gccagatcct acgctaggta ctggatacac      3000
agtactgaac aaaatgggta caaatgagcc tcacagagct tgtttcattg aaaagcagag      3060
agatacacac taatcaacaa attaatagta acacactacg atgtgttttg aaggaaaatt      3120
agagcatcaa agagacggtg ttagcaggtg aggggagct cttttagatg agaatgaga       3180 atgcctccct aaagacatgg gaataaattg agatcacaaa aaatgagaaa tagccagcct      3240
tgagaagagc agaaggaaga acattcaaag gaaaagaaag tgcatactgg aaagcctgaa      3300
cactagagtt tggtgtatgt aaggagctga gcaatggtca cttgtgtgat aagatgtgtg      3360
gatgtggggt gggggcagg ggtgagtccc acgcagctct taagtgtgtc ctcagactcc       3420
tgtggtttcc atcagccaca acctgaataa ctgtgtggta atccaaaaat gattacagat      3480
taaacatata aaatatcat tacacccata gtacctaagc caaggacaca gtattctatc       3540
ttttcaatga agatctgcat gaagtaaaat tattatatat aatttaggt attgatatag       3600 atacatcagt ggatagatat agatatgtgt ctctggtata gaaaaagtt ttaaagggat       3660 attaaaagtt cttatcttgc agggttgaag attgtggcaa ctttcatttc ttttaattt       3720 taagaaaaaa gtggtattat gggggattag catgtttgtg ggtatatgta tattttaat      3780 taaaaaataa acaacaaaat gaaaacgtttt tccttctatg aaagcctaat aagaagaaat     3840
ttcagctgtt ttaacttagg gagctaaaaa catcaaatcc aagaatgttc tctggaactg      3900
agctcaatac attttattt gagtaagaat tggatacatt tccatcccct tggggctcca      3960
gtctgtcaat atttttacttt tcagcgataa aaagacacat gtagataatc acagtgacct    4020
cagtaacttt ccttctctta tttaagtttta ttttattttct atcgtagttt tccctgttaa   4080
agattttttc tttttgctta catatataat tttagagaat aacaatgcac acacaaaaaa     4140
ttcctcttgt tctgctagac ctggactttt tctctaatat atatctccat tttttgtctt    4200
ttttcagacg tattttggaa gcaaaggaga gaattgctat atagctgact tcctcttctc      4260
atcaacagtg ttttaacagt ttttaagcaa aagtcagctt tgtttatcta agattttttt     4320
tgctggcatt taacctaccc ctgcctcccc tttcccaagt ccacttcagc caacctctca     4380
ttcgacaggt accaccctct aacataactg aaataatgtc taccattact ggatcttgct     4440
agcaaagaat ctcaaatttt cccacttggt tgtaaattat tttgtaatct ctagtgttta     4500
aggtgcgctt gtcctatcta atcccctccc tggcaggaca ccttacagaa cctaccctt      4560 acactagtca ttaagcacca tcagggacgg atggctgtgt cactggtctg tttggtattc     4620
cctactgatc ctaccatgtg gtgattatct atgacttccc taatccctgg ctgccttagc     4680
tgggactggc tgacatgctt ctcaggttgc cgctggcttt acagtccttt actgcccatg      4740
ccactttgga gataggcagg gctagtactt ttctatataa gcccccaaac ttgactttgt     4800
gtttcacagt aggtgaaaaa gttgggtctc ttttctttta cttttctttc cacaagatga     4860
taaagctagg ggaagcctgt ggacatggtt tatttctgca actgcaatga ttgattggtg     4920
cttcctgctg cttacttcct aaactttgtg ctcagtgtca gatccctagc agtttctatc     4980
```

```
ccctgctctg ctaaaaaaga atggatgttg actctcaggc cctagttctt tttaattaaa    5040 ttgtatttt  gttatcatta ttattattat tattttgaga tggggtctta ctctgtcgcc    5100
caggctgaag tgcagtggtg caatcacagc tcactgtttt agcctcctga gtagctggga    5160
ctacaagcgt catgccacca tgcttctttt aatttttta aaatggtttt ctgccttcaa     5220
ttctaagcac ttctcaattg taaccaagag ataatacttt ttatgaattc ttaaagttat    5280
caacagatac tcaaagtttt agcaaagtct aaatgatatt aagcttgtcc ttattgccca    5340
agtgacttca atgactattt gttaattgca accaagggtc atttttttaaa tgaatatata   5400 ttattattat atatataata ttaaggtcct caaataccta aaagtttagc aaaatctaaa    5460
taatattgtg catattcttt tattactgta ttagtccgtt ttcatgttgc tgataaagac    5520
atacccaaga ctgggcaatt tacaaaagaa agaggttcac tggactcaca gttccacgtg    5580
gctggggagg cctcacaatc acggcagctt acgggattgt tgagaaatga cacttctcaa    5640 gctgggcta  aactatctct gtggtagttg ttctgattca agtattgaat tggttttttt     5700
tgtttttttt gagatggagt ttcgttcttg ttgcccaggc tggagtgcaa tggcacgatc    5760
tcagctcacc gcaacctctg cctcccgggt tcaagtgatt ctcctgcttc agcctcccaa    5820
gtagctggga ctacaggcat gagccaccac acccagctaa ttttgtattt ttagtagaga    5880 catggttct   ccatgttggt caggctggtc tcaaactccc aacctcaggt gatccacctg    5940
ccttggcctc ctaaagtgct gggattacag gcataagcca ccgtgcccgg ctggagcatt    6000
ggtatataaa agctgcctag gtaactctaa cctttggccc catacatctg aaggataccct    6060 acaatgcacc tgaaaaatgc aactgaaaca gtagttccct gggaccacac actcagaaag    6120
ggggtgtatc aggagatcta gggaccagga gggtggaaga cctaaggcag cactacagat    6180
gatggagaaa aacccactgg ggagggggcga tcctaaccttt gagaatcact gagatcatgc    6240
agaagtattt gatcctacag cattaatatt gtattgtatt gtattagtat atatatatag     6300
tgtatatata tagtattagt atatatattg tattgtatta gcatatatat actaattgta    6360
ttgtattgta tttatatata tagtattgta ttagtatata tacagtat  atatgtatat     6420 atactaatac aatgtactaa tacaatacaa taccatatat atatacacta acacaataca    6480
attagtatat atatatatat atatactaat acaatacaat actatatata tactaataca    6540
atatatacat atatactcac caagacatat tagtggtctg atgtctggct gccacactca    6600
tcttctacct tcagctctgc tctaccaaat atcatttgtt tctgggatct ttgcagtcca    6660
aggaacttca tccttgatat cccaccccctt actaactttt tttttttttt tttttttga    6720 gacggagtct cgctgtgtca cccaggctgg agtgcagtgg tgtgatctcg gctcactgca    6780
agctccacct cctgggatca caccattctc ctgcctcagc ctcccaagta gctgggacta    6840
caggtgcccg ccaccacacc aggctaatgt tttaccgtgt tagcaaggat ggtctcgatc     6900
tcctgacctc atgatccatc cgccttggcc tcctaaagtg ctgggattac aggcataagc    6960
caccgcaccc ggccacccct tactaatttt tagtaacgtc caaggattaa aggaaatttg    7020
ccttacctat ttaacaggaa tcaacaggggt taatctcact ccctttctaa aaataattta    7080
taaacattgc agacaatctc atctatccct gtctaaactg tgtggaatta ctgccattta    7140
atgtaatcag tctactcatt tagtttgcct aaggaatttt tgaaaaaaca gttaaatgaa    7200
tgacttaatg gaataaccag gaagttgaag tctccaatag taagaatgaa ctcttgctct    7260
ctggataatc aaatgggtcc ttcctccttc aggtagatca tgccatttcc tcacttacac    7320
```

```
tgaacaggta aacaacataa ttactgactt caacttctag ttaattcctt cttttatcac    7380
tgagtatcct ttggctggga gttttgttgg ctatgctgcc atttttttcta gttatcacag   7440 tcctataaca taccaatcct tcaatataac tcatctttaa attgtggttt taccttctca    7500
agaagttatt aattatgcca gtgctaaatc ttctaaaatg attgttgact tgttgattag    7560
cccccatgca attcccctct cccgtccctc agcacgtaag gaatggccct ttgcttactt    7620
ccacagatcc ttaaatctac cagttagaag ctaatagcct acctctctac caggaaggaa    7680
ctgtgggctg gaacataata catgttgact tataatttct tagaaaattg tgtgagaaac    7740
atcaaactcc tgattccagg atatgccaaa gacacatcat taaaaagcaa aacaaaacaa    7800
aacaaacctc atttgacgtt gctagtagtg gcatatttca tcaagatcag ctcaaataaa    7860
tagaagtgag attttcacac aaattagact gtagtgcttt ttttttttaac ttatctttac   7920 catatgattt ttaacggtaa aaaaaatcgt ttgagatatt agatgtataa tatttatcat    7980
ccaattactt cattagttca atctttttc aatggcgctc ctgcatctga gaataaggtc     8040
agaaaatttc atgttctgat ttcatgctga ttttcagaag aaaaatgtta gttttgtata    8100
gaataaccca tcctaagaaa tacatttctt attatatttc ttatcttata tttcttagga    8160
caatgagcta ttcaaagggt gatgataacc agcaccatca gtcagcatta tctaagaata   8220
agaatctgtg tttctacata cagacctcct aaaaaggaac ctacacttaa caggattccc    8280
caggcaattt ggatgcacat taaagcttga gcaacactgc attagaaagt tagttttcca    8340
tcacaaaaac agtaacaaaa ggaatataaa gtaagttact ttaataatat aagaagaggg    8400
gcaggccggg cgcagtggct cacgcctgta atcccagcac tttgggaggc tgaggcgggt    8460
ggatcacctg aggtc                                                    8475
```